US009157125B2

(12) United States Patent
Samuels et al.

(10) Patent No.: US 9,157,125 B2
(45) Date of Patent: Oct. 13, 2015

(54) GRIN2A MUTATIONS AND USE THEREOF FOR THE DIAGNOSIS OF MELANOMA

(75) Inventors: Yardena R. Samuels, Potomac, MD (US); Wei Xiaomu, Ithaca, NY (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 10 days.

(21) Appl. No.: 13/982,392

(22) PCT Filed: Jan. 26, 2012

(86) PCT No.: PCT/US2012/022687
§ 371 (c)(1),
(2), (4) Date: Jul. 29, 2013

(87) PCT Pub. No.: WO2012/106175
PCT Pub. Date: Aug. 9, 2012

(65) Prior Publication Data
US 2013/0309254 A1    Nov. 21, 2013

Related U.S. Application Data

(60) Provisional application No. 61/462,471, filed on Feb. 2, 2011.

(51) Int. Cl.
 C12Q 1/68 (2006.01)
 C07H 21/02 (2006.01)
 C07H 21/04 (2006.01)

(52) U.S. Cl.
 CPC ........ *C12Q 1/6886* (2013.01); *C12Q 2600/106* (2013.01); *C12Q 2600/118* (2013.01); *C12Q 2600/156* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 6,333,152 B1 | 12/2001 | Vogelstein et al. | |
| 6,582,908 B2 * | 6/2003 | Fodor et al. | 506/9 |
| 7,655,785 B1 | 2/2010 | Bentwich | |
| 7,687,616 B1 | 3/2010 | Bentwich et al. | |
| 2004/0241651 A1 | 12/2004 | Olek et al. | |
| 2005/0255487 A1 | 11/2005 | Khvorova et al. | |
| 2007/0031843 A1 | 2/2007 | Bentwich et al. | |
| 2007/0042381 A1 | 2/2007 | Bentwich et al. | |
| 2008/0015160 A1 | 1/2008 | Inazawa et al. | |
| 2011/0178283 A1 | 7/2011 | Rigoutsos et al. | |
| 2011/0191912 A1 | 8/2011 | Alexandrov et al. | |

FOREIGN PATENT DOCUMENTS

| | | | |
|---|---|---|---|
| WO | 99/47706 | * | 9/1999 |
| WO | WO 2005/091849 | | 10/2005 |
| WO | WO 2007/150071 | | 12/2007 |
| WO | WO 2008/021290 | | 2/2008 |

OTHER PUBLICATIONS

Hirschhorn et al. Genetics in Medicine. vol. 4, No. 2, pp. 45-61, Mar. 2002.*
Hattersley et al. The Lancet. 2005. 366: 1315-1323.*
Lucentini et al The Scientist (2004) vol. 18, p. 20.*
Gagneux et al. Molecular Phylogenetics and Evolution. 2001. 18: 2-13.*
Halushka et al. Nature. Jul. 1999. 22: 239-247.*
Mummidi et al Journal of Biological Chemistry 2000 vol. 275 No. 25 pp. 18946-18961.*
D'mello et al. Frontiers in Oncology. Jan. 2014. 3:333, p. 1-9.*
Stark et al Nature Genetics. Feb. 2012. 44:165.*
Barnby et al. Am J Hum Genet. 2005. 76: 950-966.*
Bashyam et al., "Array-Based Comparative Genomic Hybridization Identifies Localized DNA Amplifications and Homozygous Deletions in Pancreatic Cancer," *Neoplasia*, vol. 7(6):556-562, 2005.
Cavalheiro et al., "Glutamate Antagonists: Deadly Liaisons with Cancer," *Proc. Natl. Acad. Sci. USA*, vol. 98(11):5947-5948, 2001.
Kim et al., "The N-methyl-D-aspartate Receptor Type 2A is Frequently Methylated in Human Colorectal Carcinoma and Suppresses Cell Growth," *Oncogene*, vol. 27:2045-2054, 2008.
Loukopoulos et al., "Genome-Wide Array-Based Comparative Genomic Hybridization Analysis of Pancreatic Adenocarcinoma: Identification of Genetic Indicators that Predict Patient Outcome," *Cancer Sci.*, vol. 98(3):392-400, 2007.
Rzeski et al., "Glutamate Antagonists Limit Tumor Growth," *Proc. Natl. Acad. Sci. USA*, vol. 98(11):6372-6377, 2001.
Wei et al., Exome sequencing identifies GRIN2A as frequently mutated in melanoma, *Nat Genet* vol. 43(5):442-446, May 2011.

* cited by examiner

*Primary Examiner* — Carla Myers
(74) *Attorney, Agent, or Firm* — Klarquist Sparkman, LLP

(57) ABSTRACT

Described herein is the identification of 68 genes with an elevated frequency of somatic mutations in melanoma. Nine genes were identified that exhibited recurring mutations in melanoma. The TRRAP gene was mutated at nucleotide 2165 (C2165T) in six different melanoma tumor samples. In addition, 16 genes were identified that were highly mutated in melanoma samples. The most highly mutated gene identified was GRIN2A, which was mutated in 34% of melanoma tumor samples. The study disclosed herein identified 34 different nonsynonymous somatic mutations in GRIN2A among 36 melanoma tumor samples. Provided is a method of diagnosing a subject as having melanoma or susceptible to developing melanoma by detecting one or more mutations in the TRRAP or GRIN2A genes. Further provided is a method of selecting an appropriate therapy for a subject diagnosed with melanoma by detecting the presence or absence of a mutation in TRRAP or GRIN2A.

9 Claims, 18 Drawing Sheets

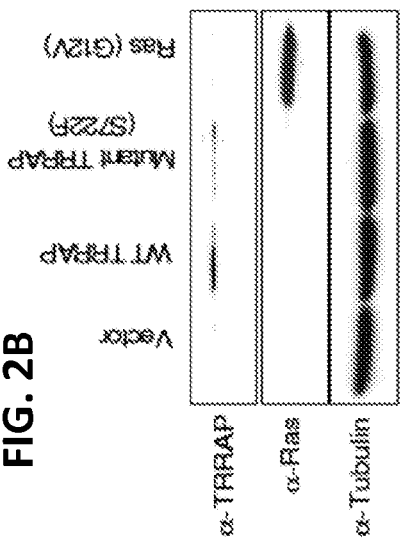
FIG. 2B
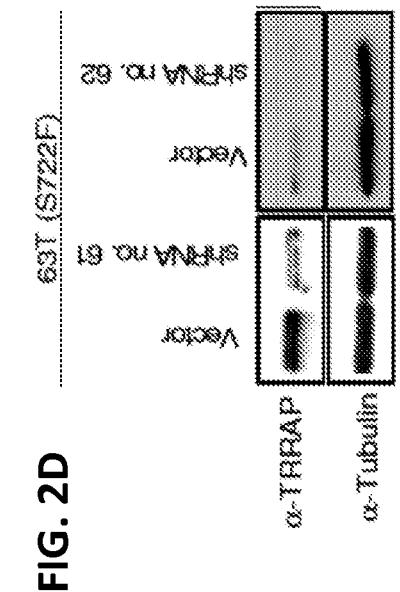
FIG. 2D
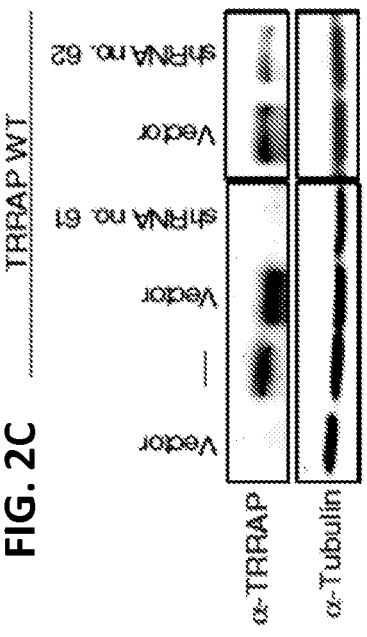
FIG. 2A
FIG. 2C

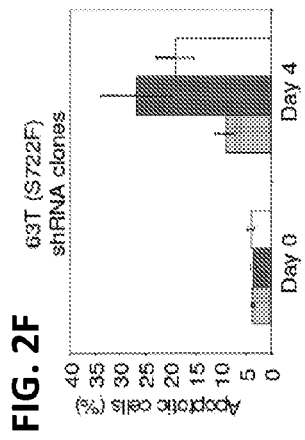
FIG. 2E
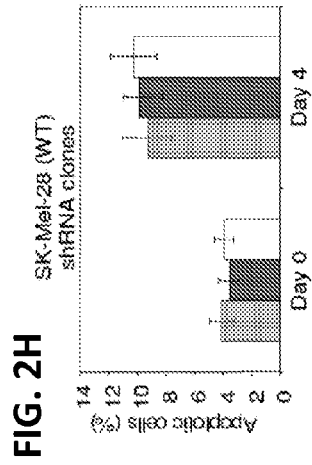
FIG. 2G
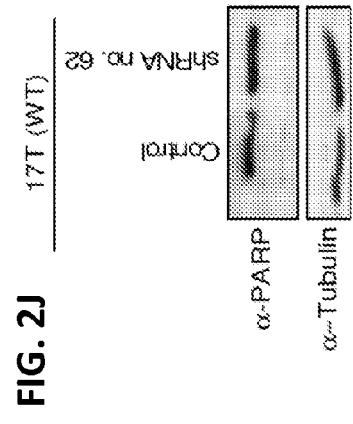
FIG. 2I
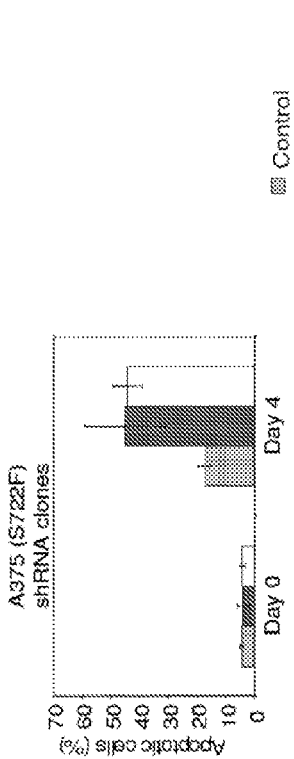
FIG. 2F
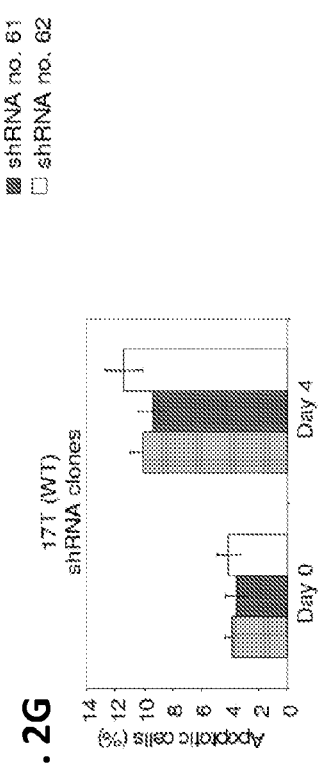
FIG. 2H
FIG. 2J

FIG. 6

TRRAP S722F (C2165T)

```
NP_003487 Homo sapiens              697 LPEMGSNVE--LSNLYLKLFKLVFGSVSLFAA--ENEQMLKPHLHKIVNSSMELA 747
XP_860949 Canis familiaris          696 LPEMGSHVE--LSNLYLKLFKLVFGSVSLFAA--ENEQMLKPHLHKIVNSSMELA 746
XP_001136733 Pan troglodytes        697 LPEMGSNVE--LSNLYLKLFKLVFGSVSLFAA--ENEQMLKPHLHKIVNSSMELA 747
XP_583735 Bos taurus                698 LPEMGSNVE--LSNLYLKLFKLVFGSVSLFAA--ENEQMLKPHLHKIVNSSMELA 748
XP_213706 Rattus norvegicus         699 LPEMGSNVE--LSNLYLKLFKLVFGSVSLFAA--ENEQMLKPHLHKIVNSSMELA 749
XP_414752 Gallus gallus             685 LPEMGSNVE--LSNLYLKLFKLVFGSVSLFAA--ENEQMLKPHLHKIVNSSMELA 735
XP_001919276 Danio rerio            652 LPEMGSNVE--LSNLYLKLFKLVFGSVSLFAA--ENEQMLKPHLHKIVNSSMELA 702
NP_001074831 Mus musculus           697 LPEMGSNVE--LSNLYLKLFKLVFGSVSLFAA--ENEQMLKPHLHKIVNSSMELA 747
NP_001097192 D. melanogaster        664 MEEMGSNLE--RSNLYLRLFKLVFGSVSLFPV--ENEQMLRPHLHKIVNRSMELA 704
XP_556172 Anopheles gambiae         708 MDEMGSNIE--RSNLYLRLFKLVFGSVSLFAA--ENEHMLRPHLHNIVNRSMELA 748
NP_001022032 C. elegans             723 MKLLEVSND--KTMLYVKLFKIIFSAIGANGSGLHGDKMLTSYLPEILKQSTVLA 775
NP_011967 S. cerevisiae             748 LKDLG-NVDFNTSNVLIRLFKLSFMSVNLFPN--INEVVLPHLNDLIINSLKYS 799
```

FIG. 9A

| Chr | LeftFlank | RightFlank | Refseq | Transcript | Type of mutation | Ref_allele | Var_allele | Ref aa | Var aa | Strand | Normal name | Normal MPG/coverage | Tumor name | Tumor MPG/coverage | Sanger evaluation |
|---|---|---|---|---|---|---|---|---|---|---|---|---|---|---|---|
| chr7 | 140,099,604 | 140,099,606 | BRAF | uc003vwc.2 | Nonsynonymous | A | T | V | E | - | 43N | 0.74 | 43T | 0.23 | somatic mutation |
| chr5 | 13,807,371 | 13,807,373 | DNAH5 | uc003fd.2 | Nonsynonymous | C | T | E | K | - | 55N | 0.70 | 55T | 0.50 | somatic mutation |
| chr3 | 407,763 | 407,765 | CHL1 | uc003bcw.1 | Nonsynonymous | C | T | H | Y | + | 24N | 70.00 | 24T | 0.54 | somatic mutation |
| chr12 | 116,182,707 | 116,182,709 | NOS1 | uc001wm.1 | Nonsynonymous | G | A | S | L | - | 24N | 74.00 | 24T | 0.63 | somatic mutation |
| chr18 | 48,532,493 | 48,532,495 | DCC | uc002fe.1 | Nonsynonymous | G | A | G | E | + | 12N | 35.00 | 12T | 0.66 | somatic mutation |
| chr7 | 140,099,604 | 140,099,606 | BRAF | uc003vwc.2 | Nonsynonymous | A | T | V | E | - | 22N | 0.71 | 22T | 0.68 | somatic mutation |
| chr7 | 140,099,604 | 140,099,606 | BRAF | uc003vwc.2 | Nonsynonymous | A | T | V | E | - | 91N | 0.72 | 91T | 0.68 | somatic mutation |
| chr19 | 48,371,430 | 48,371,432 | PSG5 | uc002ovu.1 | Nonsynonymous | G | A | S | L | - | 24N | 93.00 | 24T | 0.71 | somatic mutation |
| chr19 | 61,082,008 | 61,082,010 | NLRP4 | uc010etf.1 | Nonsynonymous | G | A | D | N | + | 18N | 57.00 | 18T | 0.71 | somatic mutation |
| chr19 | 48,371,430 | 48,371,432 | PSG5 | uc002ovu.1 | Nonsynonymous | G | A | S | L | - | 55N | 0.70 | 55T | 0.75 | somatic mutation |
| chr3 | 406,015 | 406,017 | CHL1 | uc003bcw.1 | Nonsynonymous | C | A | E | K | + | 55N | 93.00 | 55T | 0.81 | somatic mutation |
| chr3 | 407,740 | 407,742 | CHL1 | uc003bcw.1 | Nonsynonymous | C | T | S | F | + | 96N | 0.70 | 96T | 0.82 | somatic mutation |
| chr1 | 20,871,077 | 20,871,079 | KIF17 | uc001bdr.2 | Nonsynonymous | C | T | E | K | - | 18N | 25.00 | 18T | 0.85 | somatic mutation |
| chr7 | 140,099,604 | 140,099,606 | BRAF | uc010etf.1 | Nonsynonymous | A | T | V | E | - | 5N | 0.73 | 5T | 0.86 | somatic mutation |
| chr7 | 98,347,737 | 98,347,739 | TRRAP | uc003upp.1 | Nonsynonymous | C | T | S | F | + | 96N | 0.70 | 96T | 0.92 | somatic mutation |
| chr5 | 13,807,371 | 13,807,373 | DNAH5 | uc003fd.2 | Nonsynonymous | C | T | E | K | - | 24N | 93.00 | 24T | 1.03 | somatic mutation |
| chr19 | 61,062,014 | 61,062,016 | NLRP4 | uc010etf.1 | Nonsynonymous | G | A | E | K | + | 24N | 93.00 | 24T | 1.08 | somatic mutation |
| chr3 | 156,765,523 | 156,765,525 | PLCH1 | uc003faj.2 | Stop | G | A | Q | * | - | 24N | 75.00 | 24T | 1.10 | somatic mutation |
| chr4 | 74,494,904 | 74,494,906 | ALB | uc003hqs.2 | Nonsynonymous | C | T | R | W | + | 55N | 93.00 | 55T | 1.11 | somatic mutation |
| chr16 | 49,728,824 | 49,728,826 | SALL1 | uc002egt.2 | Nonsynonymous | G | A | S | L | - | 96N | 0.73 | 96T | 1.22 | somatic mutation |
| chr19 | 61,061,642 | 61,061,644 | NLRP4 | uc010etf.1 | Nonsynonymous | C | A | G | R | + | 60N | 70.00 | 60T | 1.26 | somatic mutation |
| chr22 | 35,659,934 | 35,659,936 | CSF2RB | uc003aqc.2 | Nonsynonymous | G | A | G | E | + | 55N | 24.00 | 55T | 1.27 | somatic mutation |
| chr6 | 74,381,779 | 74,381,781 | SLC17A5 | uc003bhn.2 | Nonsynonymous | G | A | E | C | - | 18N | 56.00 | 18T | 1.27 | somatic mutation |
| chr7 | 140,099,604 | 140,099,606 | BRAF | uc003vwc.2 | Nonsynonymous | A | T | V | E | - | 35N | 0.72 | 35T | 1.30 | somatic mutation |
| chr15 | 80,362,092 | 80,362,094 | FAM154B | uc002bgv.1 | Nonsynonymous | C | A | P | S | + | 55N | 70.00 | 55T | 1.31 | somatic mutation |
| chr16 | 49,731,238 | 49,731,240 | SALL1 | uc002egt.2 | Nonsynonymous | G | A | P | S | - | 55N | 33.00 | 55T | 1.33 | somatic mutation |
| chr22 | 35,659,934 | 35,659,936 | CSF2RB | uc003aqc.2 | Nonsynonymous | G | A | G | E | + | 09N | 0.83 | 09T | 1.33 | somatic mutation |
| chr20 | 57,262,579 | 57,262,581 | ZNF831 | uc002yan.1 | Nonsynonymous | C | T | S | F | + | 43N | 0.70 | 43T | 1.34 | somatic mutation |
| chr4 | 176,135,052 | 176,135,054 | ADAM29 | uc003jud.1 | Nonsynonymous | G | A | G | E | + | 55N | 93.00 | 55T | 1.43 | somatic mutation |
| chr15 | 80,362,092 | 80,362,094 | FAM154B | uc002bgv.1 | Nonsynonymous | C | T | P | S | + | 12N | 67.00 | 12T | 1.43 | somatic mutation |
| chr12 | 109,796,101 | 109,796,103 | CCDC63 | uc001trv.1 | Nonsynonymous | G | A | R | Q | + | 93N | 93.00 | 93T | 1.45 | somatic mutation |
| chr20 | 57,262,579 | 57,262,581 | ZNF831 | uc002yan.1 | Nonsynonymous | G | A | S | F | + | 91N | 0.70 | 91T | 1.46 | somatic mutation |
| chr16 | 49,730,517 | 49,730,519 | SALL1 | uc002egt.2 | Nonsynonymous | G | A | S | F | - | 24N | 41.00 | 24T | 1.50 | somatic mutation |
| chr20 | 9,267,562 | 9,267,564 | PLCB4 | uc010gbx.1 | Nonsynonymous | T | C | L | P | + | 12N | 93.00 | 12T | 1.52 | somatic mutation |
| chr16 | 49,732,618 | 49,732,620 | SALL1 | uc002egt.2 | Nonsynonymous | G | A | P | S | - | 60N | 93.00 | 60T | 1.52 | somatic mutation |
| chr18 | 48,532,493 | 48,532,495 | DCC | uc002fe.1 | Nonsynonymous | G | A | G | E | + | 18N | 55.00 | 18T | 1.54 | somatic mutation |
| chr7 | 110,551,147 | 110,551,149 | LRRN3 | uc001wm.1 | Nonsynonymous | G | A | E | K | + | 12N | 0.70 | 12T | 1.55 | somatic mutation |
| chr12 | 116,182,707 | 116,182,709 | NOS1 | uc001wm.1 | Nonsynonymous | G | A | S | L | - | 60N | 0.70 | 60T | 1.56 | somatic mutation |
| chr19 | 61,061,426 | 61,061,428 | NLRP4 | uc010etf.1 | Nonsynonymous | C | T | S | F | + | 55N | 88.00 | 55T | 1.57 | somatic mutation |
| chr7 | 98,347,737 | 98,347,739 | TRRAP | uc003upp.1 | Nonsynonymous | C | T | S | F | + | 91N | 0.70 | 91T | 1.57 | somatic mutation |
| chr19 | 61,060,943 | 61,060,945 | NLRP4 | uc002qme.1 | Nonsynonymous | G | A | E | K | + | 55N | 93.00 | 55T | 1.59 | somatic mutation |
| chr3 | 422,211 | 422,213 | CHL1 | uc003bou.1 | Nonsynonymous | C | T | R | W | + | 18N | 93.00 | 18T | 1.60 | somatic mutation |
| chr1 | 20,871,077 | 20,871,079 | KIF17 | uc001bdr.2 | Nonsynonymous | C | T | E | K | - | 55N | 30.00 | 55T | 1.63 | somatic mutation |
| chr3 | 156,765,523 | 156,765,525 | PLCH1 | uc003faj.2 | Stop | G | A | Q | * | - | 01N | 0.72 | 01T | 1.63 | somatic mutation |
| chr6 | 74,381,779 | 74,381,781 | SLC17A5 | uc003bhn.2 | Nonsynonymous | G | A | R | C | - | 12N | 52.00 | 12T | 1.65 | somatic mutation |
| chr12 | 109,826,797 | 109,826,799 | CCDC63 | uc001trv.1 | Nonsynonymous | G | A | D | N | + | 01N | 0.71 | 01T | 1.74 | somatic mutation |
| chr7 | 110,551,147 | 110,551,149 | LRRN3 | uc010lis.1 | Nonsynonymous | G | A | E | K | + | 24N | 59.00 | 24T | 1.74 | somatic mutation |

FIG. 9B

| Chr | LeftFlank | RightFlank | Refseq | Transcript | Type of mutation | Ref_allele | Var_allele | Ref_aa | Var_aa | Strand | Normal name | Normal MPG/coverage | Tumor name | Tumor MPG/coverage | Sanger evaluation |
|---|---|---|---|---|---|---|---|---|---|---|---|---|---|---|---|
| chr14 | 31,631,090 | 31,631,092 | ARHGAP5 | uc001wrn.1 | Nonsynonymous | G | A | E | K | + | 91N | 0.78 | 91T | 0.03 | no mutation |
| chr5 | 115,266,568 | 115,266,570 | AP3S1 | uc003krl.1 | Nonsynonymous | A | G | N | S | + | 96N | 0.16 | 96T | 0.04 | no mutation |
| chr14 | 31,631,090 | 31,631,092 | ARHGAP5 | uc001wrn.1 | Nonsynonymous | G | A | E | K | + | 35N | 0.30 | 35T | 0.07 | no mutation |
| chr10 | 42,635,809 | 42,635,811 | BMS1 | uc001iai.1 | Nonsynonymous | T | A | F | I | + | 18N | 0.45 | 18T | 0.09 | no mutation |
| chr1 | 21,667,865 | 21,667,867 | NBPF3 | uc001ber.1 | Nonsynonymous | A | C | K | Q | + | 96N | 0.51 | 96T | 0.10 | no mutation |
| chrX | 135,785,355 | 135,785,357 | RBMX | uc004fag.1 | Nonsynonymous | A | G | L | P | - | 43N | 0.19 | 43T | 0.16 | no mutation |
| chr1 | 21,667,865 | 21,667,867 | NBPF3 | uc001ber.1 | Nonsynonymous | A | C | K | Q | + | 12N | 59.00 | 12T | 0.20 | no mutation |
| chr5 | 115,266,568 | 115,266,570 | AP3S1 | uc003krl.1 | Nonsynonymous | A | G | N | S | + | 22N | 0.15 | 22T | 0.23 | no mutation |
| chr2 | 148,392,613 | 148,392,615 | ACVR2A | uc002iwh.1 | Nonsynonymous | A | C | K | N | + | 43N | 0.50 | 43T | 0.27 | no mutation |
| chr6 | 57,123,638 | 57,123,640 | ZNF451 | uc003pdk.1 | Nonsynonymous | C | A | N | K | + | 22N | 16.00 | 22T | 0.28 | no mutation |
| chr11 | 122,437,096 | 122,437,098 | HSPA8 | uc001pyp.1 | Nonsynonymous | C | T | R | Q | - | 60N | 0.49 | 60T | 0.28 | no mutation |
| chr5 | 115,266,568 | 115,266,570 | AP3S1 | uc003krl.1 | Nonsynonymous | A | G | N | S | + | 91N | 0.37 | 91T | 0.28 | no mutation |
| chrX | 24,716,973 | 24,716,975 | EEF1B2 | uc010nga.1 | Stop | A | G | L | * | - | 51N | 0.38 | 51T | 0.28 | no mutation |
| chr11 | 122,437,121 | 122,437,123 | HSPA8 | uc001pyp.1 | Nonsynonymous | A | C | Y | * | - | 60N | 0.37 | 60T | 0.29 | no mutation |
| chr11 | 122,437,121 | 122,437,123 | HSPA8 | uc001pyp.1 | Nonsynonymous | A | G | Y | H | - | 60N | 0.37 | 60T | 0.30 | no mutation |
| chr11 | 122,437,100 | 122,437,102 | HSPA8 | uc001pyp.1 | Nonsynonymous | C | T | E | K | - | 60N | 0.48 | 60T | 0.30 | no mutation |
| chr1 | 89,221,455 | 89,221,457 | CCBL2 | uc009wcx.1 | Stop | A | T | Y | * | - | 22N | 0.45 | 22T | 0.32 | no mutation |
| chr1 | 89,221,455 | 89,221,457 | CCBL2 | uc009wcx.1 | Stop | A | T | Y | * | - | 96N | 0.23 | 96T | 0.33 | no mutation |
| chrX | 135,785,355 | 135,785,357 | RBMX | uc004fag.1 | Nonsynonymous | A | G | L | P | - | 91N | 0.08 | 91T | 0.33 | no mutation |
| chr6 | 126,668,230 | 126,668,232 | CTBP2 | uc001lld.2 | Nonsynonymous | G | C | A | G | - | 51N | 0.55 | 51T | 0.34 | no mutation |
| chr10 | 42,635,809 | 42,635,811 | BMS1 | uc001iai.1 | Stop | T | A | F | I | + | 43N | 0.39 | 43T | 0.38 | no mutation |
| chr2 | 148,392,613 | 148,392,615 | ACVR2A | uc002iwh.1 | Nonsynonymous | A | C | K | N | + | 18N | 0.34 | 18T | 0.41 | no mutation |
| chr11 | 122,437,096 | 122,437,098 | HSPA8 | uc001pyp.1 | Nonsynonymous | C | T | R | Q | - | 43N | 0.60 | 43T | 0.42 | no mutation |
| chrX | 24,716,980 | 24,716,982 | EEF1B2 | uc010nga.1 | Nonsynonymous | T | C | S | G | - | 51N | 0.11 | 51T | 0.43 | no mutation |
| chr8 | 101,786,342 | 101,786,344 | PABPC1 | uc003vjs.1 | Nonsynonymous | G | A | S | L | - | 91N | 0.45 | 91T | 0.44 | no mutation |
| chrX | 135,784,240 | 135,784,242 | RBMX | uc004fag.1 | Nonsynonymous | G | A | P | L | - | 91N | 0.17 | 91T | 0.44 | no mutation |
| chr5 | 115,266,568 | 115,266,570 | AP3S1 | uc003krl.1 | Nonsynonymous | A | G | N | S | + | 12N | 0.52 | 12T | 0.46 | no mutation |
| chr13 | 24,569,368 | 24,569,370 | PABPC3 | uc001upy.1 | Stop | T | A | L | * | + | 09N | 0.36 | 09T | 0.47 | no mutation |
| chr11 | 122,437,100 | 122,437,102 | HSPA8 | uc001pyp.1 | Nonsynonymous | C | T | E | K | - | 43N | 0.60 | 43T | 0.47 | no mutation |
| chr8 | 101,786,342 | 101,786,344 | PABPC1 | uc003vjs.1 | Nonsynonymous | G | A | S | L | - | 5N | 0.13 | 5T | 0.48 | no mutation |
| chr11 | 122,437,121 | 122,437,123 | HSPA8 | uc001pyp.1 | Nonsynonymous | A | C | Y | * | - | 43N | 0.40 | 43T | 0.49 | no mutation |
| chr11 | 122,437,121 | 122,437,123 | HSPA8 | uc001pyp.1 | Nonsynonymous | A | G | Y | H | - | 43N | 0.40 | 43T | 0.50 | no mutation |
| chr14 | 31,631,090 | 31,631,092 | ARHGAP5 | uc001wrn.1 | Nonsynonymous | G | A | E | K | + | 12N | 0.12 | 12T | 0.52 | no mutation |
| chr10 | 126,668,230 | 126,668,232 | CTBP2 | uc001lsb.1 | Nonsynonymous | G | C | A | G | - | 12N | 0.47 | 12T | 0.63 | no mutation |
| chr14 | 31,631,090 | 31,631,092 | ARHGAP5 | uc001wrn.1 | Nonsynonymous | G | C | E | K | + | 91N | 0.53 | 91T | 0.65 | no mutation |
| chrX | 24,913,592 | 24,913,594 | ARHGAP21 | uc001isb.1 | Nonsynonymous | G | C | P | L | - | 43N | 0.32 | 43T | 0.67 | no mutation |
| chr2 | 148,392,613 | 148,392,615 | ACVR2A | uc002iwh.1 | Nonsynonymous | A | C | K | N | + | 96N | 0.22 | 96T | 0.84 | no mutation |
| chr13 | 73,719,665 | 73,719,667 | AK123088 | uc004ebu.1 | Splice-site | G | A | NA | NA | + | 55N | 0.37 | 55T | 0.68 | no mutation |
| chrX | 135,784,240 | 135,784,242 | RBMX | uc004fag.1 | Nonsynonymous | G | A | E | K | - | 5N | 0.79 | 5T | 0.70 | no mutation |
| chr14 | 31,631,090 | 31,631,092 | ARHGAP5 | uc001wrn.1 | Nonsynonymous | G | A | E | K | + | 01N | 0.52 | 01T | 0.72 | no mutation |
| chr10 | 126,668,230 | 126,668,232 | CTBP2 | uc001lsb.1 | Nonsynonymous | G | C | A | G | - | 91N | 0.53 | 91T | 0.65 | no mutation |
| chrX | 24,913,592 | 24,913,594 | ARHGAP21 | uc001isb.1 | Nonsynonymous | G | C | P | L | - | 96N | 0.22 | 96T | 0.84 | no mutation |
| chr2 | 148,392,613 | 148,392,615 | ACVR2A | uc002iwh.1 | Nonsynonymous | A | C | K | N | + | 51N | 0.42 | 51T | 0.92 | no mutation |
| chrX | 73,719,665 | 73,719,667 | AK123088 | uc004ebu.1 | Nonsynonymous | G | A | NA | L | - | 24N | 3.34 | 24T | 1.00 | no mutation |
| chrX | 135,784,240 | 135,784,242 | RBMX | uc004ebu.1 | Splice-site | G | A | NA | NA | - | 91N | 0.33 | 91T | 1.13 | no mutation |
| chr6 | 57,123,638 | 57,123,640 | ZNF451 | uc003pdk.1 | Nonsynonymous | C | A | N | K | + | 24N | 0.39 | 24T | 1.44 | no mutation |

Based on genome build hg18 (NCBI 36.1).

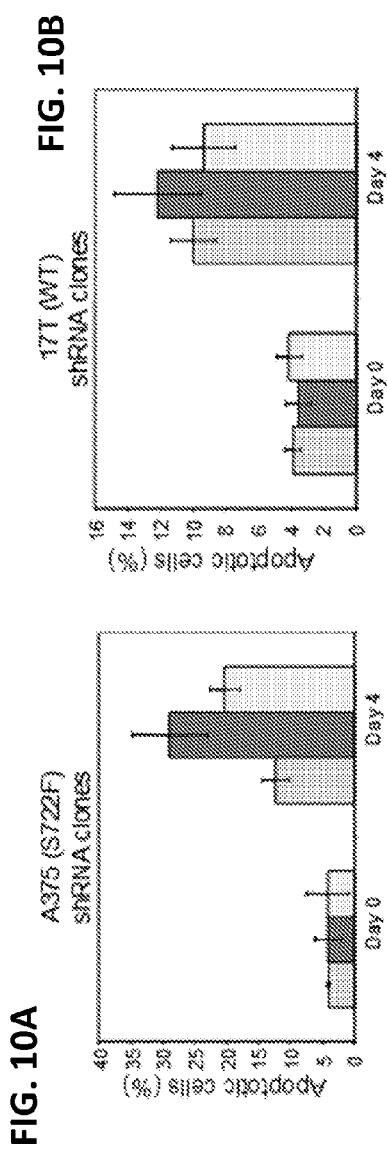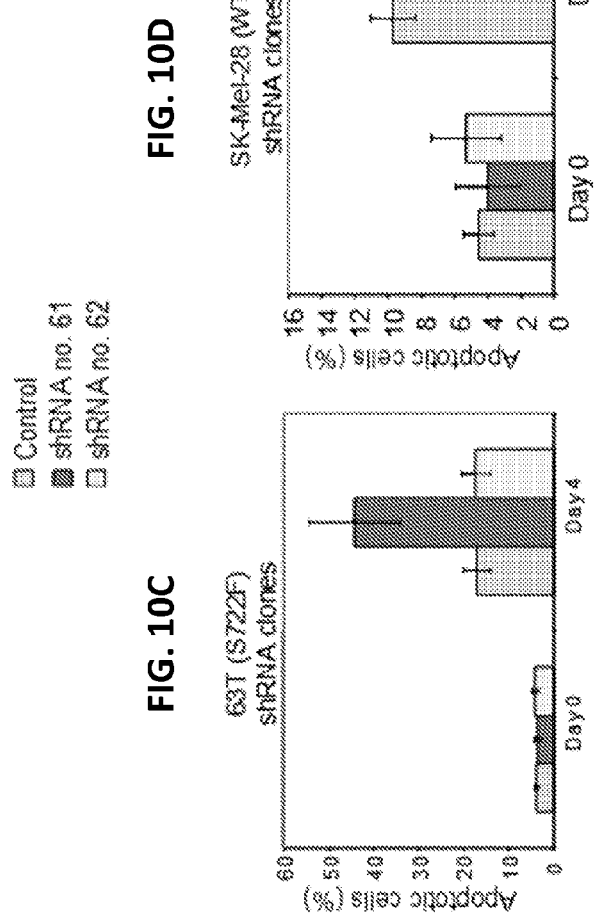

FIG. 12A
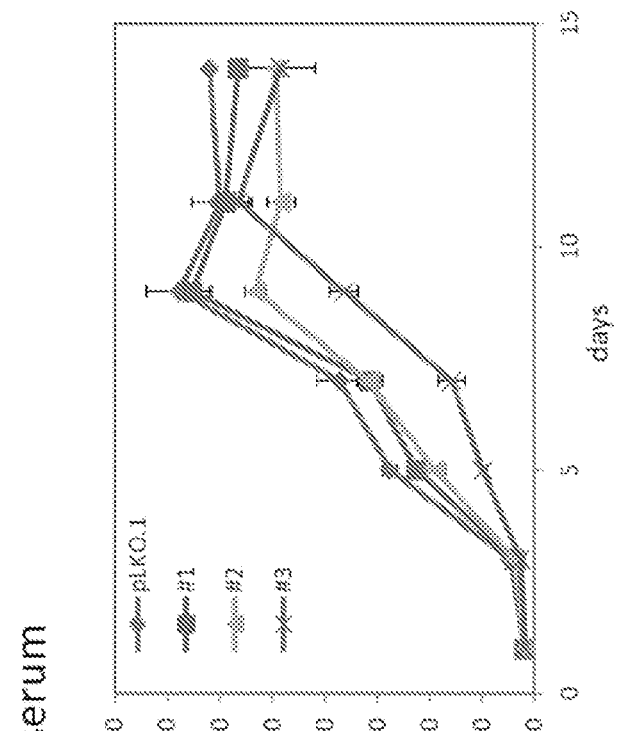
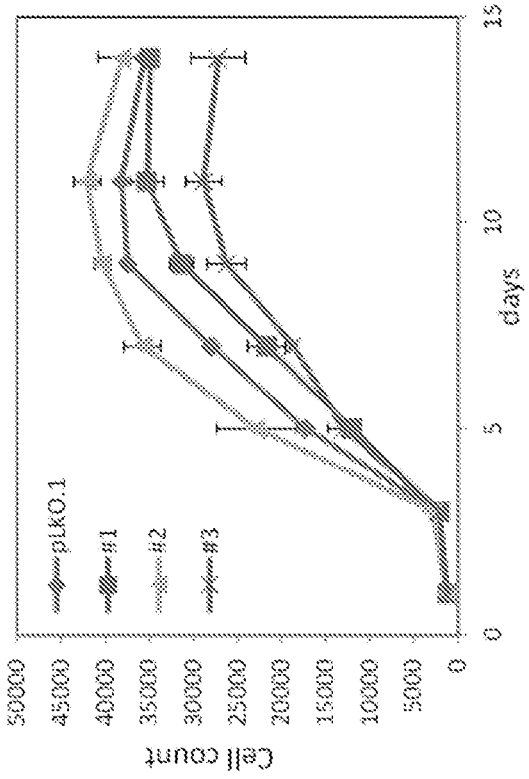

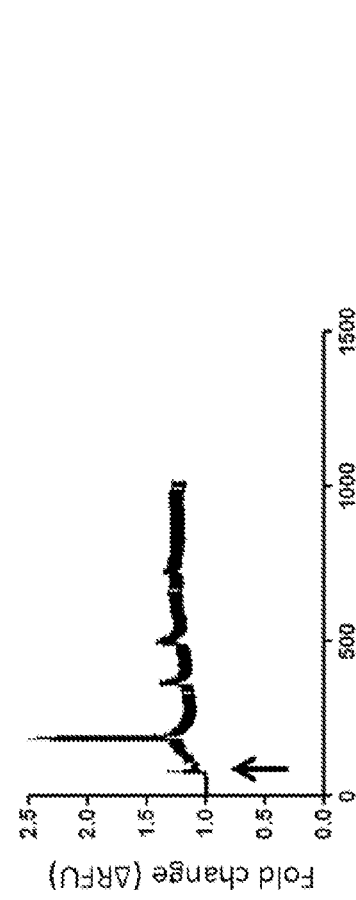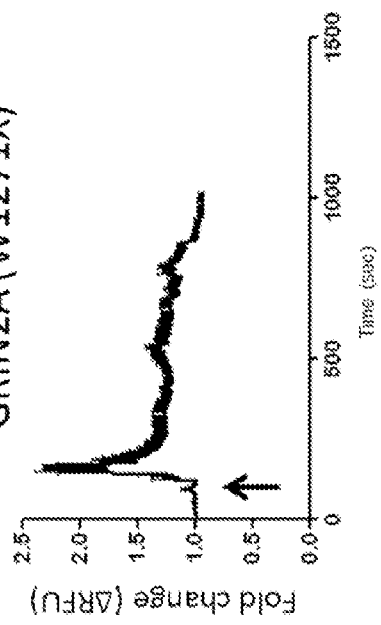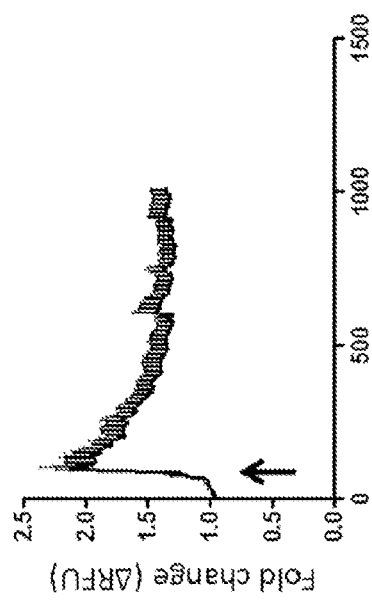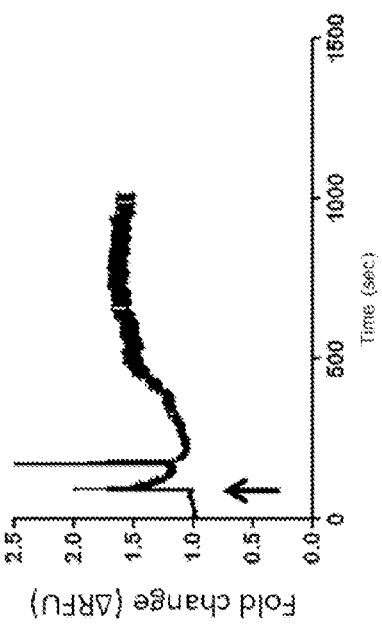
FIG. 13A

```
                     SEQUENCE LISTING

<160> NUMBER OF SEQ ID NOS: 72

<210> SEQ ID NO 1
<211> LENGTH: 11493
<212> TYPE: DNA
<213> ORGANISM: Homo sapiens

<400> SEQUENCE: 1
atggcgtttg  ttgcaacaca  gggggccacg  gtggttgacc  agaccacttt  gatgaaaaag    60
taccttcagt  ttgtggcagc  tctcacagat  gtgaatacac  ctgatgaaac  aaagttgaaa   120
atgatgcaag  aagttagtga  aaattttgag  aatgtcacgt  catctcctca  gtattctaca   180
ttcctagaac  atatcatccc  tcgattcctt  acatttctcc  aagatggaga  agttcagttt   240
cttcaggaga  accagcaca   gcaactgcgg  aagctcgtac  ttgaaataat  tcatagaata   300
ccaaccaacg  aacatcttcg  tcctcacaca  aaaaatgttt  tgtctgtgat  gtttcgcttt   360
ttagagacgg  aaaatgaaga  aaatgttctt  atttgtctaa  gaataattat  tgagctacac   420
aaacagttca  ggccaccgat  cacacaagaa  attcatcatt  ttctggattt  tgtgaaacag   480
atttacaagg  agcttccaaa  agtagtgaac  cgctactttg  agaaccctca  agtgatcccc   540
gagaacacag  tgcctccccc  agaaatggtt  ggtatgataa  caacgattgc  tgtgaaagtc   600
```

```
aacccggagc gtgaggacag tgagactcga acacattcca tcattccgag gggatcactt    660
tctctgaaag tgttggcaga attgccatt  attgttgttt taatgtatca gctctacaaa    720
ctgaacatcc acaatgttgt tgctgagttt gtgcccttga tcatgaacac cattgccatt    780
caggtgtctg cacaagcgag gcaacataag ctttacaaca aggagttgta tgctgacttc    840
attgctgctc agattaaaac attgtcattt ttagcttaca ttatcaggat ttaccaggag    900
ttggtgacta agtattctca gcagatggtg aaaggaatgc tccagttact ttcaaattgt    960
ccagcagaga ctgcacacct cagaaaggag cttctgattg ctgccaaaca catcctcacc   1020
acagagctga gaaaccagtt cattccttgc atggacaagc tgtttgatga atccatacta   1080
attggctcag gatatactgc cagagagact ctaaggcccc tcgcctacag cacgctggcc   1140
gacctcgtgc accatgtccg ccagcacctg cccctcagcg acctctccct cgccgtccag   1200
ctcttcgcca agaacatcga cgatgagtcc ctgcccagca gcatccagac catgtcctgc   1260
aagctcctgc tgaacctggt ggactgcatc cgttccaaga gcgagcagga gagtggcaat   1320
gggagagacg tcctgatgcg gatgctggag gttttcgttc tcaaattcca cacaattgct   1380
cggtaccagc tctctgccat ttttaagaag tgtaagcctc agtcagaact tggagccgtg   1440
gaagcagctc tgcctggggt gcccactgcc cctgcagctc ctggccctgc tccctcccca   1500
gcccctgtcc ctgccccacc tccacccccg cccccacccc cacctgccac ccctgtgacc   1560
ccggcccccg tgcctccctt cgagaagcaa ggagaaaagg acaaggaaga caagcagaca   1620
ttccaagtca cagactgtcg aagtttggtc aaaaccttgg tgtgtggtgt caagacaatc   1680
acgtggggca taacatcatg caaagcacct ggtgaagctc agttcattcc caacaagcag   1740
ttacaaccca agagacaca  gatttacatc aaacttgtga atatgcaat  gcaagcttta   1800 gatatttatc aggtccagat agcaggaaat ggacagacat acatccgtgt ggccaactgc   1860
cagactgtga gaatgaaaga ggagaaggag gtattggagc atttcgctgg tgtgttcaca   1920
atgatgaacc ccttaacgtt caaagaaatc ttccaaacta cggtccctta tatggtggag   1980
agaatctcaa aaaattatgc tcttcagatt gttgccaatt ccttcttggc aaatcctact   2040
acctctgctc tgtttgctac gattctggtg gaatatctcc ttgatcgcct gccagaaatg   2100
ggctccaacg tggagctctc caacctgtac ctcaagctgt tcaagctggt cttggctct    2160 gtctccctct tgcagctga  aaatgaacaa atgctgaagc ctcacttgca caagattgtg   2220
aacagctcta tggagctcgc gcagactgcc aaggaaccct acaactactt cttgctgcta   2280
cgggcgctgt ttcgctctat tggtggaggt agccacgatc tcttgtatca ggagttcttg   2340
cctctccttc caaacctcct gcaagggctg aacatgcttc agagtggcct gcacaagcag   2400
cacatgaagg acctctttgt ggagctgtgt ctcaccgtcc ctgtgcggct gagctcgctt   2460
ttgccgtacc tgcccatgct tatggatccc ttggtgtctg cactcaatgg gtctcagaca   2520
ttggtcagcc aaggcctcag gacgctggag ctgtgtgtgg acaacctgca gcccgacttc   2580
ctctacgacc acatccagcc ggtgcgcgca gagctcatgc aggctctgtg gcgcaccttc   2640
cgcaaccctg ctgacagcat ctcccacgtg gcctaccgtg tgctcggtaa gtttggcggc   2700
agtaacagga gatgctgaa  ggagtcgcag aagctgcact acgttgtgac cgaggttcag   2760
ggccccagca tcactgtgga gttttccgac tgcaaagctt ctctccagct ccccatggag   2820
aaggccattg aaactgctct ggactgcctg aaaagcgcca acactgagcc ctactaccgg   2880
aggcaggcgt gggaagtgat caaatgcttc ctggtggcca tgatgagcct ggaggacaac   2940
aagcacgcac tctaccagct cctggcacac cccaacttta cagaaaagac catccccaat   3000
```

```
gttatcatct cacatcgcta caaagcccag acactccag cccggaagac ttttgagcag      3060
gccctgacag gcgccttcat gtctgctgtc attaaggacc tgcggccag cgccctgccc      3120 tttgtcgcca gcttgatccg ccactatacg atggtggcag tcgcccagca gtgtggccct     3180
ttcttgctgc cttgctacca ggtgggcagc cagcccagca cagccatgtt tcacagtgaa     3240
gaaaatggct cgaaaggaat ggatcctttg gttctcattg atgcaattgc tatttgtatg     3300
gcatatgaag aaaaggagct ttgcaaaatc ggggaggtgg ccctagctgt gatatttgat     3360
gttgcaagta tcatcctggg ctccaaggag agggcctgcc agctgcccct gttttcttac     3420
atcgtggagc gcctgtgtgc atgttgttat gaacaggcgt ggtatgcaaa gctgggggt      3480 gtggtgtcta ttaagtttct catggagcgg ctgcctctca cttgggttct ccagaaccag     3540
cagacattcc tgaaagcact tctctttgtc atgatggact taactgggaga ggtttccaat    3600 ggggcagtcg ctatggcaaa gaccacgctg gagcagcttc tgatgcggtg cgcaacgcct    3660
ttaaaagacg aggagagagc cgaagagatc gtggccgccc aggaaaagtc tttccaccat    3720
gtgacacacg acttggttcg agaagtcacc tctccaaact ccactgtgag gaagcaggcc    3780
atgcattcgc tgcaggtgtt ggcccaggtc actgggaaga gtgtcacggt gatcatggaa    3840
ccccacaaag aggtcctgca ggatatggtc cccctaaga agcacctgct ccgacaccag      3900
cctgccaacg cacagattgg cctgatggag gggaacacgt tctgtaccac gttgcagccc    3960
aggctcttca caatggaccct taacgtggtg gagcataagg tgttctacac agagctgttg    4020
aatttgtgtg aggctgaaga ttcagcttta acaaagctgc cctgttataa agccttccg      4080 tcactcgtac ctttacgaat tgcggcatta aatgcacttg ctgcctgcaa ttaccttcct    4140
cagtccaggg agaaaatcat cgctgcactc ttcaaagccc tgaattccac caatagtgag   4200
ctccaagagg ccggagaagc ctgtatgaga aagtttttag aaggtgctac catagaagtc   4260
gatcaaatcc acacacatat gcgacctttg ctgatgatgc tgggagatta ccggagcttg   4320
acgctgaatg ttgtgaatcg cctgacttcg gtcacgaggc tcttcccaaa ttccttcaat   4380
gataaatttt gtgatcagat gatgcaacat ctgcgcaagt ggatggaagt ggtggtgatc   4440
acccacaaag ggggccagag gagcgacgga aacgaaatga agatttgctc agcaattata   4500 aaccttttc atctgatccc ggctgctcct cagacactgg tgaagccttt gctagaggtt    4560
gtcatgaaaa cggagcgggc gatgctgatc gaggcgggga gtccattccg agagcccctg   4620
atcaagttcc tgactcgaca tccctcgcag acagtggagc tgttcatgat ggaagccaca   4680
ctgaacgatc cccagtggag cagaatgttt atgagttttt aaaacacaa agacgccaga    4740 cctctgcggg atgtgctggc tgccaacccc aacaggttca tcaccctgct gctgccgggg   4800
ggtgcccaga cggctgtgcg ccccggttcg cccagcacca gcaccatgcg cctggacctc   4860
cagttccagg ccatcaagat cataagcatt atagtgaaaa acgatgactc ctggctggcc   4920
agccagcact ctctggtgag ccagttgcga cgtgtgtggg tgagtgagaa cttccaagag   4980
aggcaccgca aggagaacat ggcagccacc aactggaagg agcccaagct gctggcctac   5040
tgcctgctga actactgcaa aaggaattac ggagatatag aattgctgtt ccagctgctc   5100
cgagccttta ctggtcgttt tctctgcaac atgcacattct taaaagagta tatggaggaa    5160
gagattccca aaaattacag catcgctcag aaacgtgccc tgttctttcg cttttgtagac  5220 ttcaacgacc ccaacttcgg agatgaatta aaagctaaag ttctgcagca tatcttgaat    5280
cctgctttct tgtacagctt tgagaagggg gaaggagagc agctcttggg acctcccaat    5340
```

```
ccagaaggag ataacccaga aagcatcacc agtgtgttta ttaccaaggt cctggacccc      5400
gagaagcagg cggacatgct ggactcgctg cggatctacc tgctgcagta cgccacgctg      5460
ctggtggagc acgccccca ccacatccat gacaacaaca agaaccgcaa cagcaagctg       5520
cgccgcctca tgaccttcgc ctggccctgc ctgctctcca aggcctgcgt ggacccagcc      5580
tgcaagtaca gcggacactt gctcctggcg cacattatcg ccaaattcgc catacacaag      5640
aagatcgtcc tgcaggtttt tcatagtctc ctcaaggctc acgcaatgga agctcgagcg      5700
atcgtcagac aggcgatggc cattctgacc ccggcggtgc cggccaggat ggaggacggg      5760
caccagatgc tgacccactg gacccggaag atcattgtgg aggaggggca caccgtcccg      5820
cagctggtcc acattctgca cctgatagtg caacacttca aggtgtacta cccggtacgg      5880
caccacttgg tgcagcacat ggtgagcgcc atgcagaggc tgggcttcac gcccagtgtc      5940
accatcgagc agaggcggct ggccgtggac ctgtctgaag tcgtcatcaa gtgggagctg      6000
cagaggatca aggaccagca gccggattca gatatggacc caaattccag tggagaagga      6060
gtcaattctg tctcatcctc cattaagaga ggcctgtccg tggattctgc caggaagtg       6120 aaacgcttta ggacggccac cggagccatc agtgcagtct ttgggaggag ccagtcgcta      6180
cctggagcag actctctcct cgccaagccc attgacaagc agcacacaga cactgtggtg      6240
aacttcctta tccgcgtggc ctgtcaggtt aatgacaaca ccaacacagc ggggtcccct      6300
ggggaggtgc tctctcgccg gtgtgtgaac ctttctgaaga ctgcgttgcg gccagacatg     6360
tggcccaagt ccgaactcaa gctgcagtgg ttcgacaagc tgctgatgac tgtggagcag      6420
ccaaaccaag tgaactatgg gaatatctgc acgggcctag aagtgctgag cttcctgcta      6480
actgtcctcc agtccccagc catcctcagt agcttcaaac ctctgcagcg tggaattgcc      6540
gcctgcatga catgtggaaa caccaaggtg ttgcgagccg tccacagcct tctctcgcgc      6600
ctgatgagca tttcccaac agagccgagt acttccagtg tggcctccaa atatgaagag       6660
ctggagtgcc tctacgcagc cgtcggaaag gtcatctatg aagggctcac caactacgag      6720
aaggccacca atgccaatcc ctcccagctc ttcgggaccc ttatgatcct caagtctgcc      6780
tgcagcaaca acccccagcta catagacagg ctgatctccg tctttatgcg ctccctgcag     6840
aagatggtcc gggagcattt aaaccctcag gcagcgtcag gaagcaccga agccacctca      6900
ggtacaagcg agctggtgat gctgagtctg gagctggtga agacgcgcct ggcagtgatg      6960
agcatggaga tgcggaagaa cttcatccag gccatcctga catccctcat cgaaaaatca      7020
ccagatgcca aaatcctccg ggctgtggtc aaaatcgtgg aagaatgggt caagaataac      7080
tccccaatgg cagccaatca gacacctaca ctccgggaga agtccatttt gcttgtgaag      7140
atgatgactt acatagaaaa acgctttccg gaagaccttg aattaaatgc ccagtttta       7200 gatcttgtta actatgtcta cagggatgag accctctctg gcagcgagct gacggcgaaa      7260
cttgagcctg cctttctctc tgggctgcgc tgtgcccagc cactcatcag ggcaaagttt      7320
ttcgaggttt ttgacaactc catgaaacgt cgtgtctacg agcgcttgct ctatgtgacc      7380
tgttcgcaga actgggaagc catggggaac cacttctgga tcaagcagtg cattgagctg      7440
cttctggccg tgtgtgagaa gagcaccccc attggcacca gctgccaagg agccatgctc      7500
ccgtccatca ccaacgtcat caacctggcc gatagccacg accgtgccgc cttcgccatg      7560
gtcacacatg tcaagcagga gccccgggag cgggagaaca gcgagtccaa agaggaggat      7620
gtagagatag acatcgaact agctcctggg gatcagacca gcacgcccaa aaccaaagaa      7680
cttttcagaa aggacattgg aaaccagctg cacatgctaa ccaacaggca cgacaagttt      7740
```

```
ctggacactc tccgagaggt gaagactgga gcgctgctca gcgctttcgt tcagctgtgc   7800
cacatttcca cgacgctggc agagaagacg tgggtccagc ttttccccag attgtggaag   7860
atcctctctg acagacagca gcatgcactc gcgggtgaga taagtccatt tctgtgcagc   7920
ggcagtcacc aggtgcagcg ggactgccag cccagcgcgc tgaactgctt tgtggaagcc   7980
atgtcccagt gcgtgccgcc aatccccatc cgaccctgcg tcctgaagta cctggggaag   8040
acacacaacc tctggttccg gtccacgctg atgttggagc accaggcttt tgaaaagggt   8100
ctgagtcttc agattaagcc gaagcaaaca acggagtttt atgagcagga gagcatcacc   8160
ccgccgcagc aggagatact ggattcccctt gcggagcttt actccctgtt acaagaggaa   8220
gatatgtggg ctggtctgtg gcagaagcgg tgcaagtact cggagacagc gactgcgatt   8280
gcttacgagc agcacggggtt ctttgagcag gcacaagaat cctatgaaaa ggcaatggat   8340
aaagccaaaa aagaacatga gaggagtaac gcctcccctg ctattttccc tgaataccag   8400
ctctgggaag accactggat tcgatgctcc aaggaattga accagtggga agccctgacg   8460
gagtacggtc agtccaaagg ccacatcaac ccctacctcg tcctggagtg cgcctggcgg   8520
gtgtccaact ggactgccat gaaggaggcg ctggtgcagg tggaagtgag ctgtccgaag   8580
gagatggcct ggaaggtgaa catgtaccgc ggatacctgg ccatctgcca ccccgaggag   8640
cagcagctca gcttcatcga gcgcctggtg gagatggcca gcagcctggc catccgcgag   8700
tggcggcggc tgccccacgt agtgtcccac gtgcacacgc tctcctaca ggcagcccag   8760
caaatcatcg aactccagga agctgcacaa atcaacgcag gcttacagcc aaccaacctg   8820
ggaaggaaca acagcctgca cgacatgaag acggtggtga gacctggag gaaccgactg   8880
cccatcgtgt ctgacgactt gtcccactgg agcagcatct tcatgtggag gcagcatcat   8940
taccaggcga ttgtaactgc ctatgagaat agctctcagc atgatcccag ttcaaataac   9000
gctatgcttg gggttcatgc atcagcttca gcgatcatcc agtatggaaa aatcgcccgg   9060
aaacaaggac tggtcaatgt agctctggat atattaagtc ggattcatac tattccaact   9120
gttcctatcg tggattgctt ccagaagatt cgacagcaag ttaaatgcta cctccagctg   9180
gcaggcgtca tgggcaaaaa cgagtgcatg cagggccttg aagttattga atctacaaat   9240
ttaaaatact tcacaaaaga gatgacagcc gaattttatg cactgaaggg aatgttcttg   9300
gctcagatca acaagtccga ggaggcaaac aaagccttct ctgcagctgt gcagatgcac   9360
gatgtgctgg tgaaagcctg gccatgtgg ggcgactacc tggagaacat ctttgtgaag   9420
gagcggcagc tgcaccctggg cgtgtctgcc atcacctgct acctgcacgc ctgccggcat   9480
cagaacgaga gcaaatcgag gaaatactta gccaaggtgc tgtggctttt gagttttgat   9540
gatgacaaaa acactttggc agatgccgtc gacaagtact gcattggtgt gccacccatc   9600
cagtggctgg cctggatccc acagctgctc acctgcctgg ttggctcgga gggaaagctg   9660
ctcttgaacc tcattagcca ggttggacgc gtgtatcccc aagcggtcta ctttcccatc   9720
cggaccctgt acctgaccct gaaaatagaa cagcgggaac gctacaagag cgatccaggg   9780
cccataagag caacagcacc catgtggcgc tgcagccgaa tcatgcacat gcagcgagag   9840
ctccaccccca cccttctgtc ttccctggaa ggcatcgtcg atcagatggt ctggttcaga   9900
gaaaattggc atgaagaggt tctcaggcag ctccaacagg gcctggcgaa atgttactcc   9960
gtggcgtttg agaaaagtgg agcggtgtcc gatgctaaaa tcacccccca cactctcaat   10020
tttgtgaaga agttggtgag cacgtttggg gtgggcctgg agaatgtgtc caacgtctcg   10080
```

```
accatgttct ccagcgcagc ctctgagtct ctggcccggc gggcgcaggc cactgcacaa      10140
gaccctgtct ttcagaagct gaaaggccag ttcacgacgg attttgactt cagcgttcca      10200
ggatccatga agcttcataa tcttatttct aagttgaaaa agtggatcaa atcttggag       10260
gccaagacca agcaactccc caaattcttc ctcatagagg aaaagtgccg gttcttgagc      10320
aatttctcgg cacagacagc tgaagtggaa attcctgggg agtttctgat gccaaagcca      10380
acgcattatt acatcaagat tgcacggttc atgccccggg tagagattgt gcagaagcac      10440
aacaccgcag cccggcggct gtacatccgg ggacacaatg gcaagatcta cccataccte      10500
gtcatgaacg acgcctgcct cacagagtca cggcgagagg agcgtgtgtt gcagctgctg      10560
cgtctgctga acccctgttt ggagaagaga aaggagacca ccaagaggca cttgtttttc      10620
acagtgcccc gggttgtggc agtttcccca cagatgcgcc tcgtggagga caacccctct      10680
tcactttccc ttgtggagat ctacaagcag cgctgcgcca agaagggcat cgagcatgac      10740
aaccccatct cccgttacta tgaccggctg gctacggtgc aggcgcgggg aacccaagcc      10800
agccaccagg tcctccgcga catcctcaag gaggttcaga gtaacatggt gccgcgcagc      10860
atgctcaagg agtgggcgct gcacaccttc cccaatgcca cggactactg gacgttccgg      10920
aagatgttca ccatccagct ggctctgata ggcttcgcgg aattcgtcct gcatttaaat      10980
agactcaacc ccgagatgtt acagatcgct caggacactg gcaaactgaa tgttgcctac      11040
tttcgatttg acataaacga cgcgactgga gacctggatg ccaaccgtcc tgtcccattt      11100
cgactcacgc ccaacatttc tgagtttctg accaccatcg gggtctccgg cccgttgaca      11160
gcgtccatga ttgcggtcgc ccggtgcttc gcccagccaa actttaaggt ggatggcatt      11220
ctgaaaacgg ttctccggga cgagatcatt gcttggcaca aaaaaacaca agaggacacg      11280
tcctctcctc tctcggccgc cgggcagcca gagaacatgg acagccagca actggtgtcc      11340
ctggttcaga aagccgtcac cgccatcatg acccgcctgc acaacctcgc ccagttcgaa      11400
ggcggggaaa gcaaggtgaa caccctggtg gccgcggcaa acagcctgga caatctgtgc      11460
cgcatggacc ccgcctggca cccctggctg tga                                  11493
```

<210> SEQ ID NO 2
<211> LENGTH: 3830
<212> TYPE: PRT
<213> ORGANISM: Homo sapiens

<400> SEQUENCE: 2

```
Met Ala Phe Val Ala Thr Gln Gly Ala Thr Val Asp Gln Thr Thr
1               5                   10                  15

Leu Met Lys Lys Tyr Leu Gln Phe Val Ala Ala Leu Thr Asp Val Asn
            20                  25                  30

Thr Pro Asp Glu Thr Lys Leu Lys Met Met Gln Glu Val Ser Glu Asn
        35                  40                  45

Phe Glu Asn Val Thr Ser Ser Pro Gln Tyr Ser Thr Phe Leu Glu His
    50                  55                  60

Ile Ile Pro Arg Phe Leu Thr Phe Leu Gln Asp Gly Glu Val Gln Phe
65                  70                  75                  80

Leu Gln Glu Lys Pro Ala Gln Gln Leu Arg Lys Leu Val Leu Glu Ile
                85                  90                  95

Ile His Arg Ile Pro Thr Asn Glu His Leu Arg Pro His Thr Lys Asn
            100                 105                 110

Val Leu Ser Val Met Phe Arg Phe Leu Glu Thr Glu Asn Glu Glu Asn
        115                 120                 125
```

```
Val Leu Ile Cys Leu Arg Ile Ile Glu Leu His Lys Gln Phe Arg
130                 135                 140

Pro Pro Ile Thr Gln Glu Ile His His Phe Leu Asp Phe Val Lys Gln
145                 150                 155                 160

Ile Tyr Lys Glu Leu Pro Lys Val Val Asn Arg Tyr Phe Glu Asn Pro
                165                 170                 175

Gln Val Ile Pro Glu Asn Thr Val Pro Pro Glu Met Val Gly Met
            180                 185                 190

Ile Thr Thr Ile Ala Val Lys Val Asn Pro Glu Arg Glu Asp Ser Glu
        195                 200                 205

Thr Arg Thr His Ser Ile Ile Pro Arg Gly Ser Leu Ser Leu Lys Val
210                 215                 220

Leu Ala Glu Leu Pro Ile Ile Val Val Leu Met Tyr Gln Leu Tyr Lys
225                 230                 235                 240

Leu Asn Ile His Asn Val Val Ala Glu Phe Val Pro Leu Ile Met Asn
                245                 250                 255

Thr Ile Ala Ile Gln Val Ser Ala Gln Ala Arg Gln His Lys Leu Tyr
            260                 265                 270

Asn Lys Glu Leu Tyr Ala Asp Phe Ile Ala Ala Gln Ile Lys Thr Leu
        275                 280                 285

Ser Phe Leu Ala Tyr Ile Ile Arg Ile Tyr Gln Glu Leu Val Thr Lys
290                 295                 300

Tyr Ser Gln Gln Met Val Lys Gly Met Leu Gln Leu Leu Ser Asn Cys
305                 310                 315                 320

Pro Ala Glu Thr Ala His Leu Arg Lys Glu Leu Leu Ile Ala Ala Lys
                325                 330                 335

His Ile Leu Thr Thr Glu Leu Arg Asn Gln Phe Ile Pro Cys Met Asp
            340                 345                 350

Lys Leu Phe Asp Glu Ser Ile Leu Ile Gly Ser Gly Tyr Thr Ala Arg
        355                 360                 365

Glu Thr Leu Arg Pro Leu Ala Tyr Ser Thr Leu Ala Asp Leu Val His
370                 375                 380

His Val Arg Gln His Leu Pro Leu Ser Asp Leu Ser Leu Ala Val Gln
385                 390                 395                 400

Leu Phe Ala Lys Asn Ile Asp Asp Glu Ser Leu Pro Ser Ser Ile Gln
                405                 410                 415

Thr Met Ser Cys Lys Leu Leu Leu Asn Leu Val Asp Cys Ile Arg Ser
            420                 425                 430

Lys Ser Glu Gln Glu Ser Gly Asn Gly Arg Asp Val Leu Met Arg Met
        435                 440                 445

Leu Glu Val Phe Val Leu Lys Phe His Thr Ile Ala Arg Tyr Gln Leu
450                 455                 460

Ser Ala Ile Phe Lys Lys Cys Lys Pro Gln Ser Glu Leu Gly Ala Val
465                 470                 475                 480

Glu Ala Ala Leu Pro Gly Val Pro Thr Ala Pro Ala Pro Gly Pro
                485                 490                 495

Ala Pro Ser Pro Ala Pro Val Pro Ala Pro Pro Pro Pro Pro
            500                 505                 510

Pro Pro Pro Ala Thr Pro Val Thr Pro Ala Pro Val Pro Pro Phe Glu
        515                 520                 525

Lys Gln Gly Glu Lys Asp Lys Glu Asp Lys Gln Thr Phe Gln Val Thr
530                 535                 540
```

-continued

```
Asp Cys Arg Ser Leu Val Lys Thr Leu Val Cys Gly Val Lys Thr Ile
545                 550                 555                 560

Thr Trp Gly Ile Thr Ser Cys Lys Ala Pro Gly Glu Ala Gln Phe Ile
                565                 570                 575

Pro Asn Lys Gln Leu Gln Pro Lys Glu Thr Gln Ile Tyr Ile Lys Leu
            580                 585                 590

Val Lys Tyr Ala Met Gln Ala Leu Asp Ile Tyr Gln Val Gln Ile Ala
        595                 600                 605

Gly Asn Gly Gln Thr Tyr Ile Arg Val Ala Asn Cys Gln Thr Val Arg
    610                 615                 620

Met Lys Glu Glu Lys Glu Val Leu Glu His Phe Ala Gly Val Phe Thr
625                 630                 635                 640

Met Met Asn Pro Leu Thr Phe Lys Glu Ile Phe Gln Thr Thr Val Pro
                645                 650                 655

Tyr Met Val Glu Arg Ile Ser Lys Asn Tyr Ala Leu Gln Ile Val Ala
            660                 665                 670

Asn Ser Phe Leu Ala Asn Pro Thr Thr Ser Ala Leu Phe Ala Thr Ile
        675                 680                 685

Leu Val Glu Tyr Leu Leu Asp Arg Leu Pro Glu Met Gly Ser Asn Val
    690                 695                 700

Glu Leu Ser Asn Leu Tyr Leu Lys Leu Phe Lys Leu Val Phe Gly Ser
705                 710                 715                 720

Val Ser Leu Phe Ala Ala Glu Asn Glu Gln Met Leu Lys Pro His Leu
                725                 730                 735

His Lys Ile Val Asn Ser Ser Met Glu Leu Ala Gln Thr Ala Lys Glu
            740                 745                 750

Pro Tyr Asn Tyr Phe Leu Leu Arg Ala Leu Phe Arg Ser Ile Gly
        755                 760                 765

Gly Gly Ser His Asp Leu Leu Tyr Gln Glu Phe Leu Pro Leu Leu Pro
    770                 775                 780

Asn Leu Leu Gln Gly Leu Asn Met Leu Gln Ser Gly Leu His Lys Gln
785                 790                 795                 800

His Met Lys Asp Leu Phe Val Glu Leu Cys Leu Thr Val Pro Val Arg
                805                 810                 815

Leu Ser Ser Leu Leu Pro Tyr Leu Pro Met Leu Met Asp Pro Leu Val
            820                 825                 830

Ser Ala Leu Asn Gly Ser Gln Thr Leu Val Ser Gln Gly Leu Arg Thr
        835                 840                 845

Leu Glu Leu Cys Val Asp Asn Leu Gln Pro Asp Phe Leu Tyr Asp His
850                 855                 860

Ile Gln Pro Val Arg Ala Glu Leu Met Gln Ala Leu Trp Arg Thr Leu
865                 870                 875                 880

Arg Asn Pro Ala Asp Ser Ile Ser His Val Ala Tyr Arg Val Leu Gly
                885                 890                 895

Lys Phe Gly Gly Ser Asn Arg Lys Met Leu Lys Glu Ser Gln Lys Leu
            900                 905                 910

His Tyr Val Val Thr Glu Val Gln Gly Pro Ser Ile Thr Val Glu Phe
        915                 920                 925

Ser Asp Cys Lys Ala Ser Leu Gln Leu Pro Met Glu Lys Ala Ile Glu
    930                 935                 940

Thr Ala Leu Asp Cys Leu Lys Ser Ala Asn Thr Glu Pro Tyr Tyr Arg
945                 950                 955                 960

Arg Gln Ala Trp Glu Val Ile Lys Cys Phe Leu Val Ala Met Met Ser
```

-continued

```
              965                 970                 975
Leu Glu Asp Asn Lys His Ala Leu Tyr Gln Leu Leu Ala His Pro Asn
            980                 985                 990

Phe Thr Glu Lys Thr Ile Pro Asn  Val Ile Ile Ser His  Arg Tyr Lys
            995                 1000                1005

Ala Gln Asp Thr Pro Ala Arg  Lys Thr Phe Glu Gln  Ala Leu Thr
           1010                1015                1020

Gly Ala Phe Met Ser Ala Val  Ile Lys Asp Leu Arg  Pro Ser Ala
           1025                1030                1035

Leu Pro Phe Val Ala Ser Leu  Ile Arg His Tyr Thr  Met Val Ala
           1040                1045                1050

Val Ala Gln Gln Cys Gly Pro  Phe Leu Leu Pro Cys  Tyr Gln Val
           1055                1060                1065

Gly Ser Gln Pro Ser Thr Ala  Met Phe His Ser Glu  Glu Asn Gly
           1070                1075                1080

Ser Lys Gly Met Asp Pro Leu  Val Leu Ile Asp Ala  Ile Ala Ile
           1085                1090                1095

Cys Met Ala Tyr Glu Glu Lys  Glu Leu Cys Lys Ile  Gly Glu Val
           1100                1105                1110

Ala Leu Ala Val Ile Phe Asp  Val Ala Ser Ile Ile  Leu Gly Ser
           1115                1120                1125

Lys Glu Arg Ala Cys Gln Leu  Pro Leu Phe Ser Tyr  Ile Val Glu
           1130                1135                1140

Arg Leu Cys Ala Cys Cys Tyr  Glu Gln Ala Trp Tyr  Ala Lys Leu
           1145                1150                1155

Gly Gly Val Val Ser Ile Lys  Phe Leu Met Glu Arg  Leu Pro Leu
           1160                1165                1170

Thr Trp Val Leu Gln Asn Gln  Gln Thr Phe Leu Lys  Ala Leu Leu
           1175                1180                1185

Phe Val Met Met Asp Leu Thr  Gly Glu Val Ser Asn  Gly Ala Val
           1190                1195                1200

Ala Met Ala Lys Thr Thr Leu  Glu Gln Leu Leu Met  Arg Cys Ala
           1205                1210                1215

Thr Pro Leu Lys Asp Glu Glu  Arg Ala Glu Glu Ile  Val Ala Ala
           1220                1225                1230

Gln Glu Lys Ser Phe His His  Val Thr His Asp Leu  Val Arg Glu
           1235                1240                1245

Val Thr Ser Pro Asn Ser Thr  Val Arg Lys Gln Ala  Met His Ser
           1250                1255                1260

Leu Gln Val Leu Ala Gln Val  Thr Gly Lys Ser Val  Thr Val Ile
           1265                1270                1275

Met Glu Pro His Lys Glu Val  Leu Gln Asp Met Val  Pro Pro Lys
           1280                1285                1290

Lys His Leu Leu Arg His Gln  Pro Ala Asn Ala Gln  Ile Gly Leu
           1295                1300                1305

Met Glu Gly Asn Thr Phe Cys  Thr Thr Leu Gln Pro  Arg Leu Phe
           1310                1315                1320

Thr Met Asp Leu Asn Val Val  Glu His Lys Val Phe  Tyr Thr Glu
           1325                1330                1335

Leu Leu Asn Leu Cys Glu Ala  Glu Asp Ser Ala Leu  Thr Lys Leu
           1340                1345                1350

Pro Cys Tyr Lys Ser Leu Pro  Ser Leu Val Pro Leu  Arg Ile Ala
           1355                1360                1365
```

-continued

```
Ala Leu Asn Ala Leu Ala Ala Cys Asn Tyr Leu Pro Gln Ser Arg
    1370            1375                1380

Glu Lys Ile Ile Ala Ala Leu Phe Lys Ala Leu Asn Ser Thr Asn
    1385            1390                1395

Ser Glu Leu Gln Glu Ala Gly Glu Ala Cys Met Arg Lys Phe Leu
    1400            1405                1410

Glu Gly Ala Thr Ile Glu Val Asp Gln Ile His Thr His Met Arg
    1415            1420                1425

Pro Leu Leu Met Met Leu Gly Asp Tyr Arg Ser Leu Thr Leu Asn
    1430            1435                1440

Val Val Asn Arg Leu Thr Ser Val Thr Arg Leu Phe Pro Asn Ser
    1445            1450                1455

Phe Asn Asp Lys Phe Cys Asp Gln Met Met Gln His Leu Arg Lys
    1460            1465                1470

Trp Met Glu Val Val Val Ile Thr His Lys Gly Gly Gln Arg Ser
    1475            1480                1485

Asp Gly Asn Glu Met Lys Ile Cys Ser Ala Ile Ile Asn Leu Phe
    1490            1495                1500

His Leu Ile Pro Ala Ala Pro Gln Thr Leu Val Lys Pro Leu Leu
    1505            1510                1515

Glu Val Val Met Lys Thr Glu Arg Ala Met Leu Ile Glu Ala Gly
    1520            1525                1530

Ser Pro Phe Arg Glu Pro Leu Ile Lys Phe Leu Thr Arg His Pro
    1535            1540                1545

Ser Gln Thr Val Glu Leu Phe Met Met Glu Ala Thr Leu Asn Asp
    1550            1555                1560

Pro Gln Trp Ser Arg Met Phe Met Ser Phe Leu Lys His Lys Asp
    1565            1570                1575

Ala Arg Pro Leu Arg Asp Val Leu Ala Ala Asn Pro Asn Arg Phe
    1580            1585                1590

Ile Thr Leu Leu Leu Pro Gly Gly Ala Gln Thr Ala Val Arg Pro
    1595            1600                1605

Gly Ser Pro Ser Thr Ser Thr Met Arg Leu Asp Leu Gln Phe Gln
    1610            1615                1620

Ala Ile Lys Ile Ile Ser Ile Ile Val Lys Asn Asp Asp Ser Trp
    1625            1630                1635

Leu Ala Ser Gln His Ser Leu Val Ser Gln Leu Arg Arg Val Trp
    1640            1645                1650

Val Ser Glu Asn Phe Gln Glu Arg His Arg Lys Glu Asn Met Ala
    1655            1660                1665

Ala Thr Asn Trp Lys Glu Pro Lys Leu Leu Ala Tyr Cys Leu Leu
    1670            1675                1680

Asn Tyr Cys Lys Arg Asn Tyr Gly Asp Ile Glu Leu Leu Phe Gln
    1685            1690                1695

Leu Leu Arg Ala Phe Thr Gly Arg Phe Leu Cys Asn Met Thr Phe
    1700            1705                1710

Leu Lys Glu Tyr Met Glu Glu Ile Pro Lys Asn Tyr Ser Ile
    1715            1720                1725

Ala Gln Lys Arg Ala Leu Phe Phe Arg Phe Val Asp Phe Asn Asp
    1730            1735                1740

Pro Asn Phe Gly Asp Glu Leu Lys Ala Lys Val Leu Gln His Ile
    1745            1750                1755
```

-continued

```
Leu Asn Pro Ala Phe Leu Tyr Ser Phe Glu Lys Gly Glu Gly Glu
    1760                1765                1770

Gln Leu Leu Gly Pro Pro Asn Pro Glu Gly Asp Asn Pro Glu Ser
    1775                1780                1785

Ile Thr Ser Val Phe Ile Thr Lys Val Leu Asp Pro Glu Lys Gln
    1790                1795                1800

Ala Asp Met Leu Asp Ser Leu Arg Ile Tyr Leu Leu Gln Tyr Ala
    1805                1810                1815

Thr Leu Leu Val Glu His Ala Pro His His Ile His Asp Asn Asn
    1820                1825                1830

Lys Asn Arg Asn Ser Lys Leu Arg Arg Leu Met Thr Phe Ala Trp
    1835                1840                1845

Pro Cys Leu Leu Ser Lys Ala Cys Val Asp Pro Ala Cys Lys Tyr
    1850                1855                1860

Ser Gly His Leu Leu Leu Ala His Ile Ile Ala Lys Phe Ala Ile
    1865                1870                1875

His Lys Lys Ile Val Leu Gln Val Phe His Ser Leu Leu Lys Ala
    1880                1885                1890

His Ala Met Glu Ala Arg Ala Ile Val Arg Gln Ala Met Ala Ile
    1895                1900                1905

Leu Thr Pro Ala Val Pro Ala Arg Met Glu Asp Gly His Gln Met
    1910                1915                1920

Leu Thr His Trp Thr Arg Lys Ile Ile Val Glu Glu Gly His Thr
    1925                1930                1935

Val Pro Gln Leu Val His Ile Leu His Leu Ile Val Gln His Phe
    1940                1945                1950

Lys Val Tyr Tyr Pro Val Arg His His Leu Val Gln His Met Val
    1955                1960                1965

Ser Ala Met Gln Arg Leu Gly Phe Thr Pro Ser Val Thr Ile Glu
    1970                1975                1980

Gln Arg Arg Leu Ala Val Asp Leu Ser Glu Val Val Ile Lys Trp
    1985                1990                1995

Glu Leu Gln Arg Ile Lys Asp Gln Gln Pro Asp Ser Asp Met Asp
    2000                2005                2010

Pro Asn Ser Ser Gly Glu Gly Val Asn Ser Val Ser Ser Ser Ile
    2015                2020                2025

Lys Arg Gly Leu Ser Val Asp Ser Ala Gln Glu Val Lys Arg Phe
    2030                2035                2040

Arg Thr Ala Thr Gly Ala Ile Ser Ala Val Phe Gly Arg Ser Gln
    2045                2050                2055

Ser Leu Pro Gly Ala Asp Ser Leu Leu Ala Lys Pro Ile Asp Lys
    2060                2065                2070

Gln His Thr Asp Thr Val Val Asn Phe Leu Ile Arg Val Ala Cys
    2075                2080                2085

Gln Val Asn Asp Asn Thr Asn Thr Ala Gly Ser Pro Gly Glu Val
    2090                2095                2100

Leu Ser Arg Arg Cys Val Asn Leu Leu Lys Thr Ala Leu Arg Pro
    2105                2110                2115

Asp Met Trp Pro Lys Ser Glu Leu Lys Leu Gln Trp Phe Asp Lys
    2120                2125                2130

Leu Leu Met Thr Val Glu Gln Pro Asn Gln Val Asn Tyr Gly Asn
    2135                2140                2145

Ile Cys Thr Gly Leu Glu Val Leu Ser Phe Leu Leu Thr Val Leu
```

```
                    2150                     2155                    2160

Gln Ser  Pro Ala Ile Leu Ser  Ser Phe Lys Pro Leu  Gln Arg Gly
    2165                    2170                    2175

Ile Ala  Ala Cys Met Thr Cys  Gly Asn Thr Lys Val  Leu Arg Ala
    2180                    2185                    2190

Val His  Ser Leu Leu Ser Arg  Leu Met Ser Ile Phe  Pro Thr Glu
    2195                    2200                    2205

Pro Ser  Thr Ser Ser Val Ala  Ser Lys Tyr Glu Glu  Leu Glu Cys
    2210                    2215                    2220

Leu Tyr  Ala Ala Val Gly Lys  Val Ile Tyr Glu Gly  Leu Thr Asn
    2225                    2230                    2235

Tyr Glu  Lys Ala Thr Asn Ala  Asn Pro Ser Gln Leu  Phe Gly Thr
    2240                    2245                    2250

Leu Met  Ile Leu Lys Ser Ala  Cys Ser Asn Asn Pro  Ser Tyr Ile
    2255                    2260                    2265

Asp Arg  Leu Ile Ser Val Phe  Met Arg Ser Leu Gln  Lys Met Val
    2270                    2275                    2280

Arg Glu  His Leu Asn Pro Gln  Ala Ala Ser Gly Ser  Thr Glu Ala
    2285                    2290                    2295

Thr Ser  Gly Thr Ser Glu Leu  Val Met Leu Ser Leu  Glu Leu Val
    2300                    2305                    2310

Lys Thr  Arg Leu Ala Val Met  Ser Met Glu Met Arg  Lys Asn Phe
    2315                    2320                    2325

Ile Gln  Ala Ile Leu Thr Ser  Leu Ile Glu Lys Ser  Pro Asp Ala
    2330                    2335                    2340

Lys Ile  Leu Arg Ala Val Val  Lys Ile Val Glu Glu  Trp Val Lys
    2345                    2350                    2355

Asn Asn  Ser Pro Met Ala Ala  Asn Gln Thr Pro Thr  Leu Arg Glu
    2360                    2365                    2370

Lys Ser  Ile Leu Leu Val Lys  Met Met Thr Tyr Ile  Glu Lys Arg
    2375                    2380                    2385

Phe Pro  Glu Asp Leu Glu Leu  Asn Ala Gln Phe Leu  Asp Leu Val
    2390                    2395                    2400

Asn Tyr  Val Tyr Arg Asp Glu  Thr Leu Ser Gly Ser  Glu Leu Thr
    2405                    2410                    2415

Ala Lys  Leu Glu Pro Ala Phe  Leu Ser Gly Leu Arg  Cys Ala Gln
    2420                    2425                    2430

Pro Leu  Ile Arg Ala Lys Phe  Phe Glu Val Phe Asp  Asn Ser Met
    2435                    2440                    2445

Lys Arg  Arg Val Tyr Glu Arg  Leu Leu Tyr Val Thr  Cys Ser Gln
    2450                    2455                    2460

Asn Trp  Glu Ala Met Gly Asn  His Phe Trp Ile Lys  Gln Cys Ile
    2465                    2470                    2475

Glu Leu  Leu Leu Ala Val Cys  Glu Lys Ser Thr Pro  Ile Gly Thr
    2480                    2485                    2490

Ser Cys  Gln Gly Ala Met Leu  Pro Ser Ile Thr Asn  Val Ile Asn
    2495                    2500                    2505

Leu Ala  Asp Ser His Asp Arg  Ala Ala Phe Ala Met  Val Thr His
    2510                    2515                    2520

Val Lys  Gln Glu Pro Arg Glu  Arg Glu Asn Ser Glu  Ser Lys Glu
    2525                    2530                    2535

Glu Asp  Val Glu Ile Asp Ile  Glu Leu Ala Pro Gly  Asp Gln Thr
    2540                    2545                    2550
```

-continued

Ser Thr Pro Lys Thr Lys Glu Leu Ser Glu Lys Asp Ile Gly Asn
2555                2560                2565

Gln Leu His Met Leu Thr Asn Arg His Asp Lys Phe Leu Asp Thr
2570                2575                2580

Leu Arg Glu Val Lys Thr Gly Ala Leu Leu Ser Ala Phe Val Gln
2585                2590                2595

Leu Cys His Ile Ser Thr Thr Leu Ala Glu Lys Thr Trp Val Gln
2600                2605                2610

Leu Phe Pro Arg Leu Trp Lys Ile Leu Ser Asp Arg Gln Gln His
2615                2620                2625

Ala Leu Ala Gly Glu Ile Ser Pro Phe Leu Cys Ser Gly Ser His
2630                2635                2640

Gln Val Gln Arg Asp Cys Gln Pro Ser Ala Leu Asn Cys Phe Val
2645                2650                2655

Glu Ala Met Ser Gln Cys Val Pro Pro Ile Pro Ile Arg Pro Cys
2660                2665                2670

Val Leu Lys Tyr Leu Gly Lys Thr His Asn Leu Trp Phe Arg Ser
2675                2680                2685

Thr Leu Met Leu Glu His Gln Ala Phe Glu Lys Gly Leu Ser Leu
2690                2695                2700

Gln Ile Lys Pro Lys Gln Thr Thr Glu Phe Tyr Glu Gln Glu Ser
2705                2710                2715

Ile Thr Pro Pro Gln Gln Glu Ile Leu Asp Ser Leu Ala Glu Leu
2720                2725                2730

Tyr Ser Leu Leu Gln Glu Glu Asp Met Trp Ala Gly Leu Trp Gln
2735                2740                2745

Lys Arg Cys Lys Tyr Ser Glu Thr Ala Thr Ala Ile Ala Tyr Glu
2750                2755                2760

Gln His Gly Phe Phe Glu Ala Gln Glu Ser Tyr Glu Lys Ala
2765                2770                2775

Met Asp Lys Ala Lys Lys Glu His Glu Arg Ser Asn Ala Ser Pro
2780                2785                2790

Ala Ile Phe Pro Glu Tyr Gln Leu Trp Glu Asp His Trp Ile Arg
2795                2800                2805

Cys Ser Lys Glu Leu Asn Gln Trp Glu Ala Leu Thr Glu Tyr Gly
2810                2815                2820

Gln Ser Lys Gly His Ile Asn Pro Tyr Leu Val Leu Glu Cys Ala
2825                2830                2835

Trp Arg Val Ser Asn Trp Thr Ala Met Lys Glu Ala Leu Val Gln
2840                2845                2850

Val Glu Val Ser Cys Pro Lys Glu Met Ala Trp Lys Val Asn Met
2855                2860                2865

Tyr Arg Gly Tyr Leu Ala Ile Cys His Pro Glu Glu Gln Gln Leu
2870                2875                2880

Ser Phe Ile Glu Arg Leu Val Glu Met Ala Ser Ser Leu Ala Ile
2885                2890                2895

Arg Glu Trp Arg Arg Leu Pro His Val Val Ser His Val His Thr
2900                2905                2910

Pro Leu Leu Gln Ala Ala Gln Gln Ile Ile Glu Leu Gln Glu Ala
2915                2920                2925

Ala Gln Ile Asn Ala Gly Leu Gln Pro Thr Asn Leu Gly Arg Asn
2930                2935                2940

```
Asn Ser Leu His Asp Met Lys Thr Val Val Lys Thr Trp Arg Asn
2945                2950                2955

Arg Leu Pro Ile Val Ser Asp Asp Leu Ser His Trp Ser Ser Ile
2960                2965                2970

Phe Met Trp Arg Gln His His Tyr Gln Ala Ile Val Thr Ala Tyr
2975                2980                2985

Glu Asn Ser Ser Gln His Asp Pro Ser Ser Asn Asn Ala Met Leu
2990                2995                3000

Gly Val His Ala Ser Ala Ser Ala Ile Ile Gln Tyr Gly Lys Ile
3005                3010                3015

Ala Arg Lys Gln Gly Leu Val Asn Val Ala Leu Asp Ile Leu Ser
3020                3025                3030

Arg Ile His Thr Ile Pro Thr Val Pro Ile Val Asp Cys Phe Gln
3035                3040                3045

Lys Ile Arg Gln Gln Val Lys Cys Tyr Leu Gln Leu Ala Gly Val
3050                3055                3060

Met Gly Lys Asn Glu Cys Met Gln Gly Leu Glu Val Ile Glu Ser
3065                3070                3075

Thr Asn Leu Lys Tyr Phe Thr Lys Glu Met Thr Ala Glu Phe Tyr
3080                3085                3090

Ala Leu Lys Gly Met Phe Leu Ala Gln Ile Asn Lys Ser Glu Glu
3095                3100                3105

Ala Asn Lys Ala Phe Ser Ala Ala Val Gln Met His Asp Val Leu
3110                3115                3120

Val Lys Ala Trp Ala Met Trp Gly Asp Tyr Leu Glu Asn Ile Phe
3125                3130                3135

Val Lys Glu Arg Gln Leu His Leu Gly Val Ser Ala Ile Thr Cys
3140                3145                3150

Tyr Leu His Ala Cys Arg His Gln Asn Glu Ser Lys Ser Arg Lys
3155                3160                3165

Tyr Leu Ala Lys Val Leu Trp Leu Leu Ser Phe Asp Asp Asp Lys
3170                3175                3180

Asn Thr Leu Ala Asp Ala Val Asp Lys Tyr Cys Ile Gly Val Pro
3185                3190                3195

Pro Ile Gln Trp Leu Ala Trp Ile Pro Gln Leu Leu Thr Cys Leu
3200                3205                3210

Val Gly Ser Glu Gly Lys Leu Leu Leu Asn Leu Ile Ser Gln Val
3215                3220                3225

Gly Arg Val Tyr Pro Gln Ala Val Tyr Phe Pro Ile Arg Thr Leu
3230                3235                3240

Tyr Leu Thr Leu Lys Ile Glu Gln Arg Glu Arg Tyr Lys Ser Asp
3245                3250                3255

Pro Gly Pro Ile Arg Ala Thr Ala Pro Met Trp Arg Cys Ser Arg
3260                3265                3270

Ile Met His Met Gln Arg Glu Leu His Pro Thr Leu Leu Ser Ser
3275                3280                3285

Leu Glu Gly Ile Val Asp Gln Met Val Trp Phe Arg Glu Asn Trp
3290                3295                3300

His Glu Glu Val Leu Arg Gln Leu Gln Gln Gly Leu Ala Lys Cys
3305                3310                3315

Tyr Ser Val Ala Phe Glu Lys Ser Gly Ala Val Ser Asp Ala Lys
3320                3325                3330

Ile Thr Pro His Thr Leu Asn Phe Val Lys Lys Leu Val Ser Thr
```

```
            3335                3340                3345
Phe Gly Val Gly Leu Glu Asn Val Ser Asn Val Ser Thr Met Phe
    3350                3355                3360
Ser Ser Ala Ala Ser Glu Ser Leu Ala Arg Arg Ala Gln Ala Thr
    3365                3370                3375
Ala Gln Asp Pro Val Phe Gln Lys Leu Lys Gly Gln Phe Thr Thr
    3380                3385                3390
Asp Phe Asp Phe Ser Val Pro Gly Ser Met Lys Leu His Asn Leu
    3395                3400                3405
Ile Ser Lys Leu Lys Lys Trp Ile Lys Ile Leu Glu Ala Lys Thr
    3410                3415                3420
Lys Gln Leu Pro Lys Phe Phe Leu Ile Glu Glu Lys Cys Arg Phe
    3425                3430                3435
Leu Ser Asn Phe Ser Ala Gln Thr Ala Glu Val Glu Ile Pro Gly
    3440                3445                3450
Glu Phe Leu Met Pro Lys Pro Thr His Tyr Tyr Ile Lys Ile Ala
    3455                3460                3465
Arg Phe Met Pro Arg Val Glu Ile Val Gln Lys His Asn Thr Ala
    3470                3475                3480
Ala Arg Arg Leu Tyr Ile Arg Gly His Asn Gly Lys Ile Tyr Pro
    3485                3490                3495
Tyr Leu Val Met Asn Asp Ala Cys Leu Thr Glu Ser Arg Arg Glu
    3500                3505                3510
Glu Arg Val Leu Gln Leu Leu Arg Leu Leu Asn Pro Cys Leu Glu
    3515                3520                3525
Lys Arg Lys Glu Thr Thr Lys Arg His Leu Phe Phe Thr Val Pro
    3530                3535                3540
Arg Val Val Ala Val Ser Pro Gln Met Arg Leu Val Glu Asp Asn
    3545                3550                3555
Pro Ser Ser Leu Ser Leu Val Glu Ile Tyr Lys Gln Arg Cys Ala
    3560                3565                3570
Lys Lys Gly Ile Glu His Asp Asn Pro Ile Ser Arg Tyr Tyr Asp
    3575                3580                3585
Arg Leu Ala Thr Val Gln Ala Arg Gly Thr Gln Ala Ser His Gln
    3590                3595                3600
Val Leu Arg Asp Ile Leu Lys Glu Val Gln Ser Asn Met Val Pro
    3605                3610                3615
Arg Ser Met Leu Lys Glu Trp Ala Leu His Thr Phe Pro Asn Ala
    3620                3625                3630
Thr Asp Tyr Trp Thr Phe Arg Lys Met Phe Thr Ile Gln Leu Ala
    3635                3640                3645
Leu Ile Gly Phe Ala Glu Phe Val Leu His Leu Asn Arg Leu Asn
    3650                3655                3660
Pro Glu Met Leu Gln Ile Ala Gln Asp Thr Gly Lys Leu Asn Val
    3665                3670                3675
Ala Tyr Phe Arg Phe Asp Ile Asn Asp Ala Thr Gly Asp Leu Asp
    3680                3685                3690
Ala Asn Arg Pro Val Pro Phe Arg Leu Thr Pro Asn Ile Ser Glu
    3695                3700                3705
Phe Leu Thr Thr Ile Gly Val Ser Gly Pro Leu Thr Ala Ser Met
    3710                3715                3720
Ile Ala Val Ala Arg Cys Phe Ala Gln Pro Asn Phe Lys Val Asp
    3725                3730                3735
```

| | | | | | | | | | | |
|---|---|---|---|---|---|---|---|---|---|---|
|Gly|Ile|Leu|Lys|Thr|Val|Leu|Arg|Asp|Glu|Ile|Ile|Ala|Trp|His|
| |3740| | | |3745| | | |3750| |

Lys Lys Thr Gln Glu Asp Thr Ser Ser Pro Leu Ser Ala Ala Gly
    3755            3760            3765

Gln Pro Glu Asn Met Asp Ser Gln Gln Leu Val Ser Leu Val Gln
    3770            3775            3780

Lys Ala Val Thr Ala Ile Met Thr Arg Leu His Asn Leu Ala Gln
    3785            3790            3795

Phe Glu Gly Gly Glu Ser Lys Val Asn Thr Leu Val Ala Ala Ala
    3800            3805            3810

Asn Ser Leu Asp Asn Leu Cys Arg Met Asp Pro Ala Trp His Pro
    3815            3820            3825

Trp Leu
    3830

<210> SEQ ID NO 3
<211> LENGTH: 4395
<212> TYPE: DNA
<213> ORGANISM: Homo sapiens

<400> SEQUENCE: 3

```
atgggcagag tgggctattg accctgctg gtgctgccgg cccttctggt ctggcgcggt    60
ccggcgccga gcgcggcggc ggagaagggt cccccgcgc taaatattgc ggtgatgctg   120
ggtcacagcc acgacgtgac agagcgcgaa cttcgaacac tgtggggccc cgagcaggcg   180
gcggggctgc ccctggacgt gaacgtggta gctctgctga tgaaccgcac cgaccccaag   240
agcctcatca cgcacgtgtg cgacctcatg tccggggcac gcatccacgg cctcgtgttt   300
ggggacgaca cggaccagga ggccgtagcc cagatgctgg attttatctc ctcccacacc   360
ttcgtcccca tcttgggcat tcatgggggc gcatctatga tcatggctga caaggatccg   420
acgtctacct tcttccagtt tggagcgtcc atccagcagc aagccacggt catgctgaag   480
atcatgcagg attatgactg gcatgtcttc tccctggtga ccactatctt ccctggctac   540
agggaattca tcagcttcgt caagaccaca gtggacaaca gctttgtggg ctgggacatg   600
cagaatgtga tcacactgga cacttccttt gaggatgcaa agacacaagt ccagctgaag   660
aagatccact cttctgtcat cttgctctac tgttccaaag acgaggctgt tctcattctg   720
agtgaggccc gctcccttgg cctcaccggg tatgatttct tctggattgt ccccagcttg   780
gtctctggga cacggagct catcccaaaa gagtttccat cgggactcat ttctgtctcc   840
tacgatgact gggactacag cctggaggcg agagtgaggg acggcattgg catcctaacc   900
accgctgcat cttctatgct ggagaagttc tcctacatcc ccgaggccaa ggccagctgc   960
tacgggcaga tggagaggcc agaggtcccg atgcacacct tgcacccatt tatggtcaat  1020
gttacatggg atgcaaaaga cttatccttc actgaggaag gctaccaggt gcaccccagg  1080
ctggtggtga ttgtgctgaa caagaccgg gaatgggaaa aggtgggcaa gtgggagaac  1140
catacgctga gcctgaggca cgccgtgtgg cccaggtaca gtccttctc cgactgtgag  1200
ccggatgaca ccatctcag catcgtcacc ctggaggagg ccccattcgt catcgtggaa  1260
gacatagacc ccctgaccga cgtgtgtg aggaacaccg tgccatgtcg aagttcgtc   1320
aaaatcaaca attcaaccaa tgaggggatg aatgtgaaga atgctgcaa ggggttctgc  1380
attgatattc tgaagaagct ttccagaact gtgaagttta cttacgacct ctatctggtg  1440
accaatggga agcatggcaa gaaagttaac aatgtgtgga atggaatgat cggtgaagtg  1500
```

```
gtctatcaac gggcagtcat ggcagttggc tcgctcacca tcaatgagga acgttctgaa   1560
gtggtggact tctctgtgcc ctttgtggaa acgggaatca gtgtcatggt ttcaagaagt   1620
aatggcaccg tctcaccttc tgcttttcta gaaccattca gcgcctctgt ctgggtgatg   1680
atgtttgtga tgctgctcat tgtttctgcc atagctgttt ttgtctttga atacttcagc   1740
cctgttggat acaacagaaa cttagccaaa gggaaagcac cccatgggcc ttcttttaca   1800
attgaaaaag ctatatggct tctttggggc ctggtgttca ataactccgt gcctgtccag   1860
aatcctaaag ggaccaccag caagatcatg gtatctgtat gggccttctt cgctgtcata   1920
ttcctggcta gctacacagc caatctggct gccttcatga tccaagagga atttgtggac   1980
caagtgaccg gcctcagtga caaaagttt cagagacctc atgactattc cccaccttt    2040 cgatttggga cagtgcctaa tggaagcacg gagagaaaca ttcggaataa ctatccctac   2100
atgcatcagt acatgaccaa atttaatcag aaaggagtag aggacgcctt ggtcagcctg   2160
aaaacgggga agctggacgc tttcatctac gatgccgcag tcttgaatta caaggctggg   2220
agggatgaag gctgcaagct ggtgaccatc gggagtgggt acatctttgc caccaccggt   2280 tatgaattg cccttcagaa aggctctcct tggaagaggc agatcgacct ggccttgctt   2340
cagtttgtgg gtgatggtga gatggaggag ctggagaccc tgtggctcac tgggatctgc   2400
cacaacgaga gaacgaggt gatgagcagc cagctggaca ttgacaacat ggcgggcgta   2460
ttctacatgc tggctgccgc catggccctt agcctcatca ccttcatctg ggagcacctc   2520
ttctactgga agctgcgctt ctgtttcacg ggcgtgtgct ccgaccggcc tgggttgctc   2580
ttctccatca gcagggcat ctacagctgc attcatggag tgcacattga agaaaagaag   2640
aagtctccag acttcaatct gacgggatcc cagagcaaca tgttaaaact cctccggtca   2700
gccaaaaaca tttccagcat gtccaacatg aactcctcaa gaatggactc acccaaaaga   2760
gctgctgact tcatccaaag aggttccctc atcatggaca tggtttcaga taagggggaat   2820 ttgatgtact cagacaacag gtcctttcag gggaaagaga gcattttgg agacaacatg   2880 aacgaactcc aaacatttgt ggccaaccgg cagaaggata acctcaataa ctatgtattc   2940
cagggacaac atcctcttac tctcaatgag tccaaccca acacggtgga ggtggccgtg   3000
agcacagaat ccaaagcgaa ctctagaccc cggcagctgt ggaagaaatc cgtggattcc   3060
atacgccagg attcactatc ccagaatcca gtctcccaga gggatgaggc aacagcagag   3120
aataggaccc actccctaaa gagccctagg tatcttccag aagagatggc ccactctgac   3180
atttcagaaa cgtcaaatcg ggccacgtgc cacagggaac ctgacaacag taagaaccac   3240
aaaaccaagg acaactttaa aaggtcagtg gcctccaaat accccaagga ctgtagtgag   3300
gtcgagcgca cctacctgaa aaccaaatca agctccccta gagacaagat ctacactata   3360
gatggtgaga aggagcctgg tttccactta gatccacccc agtttgttga aaatgtgacc   3420
ctgcccgaga acgtggactt cccggacccc taccaggatc cagtgaaaaa cttccgcaag   3480
ggggactcca cgctgccaat gaaccggaac cccttgcata tgaagagggg ctttccaac   3540 aacgaccagt ataaactcta ctccaagcac ttccttgga agacaaggg ttccccgcac   3600 agtgagacca gcgagcgata ccggcagaac tccacgcact gcagaagctg cctttccaac   3660
atgcccacct attcaggcca cttcaccatg aggtcccct tcaagtgcga tgcctgcctg   3720
cggatgggga acctctatga catcgatgaa gaccagatgc ttcaggagac aggtaaccca   3780
gccaccgggg agcaggtcta ccagcaggac tgggcacaga acaatgccct tcaattacaa   3840
```

-continued

```
aagaacaagc taaggattag ccgtcagcat tcctacgata acattgtcga caaacctagg   3900
gagctagacc ttagcaggcc ctcccggagc ataagcctca aggacaggga acggcttctg   3960
gagggaaatt tttacggcag cctgtttagt gtcccctcaa gcaaactctc ggggaaaaaa   4020
agctcccttt tccccaagg tctggaggac agcaagagga gcaagtctct cttgccagac    4080
cacacctccg ataacccttt cctccactcc cacagggatg accaacgctt ggttattggg   4140
agatgcccct cggaccctta caaacactcg ttgccatccc aggcggtgaa tgacagctat   4200
cttcggtcgt ccttgaggtc aacggcatcg tactgttcca gggacagtcg gggccacaat   4260
gatgtgtata tttcggagca tgttatgcct tatgctgcaa ataagaataa tatgtactct   4320 accccaggg ttttaaattc ctgcagcaat agacgcgtgt acaagaaaat gcctagtatc    4380
gaatctgatg tttaa                                                    4395
```

<210> SEQ ID NO 4
<211> LENGTH: 1464
<212> TYPE: PRT
<213> ORGANISM: Homo sapiens

<400> SEQUENCE: 4

```
Met Gly Arg Val Gly Tyr Trp Thr Leu Leu Val Leu Pro Ala Leu Leu
1               5                  10                  15

Val Trp Arg Gly Pro Ala Pro Ser Ala Ala Ala Glu Lys Gly Pro Pro
            20                  25                  30

Ala Leu Asn Ile Ala Val Met Leu Gly His Ser His Asp Val Thr Glu
        35                  40                  45

Arg Glu Leu Arg Thr Leu Trp Gly Pro Glu Gln Ala Ala Gly Leu Pro
    50                  55                  60

Leu Asp Val Asn Val Val Ala Leu Leu Met Asn Arg Thr Asp Pro Lys
65                  70                  75                  80

Ser Leu Ile Thr His Val Cys Asp Leu Met Ser Gly Ala Arg Ile His
                85                  90                  95

Gly Leu Val Phe Gly Asp Asp Thr Asp Gln Glu Ala Val Ala Gln Met
            100                 105                 110

Leu Asp Phe Ile Ser Ser His Thr Phe Val Pro Ile Leu Gly Ile His
        115                 120                 125

Gly Gly Ala Ser Met Ile Met Ala Asp Lys Asp Pro Thr Ser Thr Phe
    130                 135                 140

Phe Gln Phe Gly Ala Ser Ile Gln Gln Gln Ala Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Glu Phe Ile Ser Phe Val Lys Thr Thr Val Asp
            180                 185                 190

Asn Ser Phe Val Gly Trp Asp Met Gln Asn Val Ile Thr Leu Asp Thr
        195                 200                 205

Ser Phe Glu Asp Ala Lys Thr Gln Val Gln Leu Lys Lys Ile His Ser
    210                 215                 220

Ser Val Ile Leu Leu Tyr Cys Ser Lys Asp Glu Ala Val Leu Ile Leu
225                 230                 235                 240

Ser Glu Ala Arg Ser Leu Gly Leu Thr Gly Tyr Asp Phe Phe Trp Ile
                245                 250                 255

Val Pro Ser Leu Val Ser Gly Asn Thr Glu Leu Ile Pro Lys Glu Phe
            260                 265                 270
```

```
Pro Ser Gly Leu Ile Ser Val Ser Tyr Asp Asp Trp Asp Tyr Ser Leu
            275                 280                 285

Glu Ala Arg Val Arg Asp Gly Ile Gly Ile Leu Thr Thr Ala Ala Ser
290                 295                 300

Ser Met Leu Glu Lys Phe Ser Tyr Ile Pro Glu Ala Lys Ala Ser Cys
305                 310                 315                 320

Tyr Gly Gln Met Glu Arg Pro Glu Val Pro Met His Thr Leu His Pro
                325                 330                 335

Phe Met Val Asn Val Thr Trp Asp Gly Lys Asp Leu Ser Phe Thr Glu
            340                 345                 350

Glu Gly Tyr Gln Val His Pro Arg Leu Val Val Ile Val Leu Asn Lys
        355                 360                 365

Asp Arg Glu Trp Glu Lys Val Gly Lys Trp Glu Asn His Thr Leu Ser
370                 375                 380

Leu Arg His Ala Val Trp Pro Arg Tyr Lys Ser Phe Ser Asp Cys Glu
385                 390                 395                 400

Pro Asp Asp Asn His Leu Ser Ile Val Thr Leu Glu Glu Ala Pro Phe
                405                 410                 415

Val Ile Val Glu Asp Ile Asp Pro Leu Thr Glu Thr Cys Val Arg Asn
            420                 425                 430

Thr Val Pro Cys Arg Lys Phe Val Lys Ile Asn Asn Ser Thr Asn Glu
        435                 440                 445

Gly Met Asn Val Lys Lys Cys Cys Lys Gly Phe Cys Ile Asp Ile Leu
450                 455                 460

Lys Lys Leu Ser Arg Thr Val Lys Phe Thr Tyr Asp Leu Tyr Leu Val
465                 470                 475                 480

Thr Asn Gly Lys His Gly Lys Lys Val Asn Asn Val Trp Asn Gly Met
                485                 490                 495

Ile Gly Glu Val Val Tyr Gln Arg Ala Val Met Ala Val Gly Ser Leu
            500                 505                 510

Thr Ile Asn Glu Glu Arg Ser Glu Val Val Asp Phe Ser Val Pro Phe
        515                 520                 525

Val Glu Thr Gly Ile Ser Val Met Val Ser Arg Ser Asn Gly Thr Val
530                 535                 540

Ser Pro Ser Ala Phe Leu Glu Pro Phe Ser Ala Ser Val Trp Val Met
545                 550                 555                 560

Met Phe Val Met Leu Leu Ile Val Ser Ala Ile Ala Val Phe Val Phe
                565                 570                 575

Glu Tyr Phe Ser Pro Val Gly Tyr Asn Arg Asn Leu Ala Lys Gly Lys
            580                 585                 590

Ala Pro His Gly Pro Ser Phe Thr Ile Gly Lys Ala Ile Trp Leu Leu
        595                 600                 605

Trp Gly Leu Val Phe Asn Asn Ser Val Pro Val Gln Asn Pro Lys Gly
610                 615                 620

Thr Thr Ser Lys Ile Met Val Ser Val Trp Ala Phe Phe Ala Val Ile
625                 630                 635                 640

Phe Leu Ala Ser Tyr Thr Ala Asn Leu Ala Ala Phe Met Ile Gln Glu
                645                 650                 655

Glu Phe Val Asp Gln Val Thr Gly Leu Ser Asp Lys Lys Phe Gln Arg
            660                 665                 670

Pro His Asp Tyr Ser Pro Pro Phe Arg Phe Gly Thr Val Pro Asn Gly
        675                 680                 685

Ser Thr Glu Arg Asn Ile Arg Asn Asn Tyr Pro Tyr Met His Gln Tyr
```

-continued

```
                     690                 695                 700
Met Thr Lys Phe Asn Gln Lys Gly Val Glu Asp Ala Leu Val Ser Leu
705                 710                 715                 720

Lys Thr Gly Lys Leu Asp Ala Phe Ile Tyr Asp Ala Ala Val Leu Asn
                725                 730                 735

Tyr Lys Ala Gly Arg Asp Glu Gly Cys Lys Leu Val Thr Ile Gly Ser
                740                 745                 750

Gly Tyr Ile Phe Ala Thr Thr Gly Tyr Gly Ile Ala Leu Gln Lys Gly
                755                 760                 765

Ser Pro Trp Lys Arg Gln Ile Asp Leu Ala Leu Leu Gln Phe Val Gly
            770                 775                 780

Asp Gly Glu Met Glu Glu Leu Glu Thr Leu Trp Leu Thr Gly Ile Cys
785                 790                 795                 800

His Asn Glu Lys Asn Glu Val Met Ser Ser Gln Leu Asp Ile Asp Asn
                805                 810                 815

Met Ala Gly Val Phe Tyr Met Leu Ala Ala Ala Met Ala Leu Ser Leu
                820                 825                 830

Ile Thr Phe Ile Trp Glu His Leu Phe Tyr Trp Lys Leu Arg Phe Cys
                835                 840                 845

Phe Thr Gly Val Cys Ser Asp Arg Pro Gly Leu Leu Phe Ser Ile Ser
                850                 855                 860

Arg Gly Ile Tyr Ser Cys Ile His Gly Val His Ile Glu Glu Lys Lys
865                 870                 875                 880

Lys Ser Pro Asp Phe Asn Leu Thr Gly Ser Gln Ser Asn Met Leu Lys
                885                 890                 895

Leu Leu Arg Ser Ala Lys Asn Ile Ser Ser Met Ser Asn Met Asn Ser
                900                 905                 910

Ser Arg Met Asp Ser Pro Lys Arg Ala Ala Asp Phe Ile Gln Arg Gly
                915                 920                 925

Ser Leu Ile Met Asp Met Val Ser Asp Lys Gly Asn Leu Met Tyr Ser
                930                 935                 940

Asp Asn Arg Ser Phe Gln Gly Lys Glu Ser Ile Phe Gly Asp Asn Met
945                 950                 955                 960

Asn Glu Leu Gln Thr Phe Val Ala Asn Arg Gln Lys Asp Asn Leu Asn
                965                 970                 975

Asn Tyr Val Phe Gln Gly Gln His Pro Leu Thr Leu Asn Glu Ser Asn
                980                 985                 990

Pro Asn Thr Val Glu Val Ala Val  Ser Thr Glu Ser Lys  Ala Asn Ser
                995                 1000                1005

Arg Pro  Arg Gln Leu Trp Lys  Lys Ser Val Asp Ser  Ile Arg Gln
    1010                1015                1020

Asp Ser  Leu Ser Gln Asn Pro  Val Ser Gln Arg Asp  Glu Ala Thr
    1025                1030                1035

Ala Glu  Asn Arg Thr His Ser  Leu Lys Ser Pro Arg  Tyr Leu Pro
    1040                1045                1050

Glu Glu  Met Ala His Ser Asp  Ile Ser Glu Thr Ser  Asn Arg Ala
    1055                1060                1065

Thr Cys  His Arg Glu Pro Asp  Asn Ser Lys Asn His  Lys Thr Lys
    1070                1075                1080

Asp Asn  Phe Lys Arg Ser Val  Ala Ser Lys Tyr Pro  Lys Asp Cys
    1085                1090                1095

Ser Glu  Val Glu Arg Thr Tyr  Leu Lys Thr Lys Ser  Ser Ser Pro
    1100                1105                1110
```

Arg Asp Lys Ile Tyr Thr Ile Asp Gly Glu Lys Glu Pro Gly Phe
1115                1120                1125

His Leu Asp Pro Pro Gln Phe Val Glu Asn Val Thr Leu Pro Glu
1130                1135                1140

Asn Val Asp Phe Pro Asp Pro Tyr Gln Asp Pro Ser Glu Asn Phe
1145                1150                1155

Arg Lys Gly Asp Ser Thr Leu Pro Met Asn Arg Asn Pro Leu His
1160                1165                1170

Asn Glu Glu Gly Leu Ser Asn Asn Asp Gln Tyr Lys Leu Tyr Ser
1175                1180                1185

Lys His Phe Thr Leu Lys Asp Lys Gly Ser Pro His Ser Glu Thr
1190                1195                1200

Ser Glu Arg Tyr Arg Gln Asn Ser Thr His Cys Arg Ser Cys Leu
1205                1210                1215

Ser Asn Met Pro Thr Tyr Ser Gly His Phe Thr Met Arg Ser Pro
1220                1225                1230

Phe Lys Cys Asp Ala Cys Leu Arg Met Gly Asn Leu Tyr Asp Ile
1235                1240                1245

Asp Glu Asp Gln Met Leu Gln Glu Thr Gly Asn Pro Ala Thr Gly
1250                1255                1260

Glu Gln Val Tyr Gln Gln Asp Trp Ala Gln Asn Asn Ala Leu Gln
1265                1270                1275

Leu Gln Lys Asn Lys Leu Arg Ile Ser Arg Gln His Ser Tyr Asp
1280                1285                1290

Asn Ile Val Asp Lys Pro Arg Glu Leu Asp Leu Ser Arg Pro Ser
1295                1300                1305

Arg Ser Ile Ser Leu Lys Asp Arg Glu Arg Leu Leu Glu Gly Asn
1310                1315                1320

Phe Tyr Gly Ser Leu Phe Ser Val Pro Ser Ser Lys Leu Ser Gly
1325                1330                1335

Lys Lys Ser Ser Leu Phe Pro Gln Gly Leu Glu Asp Ser Lys Arg
1340                1345                1350

Ser Lys Ser Leu Leu Pro Asp His Thr Ser Asp Asn Pro Phe Leu
1355                1360                1365

His Ser His Arg Asp Asp Gln Arg Leu Val Ile Gly Arg Cys Pro
1370                1375                1380

Ser Asp Pro Tyr Lys His Ser Leu Pro Ser Gln Ala Val Asn Asp
1385                1390                1395

Ser Tyr Leu Arg Ser Ser Leu Arg Ser Thr Ala Ser Tyr Cys Ser
1400                1405                1410

Arg Asp Ser Arg Gly His Asn Asp Val Tyr Ile Ser Glu His Val
1415                1420                1425

Met Pro Tyr Ala Ala Asn Lys Asn Asn Met Tyr Ser Thr Pro Arg
1430                1435                1440

Val Leu Asn Ser Cys Ser Asn Arg Arg Val Tyr Lys Lys Met Pro
1445                1450                1455

Ser Ile Glu Ser Asp Val
1460

<210> SEQ ID NO 5
<211> LENGTH: 11
<212> TYPE: DNA
<213> ORGANISM: Homo sapiens

```
<400> SEQUENCE: 5
tgtctccctc t                                                          11

<210> SEQ ID NO 6
<211> LENGTH: 11
<212> TYPE: DNA
<213> ORGANISM: Homo sapiens

<400> SEQUENCE: 6
tgtctycctc t                                                          11

<210> SEQ ID NO 7
<211> LENGTH: 11
<212> TYPE: DNA
<213> ORGANISM: Homo sapiens

<400> SEQUENCE: 7
tgtctyyctc t                                                          11

<210> SEQ ID NO 8
<211> LENGTH: 51
<212> TYPE: PRT
<213> ORGANISM: Canis familiaris

<400> SEQUENCE: 8
```

Leu Pro Glu Met Gly Ser His Val Glu Leu Ser Asn Leu Tyr Leu Lys
1               5                   10                  15

Leu Phe Lys Leu Val Phe Gly Ser Val Ser Leu Phe Ala Ala Glu Asn
            20                  25                  30

Glu Gln Met Leu Lys Pro His Leu His Lys Ile Val Asn Ser Ser Met
        35                  40                  45

Glu Leu Ala
    50

```
<210> SEQ ID NO 9
<211> LENGTH: 51
<212> TYPE: PRT
<213> ORGANISM: Pan troglodytes

<400> SEQUENCE: 9
```

Leu Pro Glu Met Gly Ser Asn Val Glu Leu Ser Asn Leu Tyr Leu Lys
1               5                   10                  15

Leu Phe Lys Leu Val Phe Gly Ser Val Ser Leu Phe Ala Ala Glu Asn
            20                  25                  30

Glu Gln Met Leu Lys Pro His Leu His Lys Ile Val Asn Ser Ser Met
        35                  40                  45

Glu Leu Ala
    50

```
<210> SEQ ID NO 10
<211> LENGTH: 51
<212> TYPE: PRT
<213> ORGANISM: Bos taurus

<400> SEQUENCE: 10
```

Leu Pro Glu Met Gly Ser Asn Val Glu Leu Ser Asn Leu Tyr Leu Lys
1               5                   10                  15

Leu Phe Lys Leu Val Phe Gly Ser Val Ser Leu Phe Ala Ala Glu Asn
            20                  25                  30

Glu Gln Met Leu Lys Pro His Leu His Lys Ile Val Asn Ser Ser Met

```
                35                  40                  45

Glu Leu Ala
    50

<210> SEQ ID NO 11
<211> LENGTH: 51
<212> TYPE: PRT
<213> ORGANISM: Rattus norvegicus

<400> SEQUENCE: 11

Leu Pro Glu Met Gly Ser Asn Val Glu Leu Ser Asn Leu Tyr Leu Lys
1               5                   10                  15

Leu Phe Lys Leu Val Phe Gly Ser Val Ser Leu Phe Ala Ala Glu Asn
            20                  25                  30

Glu Gln Met Leu Lys Pro His Leu His Lys Ile Val Asn Ser Ser Met
        35                  40                  45

Glu Leu Ala
    50

<210> SEQ ID NO 12
<211> LENGTH: 51
<212> TYPE: PRT
<213> ORGANISM: Gallus gallus

<400> SEQUENCE: 12

Leu Pro Glu Met Gly Ser Asn Val Glu Leu Ser Asn Leu Tyr Leu Lys
1               5                   10                  15

Leu Phe Lys Leu Val Phe Gly Ser Val Ser Leu Phe Ala Ala Glu Asn
            20                  25                  30

Glu Gln Met Leu Lys Pro His Leu His Lys Ile Val Asn Ser Ser Met
        35                  40                  45

Glu Leu Ala
    50

<210> SEQ ID NO 13
<211> LENGTH: 51
<212> TYPE: PRT
<213> ORGANISM: Danio rerio

<400> SEQUENCE: 13

Leu Pro Glu Met Gly Ser Asn Val Glu Leu Ser Asn Leu Tyr Leu Lys
1               5                   10                  15

Leu Phe Lys Leu Val Phe Gly Ser Val Ser Leu Phe Ala Ala Glu Asn
            20                  25                  30

Glu Gln Met Leu Lys Pro His Leu His Lys Ile Val Asn Ser Ser Met
        35                  40                  45

Glu Leu Ala
    50

<210> SEQ ID NO 14
<211> LENGTH: 51
<212> TYPE: PRT
<213> ORGANISM: Mus musculus

<400> SEQUENCE: 14

Leu Pro Glu Met Gly Ser Asn Val Glu Leu Ser Asn Leu Tyr Leu Lys
1               5                   10                  15

Leu Phe Lys Leu Val Phe Gly Ser Val Ser Leu Phe Ala Ala Glu Asn
            20                  25                  30
```

-continued

Glu Gln Met Leu Lys Pro His Leu His Lys Ile Val Asn Ser Ser Met
            35                  40                  45

Glu Leu Ala
    50

<210> SEQ ID NO 15
<211> LENGTH: 51
<212> TYPE: PRT
<213> ORGANISM: Drosophila melanogaster

<400> SEQUENCE: 15

Met Glu Glu Met Gly Ser Asn Leu Glu Arg Ser Asn Leu Tyr Leu Arg
1               5                   10                  15

Leu Phe Lys Leu Val Phe Gly Ser Val Ser Leu Phe Pro Val Glu Asn
            20                  25                  30

Glu Gln Met Leu Arg Pro His Leu His Lys Ile Val Asn Arg Ser Met
            35                  40                  45

Glu Leu Ala
    50

<210> SEQ ID NO 16
<211> LENGTH: 51
<212> TYPE: PRT
<213> ORGANISM: Anopheles gambiae

<400> SEQUENCE: 16

Met Asp Glu Met Gly Ser Asn Ile Glu Arg Ser Asn Leu Tyr Leu Arg
1               5                   10                  15

Leu Phe Lys Leu Val Phe Gly Ser Val Ser Leu Phe Ala Ala Glu Asn
            20                  25                  30

Glu His Met Leu Arg Pro His Leu His Asn Ile Val Asn Arg Ser Met
            35                  40                  45

Glu Leu Ala
    50

<210> SEQ ID NO 17
<211> LENGTH: 53
<212> TYPE: PRT
<213> ORGANISM: Caenorhabditis elegans

<400> SEQUENCE: 17

Met Lys Leu Leu Glu Val Ser Asn Asp Lys Thr Met Leu Tyr Val Lys
1               5                   10                  15

Leu Phe Lys Ile Ile Phe Ser Ala Ile Gly Ala Asn Gly Ser Gly Leu
            20                  25                  30

His Gly Asp Lys Met Leu Thr Ser Tyr Leu Pro Glu Ile Leu Lys Gln
            35                  40                  45

Ser Thr Val Leu Ala
    50

<210> SEQ ID NO 18
<211> LENGTH: 52
<212> TYPE: PRT
<213> ORGANISM: Saccharomyces cerevisiae

<400> SEQUENCE: 18

Leu Lys Asp Leu Gly Asn Val Asp Phe Asn Thr Ser Asn Val Leu Ile
1               5                   10                  15

Arg Leu Phe Lys Leu Ser Phe Met Ser Val Asn Leu Phe Pro Asn Ile
            20                  25                  30

Asn Glu Val Val Leu Leu Pro His Leu Asn Asp Leu Ile Leu Asn Ser
         35                  40                  45

Leu Lys Tyr Ser
     50

<210> SEQ ID NO 19
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 19
gtaaaacgac ggccagttaa aactgctttg gggaagg                             37

<210> SEQ ID NO 20
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 20
gagtgcctat agtcccaaaa a                                              21

<210> SEQ ID NO 21
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 21
gtaaaacgac ggccagt                                                   17

<210> SEQ ID NO 22
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 22
gtaaaacgac ggccagtttg ctacgattct ggtggaa                             37

<210> SEQ ID NO 23
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 23
cgtgaggccc tgtctctaac                                                20

<210> SEQ ID NO 24
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 24
gtaaaacgac ggccagt                                                   17

<210> SEQ ID NO 25
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 25
gtaaaacgac ggccagtcct atcctgctgc tgagttcc                          38

<210> SEQ ID NO 26
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 26
agtttccggc cttaccttgt c                                            21

<210> SEQ ID NO 27
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 27
gtaaaacgac ggccagtaga gtgggctatt ggaccctg                          38

<210> SEQ ID NO 28
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 28
gaggcaagac ctggttctca c                                            21

<210> SEQ ID NO 29
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 29
gtaaaacgac ggccagtcta ggacgcagtt tgtgcttc                          38

<210> SEQ ID NO 30
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 30
gaacagcctc gtctttggaa c                                            21

<210> SEQ ID NO 31
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 31
gtaaaacgac ggccagtggc tacagggaat tcatcagc          38

<210> SEQ ID NO 32
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 32
tcagtgcgta tttccaacaa tg          22

<210> SEQ ID NO 33
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 33
gtaaaacgac ggccagtgca gagaggcttc ttgtgatg          38

<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 34
agaaagaagc actgtgagcc c          21

<210> SEQ ID NO 35
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 35
gtaaaacgac ggccagtgga aaggatttgc ctctccag          38

<210> SEQ ID NO 36
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 36
gcaagtgtgg cacatctcta gg          22

<210> SEQ ID NO 37
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 37
gtaaaacgac ggccagtgtc cttgggaaag ccacttc          37

<210> SEQ ID NO 38

```
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 38
cgttgataga ccacctggat g                                              21

<210> SEQ ID NO 39
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 39
gtaaaacgac ggccagtatg tctgggcttc ctgctg                              36

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
tcctgacctc atgatccacc                                                20

<210> SEQ ID NO 41
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 41
gtaaaacgac ggccagtttc catcttctgg caaccttc                            38

<210> SEQ ID NO 42
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 42
tcaatgagag gcacctgaat c                                              21

<210> SEQ ID NO 43
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 43
gtaaaacgac ggccagtttg tcatcctgcc ctaatgc                             37

<210> SEQ ID NO 44
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 44
```
catgccgaga gtcaatttct g                                              21

<210> SEQ ID NO 45
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 45
gtaaaacgac ggccagtaaa gtgtgggatg ctttcagg                             38

<210> SEQ ID NO 46
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 46
atgcaaagat ccactgggaa g                                              21

<210> SEQ ID NO 47
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 47
gtaaaacgac ggccagtgtc tgttccaaac ccagaagc                             38

<210> SEQ ID NO 48
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 48
tgagacatca agaacccaag c                                              21

<210> SEQ ID NO 49
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 49
gtaaaacgac ggccagtccc tatgctttgc aacttgtc                             38

<210> SEQ ID NO 50
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 50
gaaaccatgt ccatgatgag g                                              21

<210> SEQ ID NO 51
<211> LENGTH: 38
<212> TYPE: DNA

```
<213> ORGANISM: Artificial Sequence
<220> FEATURE:
<223> OTHER INFORMATION: Synthetic polynucleotide

<400> SEQUENCE: 51
gtaaaacgac ggccagtcag gcatctacag ctgcattc                    38

<210> SEQ ID NO 52
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 52
ggagtgggtc ctattctctg c                                      21

<210> SEQ ID NO 53
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 53
gtaaaacgac ggccagtaga caacaggtcc tttcaggg                    38

<210> SEQ ID NO 54
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 54
tgttgtcagg ttccctgtgg                                        20

<210> SEQ ID NO 55
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 55
gtaaaacgac ggccagtatt ccatacgcca ggattcac                    38

<210> SEQ ID NO 56
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 56
gtatcgctcg ctggtctcac                                        20

<210> SEQ ID NO 57
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 57
gtaaaacgac ggccagtaac gtggacttcc cggac                       35
```

<210> SEQ ID NO 58
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 58
gcccagtcct gctggtagac                                        20

<210> SEQ ID NO 59
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 59
gtaaaacgac ggccagtgtg agaccagcga gcgatac                     37

<210> SEQ ID NO 60
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 60
gaaagggtta tcggaggtgt g                                      21

<210> SEQ ID NO 61
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 61
gtaaaacgac ggccagtgct agaccttagc aggccctc                    38

<210> SEQ ID NO 62
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 62
tttaccctcc agaacattgg c                                      21

<210> SEQ ID NO 63
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 63
cagatggtga aaggaatgct c                                      21

<210> SEQ ID NO 64
<211> LENGTH: 24
<212> TYPE: DNA
<213> ORGANISM: Artificial Sequence
<220> FEATURE:

```
<223> OTHER INFORMATION: Synthetic polynucleotide

<400> SEQUENCE: 64
gcaaagagga agacagagcc aaag                                              24

<210> SEQ ID NO 65
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 65
ctttggctct gtcttcctct ttgc                                              24

<210> SEQ ID NO 66
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 66
gttcataaca acatgcacac ag                                                22

<210> SEQ ID NO 67
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 67
ccggcgtgta agaaagggag aatatctcga gatattctcc ctttcttaca cgttttt         57

<210> SEQ ID NO 68
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 68
cgtgtaagaa agggagaata t                                                 21

<210> SEQ ID NO 69
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 69
atattctccc tttcttacac g                                                 21

<210> SEQ ID NO 70
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 70
ccgggccctg ttctttcgct tgtactcga gtacaaagcg aaagaacagg gcttttt          57
```

```
<210> SEQ ID NO 71
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 71
gccctgttct ttcgctttgt a                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 72
tacaaagcga aagaacaggg c                                              21
```

GRIN2A MUTATIONS AND USE THEREOF FOR THE DIAGNOSIS OF MELANOMA

CROSS REFERENCE TO RELATED APPLICATIONS

This is the U.S. National Stage of International Application No. PCT/US2012/022687, filed Jan. 26, 2012 published in English under PCT Article 21(2), which claims the benefit of U.S. Provisional Application No. 61/462,471, filed Feb. 2, 2011, which is herein incorporated by reference in its entirety.

FIELD

This disclosure concerns diagnostic markers for melanoma. In particular, this disclosure concerns identification of mutations in the transformation/transcription domain-associated protein (TRRAP) and glutamate receptor, ionotropic, N-methyl D-aspartate 2A (GRIN2A) genes, and their use for the diagnosis and treatment of melanoma.

BACKGROUND

Melanoma is the most deadly form of skin cancer. Despite years of research, metastatic melanoma disease has a dismal prognosis and is often fatal (Jemal et al., *CA Cancer J Clin* 59:225-249, 2009). There are few therapeutic options for melanoma patients, demonstrating a need for new clinically relevant targets. Although candidate gene analyses have been powerful in identifying melanoma driver mutations (Davies et al., *Nature* 417:949-954, 2002; Curtin et al., *J Clin Oncol* 24:4340-4346, 2006; Prickett et al., *Nat Genet.* 41:1127-1132, 2009), no comprehensive analysis of this tumor type has yet been performed.

Glutamate antagonists have previously been shown to inhibit proliferation of human tumor cells (Rzeski et al., *Proc Natl Acad Sci USA* 98(11):6372-6377, 2001). Glutamate is known to activate two different types of receptors—ionotropic glutamate receptors (iGluRs) and metabotropic glutamate receptors (mGlus). iGluRs are ligand-gated ion channels that allow cations, such as calcium and potassium, to pass through the plasma membrane of the cell after being bound by glutamate. iGluRs are subdivided into three receptor types according to agonist response, one of which is N-methyl-D-aspartate (NMDA) (Hollmann and Heinemann, *Annu Rev Neurosci* 17:31-108, 1994). The glutamate receptor, ionotropic, N-methyl D-aspartate 2A (GRIN2A) gene encodes a subunit of NMDA receptors; the GRIN2A subunit contains the agonist binding site for glutamate (Johnson and Ascher, *Nature* 325:529-531, 1987).

Prior studies have suggested that transformation/transcription domain-associated protein (TRRAP) may function as an oncogene in pancreatic cancer (Loukopoulos et al., *Cancer Sci* 98(3):392-400, 2007; Bashyam et al., *Neoplasia* 7(6):556-562, 2005). TRRAP is an adaptor protein found in various multiprotein chromatin complexes with histone acetyltransferase activity, which in turn is responsible for epigenetic transcription activation. TRRAP plays a central role in the transcriptional activity of p53, c-Myc, E2F1 and other transcription factors (McMahon et al., *Cell* 94:363-374, 1998; Barley et al., *Mol Cell* 8:1243-1254, 2001). TRRAP knockout mice are embryonic lethal suggesting that TRRAP is essential for cell survival (Herceg et al., *Nat Genet.* 29:206-211, 2001).

SUMMARY

Disclosed herein are 68 human genes with an elevated mutation frequency in melanoma. This disclosure specifically describes the identification of nine genes with recurring mutations in melanoma and 16 genes that are highly mutated in melanoma. In particular, disclosed herein is the identification of a recurrent mutation in human TRRAP (C2165T) found in six different melanoma samples. Also disclosed is the identification of 34 different nonsynonymous somatic mutations of human GRIN2A in melanoma samples.

Provided herein is a method of diagnosing a subject as having melanoma, or having a greater susceptibility to developing melanoma, by detecting at least one mutation in the TRRAP gene or the GRIN2A gene. The presence of the at least one mutation indicates the subject has melanoma or is susceptible to developing melanoma. In some embodiments, the TRRAP mutation is C2165T (numbered with reference to SEQ ID NO: 1). In some embodiments, the GRIN2A mutation is a mutation that occurs in the PBP1_iGluR_NMDA_NR2 domain, the Lig_chan domain or the NMDAR2_C domain of GRIN2A. In particular examples, the GRIN2A mutation is selected from one or more of G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G (numbered with reference to SEQ ID NO: 3). In some embodiments, the subject who has the detected mutation is further treated with an anti-melanoma therapy.

Further provided is a method of selecting a therapy for a subject diagnosed with melanoma by detecting the presence or absence of a C2165T mutation in the TRRAP gene (SEQ ID NO: 1). An inhibitor of TRRAP is selected if the C2165T mutation in the TRRAP gene is present. Also provided is a method of selecting a therapy for a subject diagnosed with melanoma, comprising detecting the presence or absence of at least one mutation in the GRIN2A gene disclosed herein. An inhibitor of GRIN2A or a glutamate antagonist is selected for therapy if at least one mutation in GRIN2A is identified.

The present disclosure further provides synthetic oligonucleotides as probes that specifically hybridize with a nucleic acid molecule encoding human TRRAP or human GRIN2A comprising at least one of the mutations disclosed herein. Also provided are arrays comprising a substrate to which are bound one or more of the oligonucleotides specific for mutant TRRAP or mutant GRIN2A. The oligonucleotides may be located at addressable locations on the array.

The foregoing and other objects, features, and advantages of the invention will become more apparent from the following detailed description, which proceeds with reference to the accompanying figures.

BRIEF DESCRIPTION OF THE FIGURES

FIGS. 2A-2J are a series of graphs and immunoblots showing the effect of mutant TRRAP on cell growth. FIG. 2A is a table showing mutant TRRAP induces cell transformation in NIH 3T3 cells. The table shows focus formation of NIH 3T3 cells transfected with the indicated constructs or empty vector control. KRas$^{G12V}$ was included as a positive control for cell transformation. FIG. 2B is an immunoblot showing detection of TRRAP and KRas$^{G12V}$ protein expression in lysates of transiently transfected NIH 3T3 cells. FIG. 2C shows an immunoblot of cell lysates from HEK 293T cells transiently transfected with either control vector or shRNAs that target TRRAP. For normalization, lysates were analyzed in parallel by anti-α-tubulin immunoblotting. FIG. 2D is an anti-TRRAP immunoblot of melanoma cells transduced with shRNA targeting TRRAP. For normalization, lysates were analyzed in parallel by anti-α-tubulin immunoblotting. FIGS. 2E-2H are graphs showing TRRAP mutation confers resistance to apoptosis. The graphs show apoptosis quantification of melanoma cell lines transduced with shRNA control or shRNAs targeting TRRAP. Cells were grown in medium containing 2.5% serum for the indicated times. Apoptosis was assessed by fluorescence microscopy of Hoechst 33258-stained cells. FIGS. 2I and 2J are immunoblots of representative melanoma lines presented in E-H using the indicated antibodies to assess PARP cleavage. WT=wild-type.

FIG. 6 is a sequence comparison of conserved serine-722 of human TRRAP with its orthologs. The human TRRAP orthologs for 12 species were compared using the indicated NCBI accession numbers by COBALT algorithm (available online at ncbi.nlm.nih.gov/tools/cobalt/colbat.cgi). The human TRRAP sequence (amino acids 697-747 of SEQ ID NO: 2) is compared with sequences from *Canis familiaris* (SEQ ID NO: 8), Pan troglodytes (SEQ ID NO: 9), *Bos Taurus* (SEQ ID NO: 10), *Rattus norvegicus* (SEQ ID NO: 11), *Gallus gallus* (SEQ ID NO: 12), *Danio rerio* (SEQ ID NO: 13), *Mus musculus* (SEQ ID NO: 14), *D. melanogaster* (SEQ ID NO: 15), *Anopheles* gamiae (SEQ ID NO: 16), *C. elegans* (SEQ ID NO: 17) and *S. cerevisiae* (SEQ ID NO: 18). The conserved serine at amino acid 722 in humans is underlined and aligned with other species. This residue is not conserved in *C. elegans* or *S. cerevisiae*.

FIGS. 9A-9B is a table showing score cutoff for determination of melanoma somatic mutations.

FIGS. 10A-10D are a series of graphs showing the effect of mutant TRRAP on cell growth. Apoptosis was quantified for melanoma cell lines transduced with shRNA control or shRNAs targeting TRRAP. Cells were grown in medium containing 10% serum for the indicated times. Apoptosis was assessed by fluorescence microscopy of Hoechst 33258-stained cells.

FIGS. 12A-12B are a set of graphs showing GRIN2A functions as a tumor suppressor in melanoma cells. Endogenous GRIN2A was stably depleted in melanoma cells using shRNA specific for human GRIN2A. (A) Proliferation assay of mutant expressing GRIN2A cell lines depleted of endogenous GRIN2A. Knock-down using GRIN2A-specific shRNA (#1, #2 and #3) resulted in little to no change in proliferation for 125T or 501Mel melanoma cell lines. (B) Proliferation assay of wild-type expressing GRIN2A cell lines depleted of GRIN2A. Knock-down resulted in increased proliferation for both 31T and 39T compared to empty vector control (pLKO.1).

FIGS. 13A-13B demonstrate that somatic mutations in GRIN2A have adverse effects on receptor function and formation. (A) Influx of calcium upon NMDA stimulation of transiently transfected HEK293T cells shows decreased calcium permeability in cells expressing mutant forms of GRIN2A. (B) Mutant forms of GRIN2A bind GRIN1 with reduced affinity, thus causing decreased NMDAR complex formation. HEK293T cells were transiently transfected with WT GRIN1 and GRIN2A (WT or mutants) or empty vectors as control and immunoprecipitated with anti-GRIN1. Immunoprecipitates were probed with anti-GRIN2A and anti-GRIN1 to confirm binding. Lysates were probed with anti-GRIN2A and anti-GAPDH as a loading control.

SEQUENCE LISTING

Figure 1:
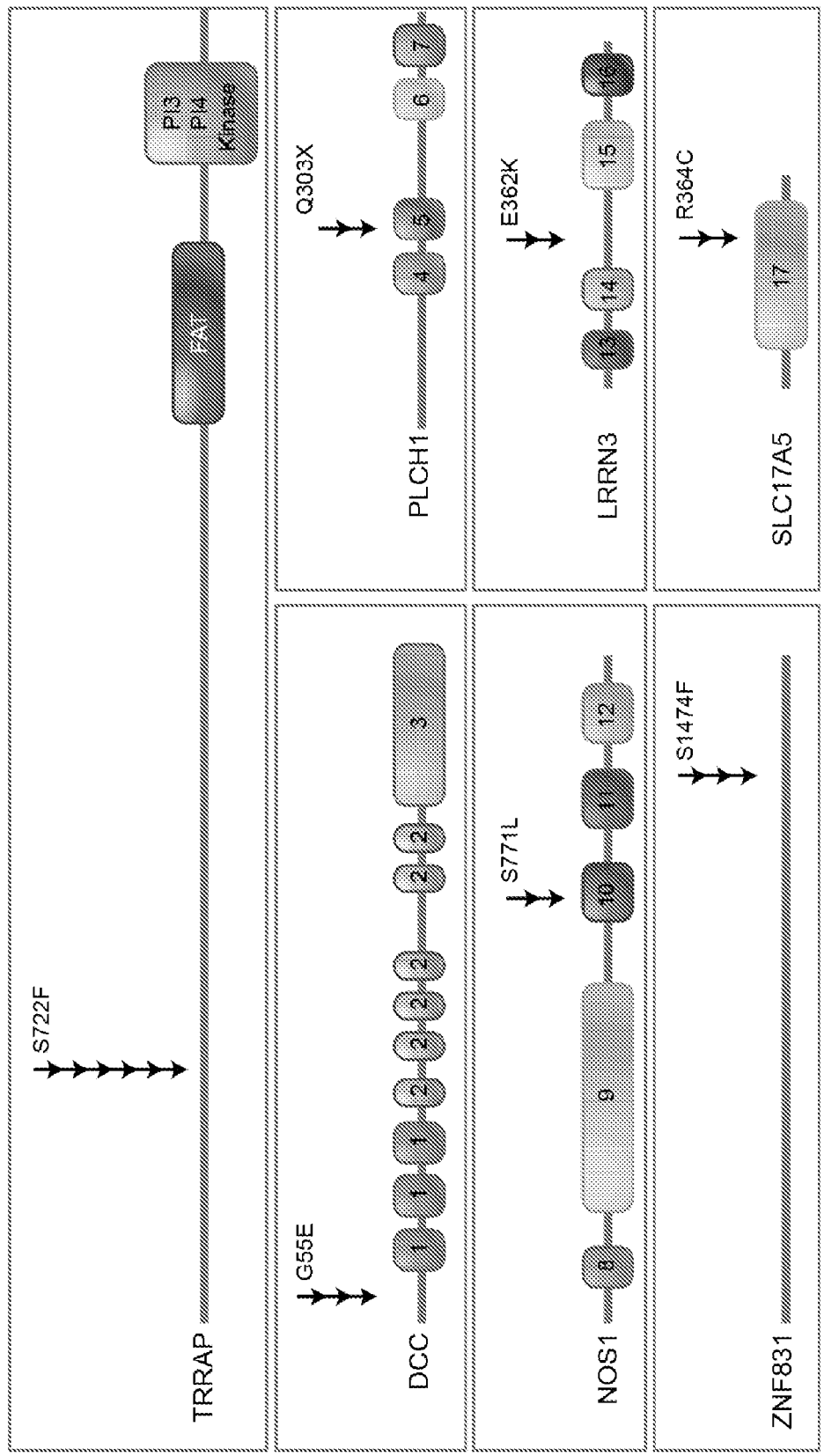
FIG. 1 is a series of schematic illustrations showing the distribution of novel nonsynonymous recurrent mutations in melanoma in TRRAP, DCC, PLCH1, NOS1, LRRN3, ZNF831 and SLC17A5. Seven novel nonsynonymous recurrent mutations identified in the study disclosed herein are presented on relevant protein schematics. Black arrows indicate locations of recurrent mutations and conserved protein functional domains are indicated as boxes (1: Immunoglobulin I-set domain; 2: Fibronectin type III domain; 3: Neogenin C-terminus; 4: Phosphoinositide-specific phospholipase C, efhand-like; 5: Phosphatidylinositol-specific phospholipase C, X domain; 6: Phosphatidylinositol-specific phospholipase C, Y domain; 7: C2 domain; 8: PDZ domain; 9: Nitric oxide synthase, oxygenase domain; 10: Flavodoxin; 11: FAD binding domain; 12: Oxidoreductase NAD-binding domain; 13: LRRNT: Leucine rich repeat N-terminal domain; 14: Leucine Rich Repeat; 15: Immunoglobulin I-set domain; 16: Fibronectin type III domain; 17: Major Facilitator Superfamily).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 15, 2013, 82.7 KB, which is incorporated by reference herein. In the accompanying sequence listing:

SEQ ID NO: 1 is the nucleotide sequence of human TRRAP (CCDS ID 5659.1).

SEQ ID NO: 2 is the amino acid sequence of human TRRAP (CCDS ID 5659.1).

SEQ ID NO: 3 is the nucleotide sequence of human GRIN2A (CCDS ID 10539.1).

SEQ ID NO: 4 is the amino acid sequence of human GRIN2A (CCDS ID 10539.1).

SEQ ID NOs: 5-7 are nucleotide sequences of the region surrounding the TRRAP hotspot mutation from a control sample, a tumor sample and A375 cells, respectively.

SEQ ID NOs: 8-18 are amino acid sequences of a segment of the TRRAP protein from several different species.

SEQ ID NOs: 19-24 are nucleotide sequences of TRRAP primers used for recurrent mutation confirmation.

SEQ ID NOs: 25-62 are nucleotide sequences of GRIN2A primers used for PCR and sequencing.

SEQ ID NOs: 63-66 are nucleotide sequences of TRRAP mutation primers.

SEQ ID NOs: 67-72 are TRRAP-specific shRNA sequences.

DETAILED DESCRIPTION

I. Abbreviations

FBS fetal bovine serum
GRIN2A glutamate receptor, ionotropic, N-methyl D-aspartate 2A
H&E hematoxylin and eosin
iGluR ionotropic glutamate receptor
mGlu metabotropic glutamate receptor
NMDA N-methyl-D-aspartate
PARP poly-ADP ribose polymerase
PCR polymerase chain reaction
RT-PCR reverse transcriptase polymerase chain reaction
shRNA short hairpin RNA
TRRAP transformation/transcription domain-associated protein
WT wild-type II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: The introduction of a composition into a subject by a chosen route. For example, if the chosen route is intravenous, the composition is administered by introducing the composition into a vein of the subject.

Antagonist: A molecule or compound that blocks or inhibits the activity of another molecule or compound (such as a drug that inhibits the function of a protein).

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least two, at least four, at least six, to at least 9, at least 10, at least 14, at least 15, at least 20, at least 30, at least 50, at least 75, at least 100, at least 150, at least 200, at least 300, at least 500, least 550, at least 600, at least 800, at least 1000, or more. In a particular example, an array includes 2-100 addressable locations, such as 4-20 addressable locations. In particular examples, an array consists essentially of oligonucleotide probes specific for the somatic mutations in TRRAP and/or GRIN2A disclosed herein.

In particular examples, an array includes nucleic acid molecules, such as oligonucleotide sequences that are at least 15 nucleotides in length, such as about 15-40 nucleotides in length.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Clinical outcome: Refers to the health status of a patient following treatment for a disease or disorder (such as melanoma), or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient. A decrease in survival also can refer to a decrease in the average time to death in a group, such as a group of patients diagnosed with melanoma.

Diagnosing: Refers to the process of identifying the nature or cause of a disease or disorder.

Glutamate antagonist: Refers to any compound that blocks glutamate function, such as glutamate function mediated through ionotropic glutamate receptors. Thus, suitable glutamate antagonists include, for example, compounds that bind ionotropic glutamate receptors (iGluRs), including NMDA receptors (e.g., GRIN2A). Compounds that bind ionotropic glutamate receptors include compounds which bind α-amino-3-hydroxy-5-methyl-4-isoxazole-propionate (AMPA), NMDA, or kainate receptors in a competitive manner or interact with ionotropic glutamate receptor mediated signals in a non-competitive manner. Other suitable glutamate antagonists include, for example, glutathione promoting agents, GABA stimulating agents and certain neurotransmitters. Glutamate antagonists are known in the art (see, for example, U.S. Patent Application Publication Nos. 2007/0135413 and 2007/0248690). In particular examples, the glutamate antagonist is dizocilpine, GYKI52466, MK-801, AP-5 or CGS 19755 (selfotel).

GRIN2A (glutamate receptor, ionotropic, N-methyl D-aspartate 2A): A subunit of N-methyl-D-aspartate (NMDA) receptors. NMDA receptors are a class of ionotropic glutamate-gated ion channels. These receptors have been shown to be involved in long-term potentiation, an activity-dependent increase in the efficiency of synaptic transmission thought to underlie certain kinds of memory and learning. NMDA receptor channels are heteromeric complexes composed of the key receptor subunit NMDAR1 (GRIN 1) and 1 or more of the 4 NMDAR2 subunits: NMDAR2A (GRIN2A), NMDAR2B (GRIN2B), NMDAR2C (GRIN2C) and NMDAR2D (GRIN2D). GRIN2A, which is also known as NR2A and NMDAR2A, contains the antagonist binding site for glutamate.

GRIN2A sequences are publically available. For example, GenBank Accession Nos. NM_000833 and NP_000824 are the nucleotide and amino acid sequences, respectively, of human GRIN2A transcript variant 2. GenBank Accession Nos. NM_001134407 and NP_001127879 are the nucleotide and amino acid sequences, respectively, of human GRIN2A transcript variant 1. The NCBI CCDS database also provides nucleotide and amino acid sequences for GRIN2A under CCDS ID 10539.1. The GenBank Accession numbers and CCDS ID numbers listed above and disclosed herein are incorporated by reference as they appear in the database as of Dec. 3, 2010.

Disclosed herein are somatic mutations in GRIN2A identified in melanoma tumor samples. The disclosed mutations are referred to by the location of the GRIN2A mutation with reference to SEQ ID NO: 3 (nucleotide) and SEQ ID NO: 4 (amino acid). For example, the C833T mutation refers to a cytosine to thymidine substitution at nucleotide 833 (SEQ ID NO: 3), which results in a serine to phenylalanine change at amino acid 278 (S278F; SEQ ID NO: 4). Some somatic mutations result in the introduction of a stop codon (a nonsense mutation), for example, the G20A GRIN2A mutation. The corresponding amino acid change for the G20A mutation (which occurs at position 7 of SEQ ID NO: 4) is therefore designated W7*.

In some embodiments of the methods disclosed herein, the GRIN2A mutation occurs in a portion of the GRIN2A gene that encodes the PBP1_iGluR_NMDA_NR2 domain; a portion of the GRIN2A gene that encodes the Lig_chan domain; or a portion of the GRIN2A gene that encodes the NMDAR2_C domain. As defined herein, the PBP1_iGluR_NMDA_NR2 domain is encoded by nucleotides 94-1176 of SEQ ID NO: 3 and the amino acid sequence of the PBP1_iGluR_NMDA_NR2 domain corresponds to residues 32-392 of SEQ ID NO: 4; the Lig_chan domain is encoded by nucleotides 1660-2484 of SEQ ID NO: 3 and the amino acid sequence of the Lig_chan domain corresponds to residues 554-828 of SEQ ID NO: 4; and the NMDAR2_C domain is encoded by nucleotides 2515-4392 of SEQ ID NO: 3 and the amino acid sequence of the NMDAR2_C domain corresponds to residues 839-1464 of SEQ ID NO: 4. In some embodiments, the GRIN2A mutation is selected from G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G (SEQ ID NO: 3).

Inhibitor: As used herein, an "inhibitor" refers to any compound that is capable of reducing or altering the expression or activity of a target molecule (such as a nucleic acid molecule or a protein). In some embodiments, the inhibitor is an inhibitor of TRRAP or GRIN2A.

Label: An agent capable of detection, for example by enzyme-linked immunosorbent assay (ELISA), spectrophotometry, flow cytometry or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the label is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and OREGON GREEN™, are characterized by their emission at wavelengths generally in the range of 515-540λ. Red fluorophores, for example TEXAS RED™, Cy5 and tetramethylrhodamine, are characterized by their emission at wavelengths generally in the range of 590-690 λ.

Examples of fluorophores that may be used are provided in U.S. Pat. No. 5,866,366 to Nazarenko et al., and include for instance: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL);

4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (TEXAS RED™): N,N,N', N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other contemplated fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

Melanoma: A form of cancer that originates in melanocytes (cells that make the pigment melanin). Melanocytes are found primarily in the skin, but are also present in the bowel and eye. As used herein, "melanoma" refers to any stage of melanoma, or any subtype of melanoma, such as superficial spreading melanoma, nodular melanoma, acral lentiginous melanoma, lentigo maligna, melanoma-in-situ, mucosal melanoma and uveal melanoma.

Metastasis: Refers to the spread of cancer cells from the original tumor to other sites in the body.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells (such as cancer cells), but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as discussed below, but generally refers to the subset of constitutional alterations that have arisen within the past few generations in a kindred and that are not widely disseminated in a population group.

In some embodiments, a mutation in TRRAP refers to a nucleotide substitution in the TRRAP gene or cDNA, or an amino acid substitution in the TRRAP protein. In some embodiments, a mutation in GRIN2A refers to a nucleotide substitution in the GRIN2A gene or cDNA, or an amino acid substitution in the GRIN2A protein.

Oligonucleotide: A linear polynucleotide sequence of up to about 100 nucleotide bases in length. In some embodiments, the oligonucleotide is 15-40 nucleotides in length.

Patient: As used herein, the term "patient" includes human and non-human animals. The preferred patient for treatment is a human.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: Variant in a sequence of a gene, or any genomic sequence, usually carried from one generation to another in a population. Polymorphisms can be those variations (nucleotide sequence differences) that, while having a different nucleotide sequence, produce functionally equivalent gene products, such as those variations generally found between individuals, different ethnic groups, and geographic locations. The term polymorphism also encompasses variations that produce gene products with altered function, i.e., variants in the gene sequence that lead to gene products that are not functionally equivalent. This term also encompasses variations that produce no gene product, an inactive gene product, a truncated gene product, or increased or increased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNAses, a change in the availability of a site for cleavage by a restriction endonuclease, either the formation of a new site, or lose of a site, and so forth).

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown in the following table.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" or "inhibiting" a disease (such as melanoma) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998). In some embodiments, an "oligonucleotide" is a probe or primer.

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 15-70 nucleotides, 15-60 nucleotides, 15-50 nucleotides, 15-40 nucleotides, or 15-30 nucleotides.

Primers are short nucleic acid molecules, for instance DNA oligonucleotides 15 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, 15-40 nucleotides or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified mutations of interest. PCR primer pairs can be derived from a known sequence by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Prognosis: The likelihood of the clinical outcome for a subject afflicted with a specific disease or disorder. With regard to cancer, the prognosis is a representation of the likelihood (probability) that the subject will survive (such as for one, two, three, four or five years) and/or respond to anti-melanoma treatment, and/or the likelihood (probability) that the tumor will metastasize. A "poor prognosis" indicates a greater than 50% chance that the subject will not survive to a specified time point (such as one, two, three, four or five years), and/or a greater than 50% chance that the tumor will metastasize. In several examples, a poor prognosis indicates that there is a greater than 60%, 70%, 80%, or 90% chance that the subject will not survive and/or a greater than 60%, 70%, 80% or 90% chance that the tumor will metastasize. Conversely, a "good prognosis" indicates a greater than 50% chance that the subject will survive to a specified time point (such as one, two, three, four or five years), and/or a greater than 50% chance that the tumor will not metastasize. In several examples, a good prognosis indicates that there is a greater than 60%, 70%, 80%, or 90% chance that the subject will survive and/or a greater than 60%, 70%, 80% or 90% chance that the tumor will not metastasize.

Sample: A biological specimen containing genomic DNA, RNA, protein, or combinations thereof, obtained from a subject. Examples include, but are not limited to, peripheral blood, urine, saliva, tissue biopsy (such as skin tissue), surgical specimen, and autopsy material. In one example, a sample includes a biopsy of a melanoma tumor or a sample of normal tissue, such as skin tissue (from a subject not afflicted with a known disease or disorder, such as a cancer-free subject).

Specific hybridization: Specific hybridization refers to the binding, duplexing, or hybridizing of a molecule only or substantially only to a particular nucleotide sequence when that sequence is present in a complex mixture (e.g. total cellular DNA or RNA). Specific hybridization may also occur under conditions of varying stringency.

Hybridization conditions resulting in particular degrees of stringency will vary depending upon the nature of the hybridization method of choice and the composition and length of the hybridizing DNA used. Generally, the temperature of hybridization and the ionic strength (especially the Na$^+$ concentration) of the hybridization buffer will determine the stringency of hybridization. Calculations regarding hybridization conditions required for attaining particular degrees of stringency are discussed by Sambrook et al. (In: *Molecular Cloning: A Laboratory Manual*, Cold Spring Harbor, N.Y., 1989 ch. 9 and 11). By way of illustration only, a hybridization experiment may be performed by hybridization of a DNA molecule to a target DNA molecule which has been electrophoresed in an agarose gel and transferred to a nitrocellulose membrane by Southern blotting (Southern, *J. Mol. Biol.* 98:503, 1975), a technique well known in the art and described in Sambrook et al. (*Molecular Cloning: A Laboratory Manual*, Cold Spring Harbor, N.Y., 1989).

Stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25-30° C. are suitable for allele-specific probe hybridizations.

The following is an exemplary set of hybridization conditions and is not meant to be limiting:

Very High Stringency (Detects Sequences that Share 90% Identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Detects Sequences that Share 80% Identity or Greater)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Detects Sequences that Share Greater than 50% Identity)

Hybridization: 6×SSC at RT to 55° C. for 16-20 hours

Wash at least twice: 2×-3×SSC at RT to 55° C. for 20-30 minutes each.

A perfectly matched probe has a sequence perfectly complementary to a particular target sequence. The test probe is typically perfectly complementary to a portion (subsequence) of the target sequence. The term "mismatch probe" refers to probes whose sequence is deliberately selected not to be perfectly complementary to a particular target sequence.

Somatic mutation: An acquired mutation that occurs in a somatic cell (as opposed to a germ cell).

Subject: Living multi-cellular vertebrate organisms, a category that includes both human and non-human mammals. In some embodiments, the subject is a human subject.

Therapeutic agent: A chemical compound, small molecule, or other composition, such as an antisense compound, antibody, peptide or nucleic acid molecule capable of inducing a desired therapeutic or prophylactic effect when properly administered to a subject. For example, therapeutic agents for melanoma include agents that prevent or inhibit development or metastasis of melanoma. In some embodiments, the therapeutic agent is an inhibitor of TRRAP, an inhibitor of GRIN2A or a glutamate antagonist.

Therapeutically effective amount: A quantity of a specific substance sufficient to achieve a desired effect in a subject being treated. For example, a therapeutically effective amount of a therapeutic agent to treat melanoma can refer to the amount necessary to inhibit tumor growth, decrease tumor volume, inhibit tumor metastasis, or prolong survival.

Therapy: The mode of treatment or care of a patient. In some cases, therapy refers to administration of a therapeutic agent. In some embodiments herein, therapy includes administration of an inhibitor of TRRAP, an inhibitor of GRIN2A or a glutamate antagonist. In other examples, therapy includes surgery, such as surgical resection of a melanoma tumor, chemotherapy, radiation therapy, administration of a second therapeutic agent, or any combination thereof.

TRRAP (transformation/transcription domain-associated protein): An adaptor protein found in various multiprotein chromatin complexes with histone acetyltransferase activity, which in turn is responsible for epigenetic transcription activation. TRRAP plays a central role in the transcriptional activity of p53, c-Myc, E2F1 and other transcription factors (McMahon et al., *Cell* 94:363-74, 1998; Barley et al., *Mol Cell* 8:1243-1254, 2001). TRRAP knockout mice are embryonic lethal suggesting that TRRAP is essential for cell survival (Herceg et al., *Nat Genet.* 29:206-11, 2001). Prior studies have suggested that TRRAP may function as an oncogene in pancreatic cancer (Loukopoulos et al., *Cancer Sci* 98(3): 392-400, 2007; Bashyam et al., *Neoplasia* 7(6):556-562, 2005).

TRRAP sequences are publically available. For example, GenBank Accession Nos. NM_003496 and NP_003487 are the nucleotide and amino acid sequences, respectively, of human TRRAP. The NCBI CCDS database also provides nucleotide and amino acid sequences for human TRRAP under CCDS ID 5659.1. The GenBank Accession numbers and CCDS ID numbers listed above and disclosed herein are incorporated by reference as they appear in the database as of Dec. 3, 2010.

Disclosed herein is a recurrent somatic mutation in TRRAP identified in melanoma tumor samples. The disclosed mutation is referred to by the location of the TRRAP mutation with reference to SEQ ID NO: 1 (nucleotide) and SEQ ID NO: 2 (amino acid). Thus, the C2165T mutation refers to a cytosine to thymidine substitution at nucleotide 2165 (SEQ ID NO: 1), which results in a serine to phenylalanine change at amino acid 722 (S722F; SEQ ID NO: 2).

Tumor, neoplasia, malignancy or cancer: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, GenBank Accession numbers and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Described herein is the identification of 68 human genes with an elevated frequency of somatic mutations in melanoma. Nine genes were identified that exhibited recurring mutations in melanoma. In particular, the TRRAP gene was mutated at nucleotide 2165 (C2165T) in six different melanoma tumor samples. In addition, 16 genes were identified that were highly mutated in melanoma samples. The most highly mutated gene identified was GRIN2A, which was mutated in 34% of melanoma tumor samples. The study disclosed herein identified 34 different nonsynonymous somatic mutations in GRIN2A among 36 melanoma tumor samples.

Provided herein is a method of diagnosing a subject as having melanoma, or susceptible to developing melanoma, by detecting at least one mutation in the TRRAP gene or the GRIN2A gene. The presence of the at least one mutation indicates the subject has melanoma or is susceptible to developing melanoma.

In some embodiments, the at least one mutation is in the human TRRAP gene (SEQ ID NO: 1). In particular examples, the mutation is the C2165T mutation in human TRRAP.

In some embodiments, the at least one mutation is in the human GRIN2A gene (SEQ ID NO: 3). In some examples, the mutation occurs in a portion of the GRIN2A gene that encodes the PBP1_iGluR_NMDA_NR2 domain, the Lig_chan domain or the NMDAR2_C domain of human GRIN2A. In other examples, the at least one mutation is G20A, G1346A or T1376C in the GRIN2A gene (SEQ ID NO: 3). In particular examples, the mutation in the portion of the GRIN2A gene that encodes the PBP1_iGluR_NMDA_NR2 domain is C170T, T547A, G754A, C833T, G1028A, G1111A, G1116A or G1117A (SEQ ID NO: 3). In other particular examples, the mutation in the portion of the GRIN2A gene that encodes the Lig_chan domain is A1784G, C1793T, G1959A, G2135A or G2218A (SEQ ID NO: 3). In yet other examples, the mutation in the portion of the GRIN2A gene that encodes the NMDAR2_C domain is G2666A, C2671T, G2759A, C2786T, G2884A, G3217A, C3221T, G3457A, G3523A, G3812A, C3827G, G3854A, C3952T, C4097T, G4261A, C4274T, G4276A or C4385G (SEQ ID NO: 3).

In some embodiments, the at least one mutation is selected from G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G in human GRIN2A (SEQ ID NO: 3). In specific examples, the mutation is a recurring mutation in GRIN2A identified herein, such as C833T, G1111A, G3523A or G3812A (SEQ ID NO: 3).

In some embodiments of the diagnosis methods, detecting the presence or absence of the at least one mutation comprises detecting the presence or absence of the mutation in a skin sample obtained from the subject.

In some embodiments, the method further includes providing a test output (i.e., the result of the test to detect mutations in TRRAP or GRIN2A) to a user (such as a physician or health care worker, the patient or laboratory personnel). In particular examples, the output includes the presence or absence of the at least one mutation, a diagnosis, a treatment recommendation, or any combination thereof. Examples of such output include a printout or display screen that reports the output by displaying it to a clinician to technician. Other examples are electronic medical record reports or other records that include the output in a form discernible to the clinician or technician.

In some embodiments, the subject is further treated with an appropriate therapy, such as with a TRRAP inhibitor (if a mutation in TRRAP is identified), or a GRIN2A inhibitor or glutamate antagonist (if a mutation in GRIN2A is identified). Alternatively or in addition, the appropriate therapy can include administration of a second therapeutic agent known to be effective for the treatment of melanoma, removal of tumor tissue, radiation therapy, chemotherapy, or any combination thereof.

Further provided is a method of selecting a therapy for a subject diagnosed with melanoma by detecting the presence or absence of a C2165T mutation in the TRRAP gene (SEQ ID NO: 1). An inhibitor of TRRAP is selected if the C2165T mutation in the TRRAP gene is present.

Also provided is a method of selecting a therapy for a subject diagnosed with melanoma by detecting the presence or absence of at least one mutation in the GRIN2A gene. An inhibitor of GRIN2A or a glutamate antagonist is selected for therapy if the at least one mutation in GRIN2A is present. In some embodiments, the at least one mutation is (i) a mutation in a portion of the GRIN2A gene that encodes the PBP1_iGluR_NMDA_NR2 domain (nucleotides 94-1176 of SEQ ID NO: 3); (ii) a mutation in a portion of the GRIN2A gene that encodes the Lig_chan domain (nucleotides 1660-2484 of SEQ ID NO: 3); (iii) a mutation in a portion of GRIN2A gene that encodes the NMDAR2_C domain (nucleotides 2515-4392 of SEQ ID NO: 3); (iv) G20A in the GRIN2A gene (SEQ ID NO: 3); (v) G1346A in the GRIN2A gene (SEQ ID NO: 3); or (vi) T1376C in the GRIN2A gene (SEQ ID NO: 3). In some examples, the mutation in the portion of the GRIN2A gene that encodes the PBP1_iGluR_NMDA_NR2 domain is C170T, T547A, G754A, C833T, G1028A, G1111A, G1116A or G1117A (SEQ ID NO: 3). In some examples, the mutation in the portion of the GRIN2A gene that encodes the Lig_chan domain is A1784G, C1793T, G1959A, G2135A or G2218A (SEQ ID NO: 3). In some examples, the mutation in the portion of the GRIN2A gene that encodes the NMDAR2_C domain is G2666A, C2671T, G2759A, C2786T, G2884A, G3217A, C3221T, G3457A, G3523A, G3812A, C3827G, G3854A, C3952T, C4097T, G4261A, C4274T, G4276A or C4385G (SEQ ID NO: 3).

In some embodiments, the method further includes administering the selected therapy. In some instances, the subject is further treated by administration of a second therapeutic agent, surgical removal of tumor tissue, radiation therapy, chemotherapy, or any combination of thereof.

Also provided herein is a method of predicting the prognosis of a subject diagnosed with melanoma by detecting the presence or absence of at least one mutation in the TRRAP gene or the GRIN2A gene. The presence of the at least one mutation indicates the subject has a poor prognosis. In some embodiments, the at least one mutation is selected from C2165T in human TRRAP (SEQ ID NO: 1), or G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G in human GRIN2A (SEQ ID NO: 3). A poor prognosis refers to any negative clinical outcome. For example, in some embodiments, a poor prognosis is an increase in the likelihood of death. In some embodiments, a poor prognosis is an increase in the likelihood of metastasis of the melanoma. In other embodiments, a poor prognosis refers to failure to respond to therapy. The sample can be any appropriate sample from the patient, such as a tissue sample or bodily fluid sample. In particular examples, the sample is a melanoma tumor sample from the subject.

Although mutations in TRRAP and GRIN2A for the diagnosis, prognosis and treatment of melanoma are exemplified herein, the present disclosure contemplates the use of mutations in any of the genes identified herein as mutated in melanoma (see Tables 1-4, 6 and 7 for a list of genes). Thus, in some embodiments of the methods disclosed herein, the method includes detecting at least one mutation selected from any one of the mutations listed in Table 1 or Table 3.

For detection of TRRAP or GRIN2A mutations (or mutations in any other gene mutated in melanoma), nucleic acid (such as DNA or RNA) can be isolated from a biological sample according to well-known methods. In some embodiments, the biological sample is a tissue sample, such as a skin sample or a tumor tissue sample. In other embodiments, the biological sample is a fluid sample, such as blood. For example, nucleic acid can be isolated from cells obtained from a blood sample. In some embodiments, the biological sample is obtained from a patient diagnosed with melanoma or at risk for developing melanoma. In some embodiments, the biological sample is obtained from a control subject.

Methods of detecting mutations in a gene are well known in the art. Detection of one or more mutations in the TRRAP or GRIN2A gene (or any other gene mutated in melanoma) can be accomplished using any suitable technique, such as those described in detail below. For example, TRRAP- or GRIN2A-specific primers can be used to amplify nucleic acid from a biological sample (such as a skin sample, tumor tissue sample or blood sample). The amplified molecule can then be sequenced and compared to a reference TRRAP sequence (such as SEQ ID NO: 1) or a reference GRIN2A sequence (such as SEQ ID NO: 3). Alternatively, the sequence of the amplified molecule can be compared with TRRAP or GRIN2A from a control sample such as a non-cancerous tissue sample. TRRAP and GRIN2A amplification primers and sequencing primers can be designed according to well-known methods. Examples of TRRAP and GRIN2A primers are shown in Table 6 and Table 7. Other suitable primers can be designed using publically available TRRAP or GRIN2A nucleic acid sequences, according to well-known procedures.

Mutations in TRRAP or GRIN2A can also be detected using oligonucleotides that specifically hybridize with a particular mutation. Hybridization of such oligonucleotides can be detected by labeling the oligonucleotide with a detectable marker, such as a fluorescent marker, enzymatic marker or radioisotope. Appropriate output devices for obtaining nucleic acid sequence information or for detecting the presence of a fluorescent or radioactive signal are well known in the art.

Thus, provided herein is an oligonucleotide that specifically hybridizes with a mutant TRRAP nucleic acid molecule or a mutant GRIN2A nucleic acid molecule. In some embodiments, the nucleic acid molecule comprises a mutation selected from (i) C2165T in human TRRAP (SEQ ID NO: 1); and (ii) G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G in human GRIN2A (SEQ ID NO: 3).

The oligonucleotide can be any suitable length to allow for specific hybridization to a target nucleic acid molecule. In some embodiments, the oligonucleotide is about 12 to about 50, about 15 to about 40, about 18 to about 30 or about 20 to about 25 nucleotides in length. In particular examples, the oligonucleotide is about 15 to about 40 nucleotides in length.

In some embodiments, the oligonucleotide includes a label, such as a fluorescent label, an enzymatic label or a radioisotope.

Further provided is an addressable array including an oligonucleotide that specifically hybridizes with a mutant TRRAP nucleic acid molecule disclosed herein or a mutant GRIN2A nucleic acid molecule disclosed herein. In some embodiments, the array includes two or more oligonucleotides that specifically hybridize with a TRRAP nucleic acid comprising a C2165T mutation or with a GRIN2A nucleic acid molecule comprising a mutation selected from G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G in human GRIN2A (SEQ ID NO: 3). In particular examples, the array comprises a plurality of oligonucleotides such that the array comprises at least one oligonucleotide that specifically hybridizes to each of the above listed mutations in TRRAP and GRIN2A. In some examples, the array is a microarray.

IV. Methods of Detecting GRIN2A and TRRAP Mutations

Methods of detecting mutations in genes of interest are known in the art and exemplary methods are described below. Although detection of mutations in the GRIN2A and TRRAP genes is exemplified herein, the techniques described can be applied to other genes and proteins, including other genes identified as mutated in melanoma and disclosed herein (such as those listed in Tables 1-4, 6 and 7).

Detecting mutations in GRIN2A and TRRAP can be accomplished using any technique known in the art. For example, the presence or absence of a GRIN2A or TRRAP mutation can be determined by conventional methods such as gene or RNA detection methods (for example, DNA sequencing, oligonucleotide hybridization, polymerase chain reaction (PCR) amplification with primers specific to the mutation), or protein detection methods (for example, immunoassays or biochemical assays to identify a mutated GRIN2A or TRRAP protein. Generally, the nucleic acid sequence of the GRIN2A or TRRAP gene or RNA in a sample can be detected by any suitable method or technique of detecting gene sequence. Such methods include, but are not limited to, PCR, reverse transcriptase-PCR (RT-PCR), in situ PCR, in situ hybridization, Southern blot, Northern blot, sequence analysis, microarray analysis, or other DNA/RNA hybridization platforms.

Detection of point mutations in target nucleic acids can be accomplished by molecular cloning of the target nucleic acid molecules and sequencing the nucleic acid molecules using techniques well known in the art. Alternatively, amplification techniques such as PCR can be used to amplify target nucleic acid sequences directly from a genomic DNA preparation from a tumor tissue or cell sample. The nucleic acid sequence of the amplified molecules can then be determined to identify mutations. Representative primer pairs that can be used to amplify GRIN2A or TRRAP nucleic acid from a biological sample are listed in Tables 6 and 7. However, design and selection of appropriate primers is well within the abilities of one of ordinary skill in the art.

Ligase chain reaction (Wu et al., *Genomics* 4:560-569, 1989) and allele-specific PCR (Ruano and Kidd, *Nucleic Acids Res.* 17:8392, 1989) can also be used to amplify target nucleic acid sequences. Amplification by allele-specific PCR uses primers that hybridize at their 3' ends to a particular target nucleic acid mutation. If the particular mutation is not present, an amplification product is not observed. Amplification Refractory Mutation System can also be used to detect mutations in nucleic acid sequences (U.S. Pat. No. 5,595,890; Newton et al., *Nucleic Acids Res.* 17:2503-2516, 1989). Insertions and deletions of genes can also be detected by cloning, sequencing and amplification. In addition, restriction fragment length polymorphism probes for the gene or surrounding marker genes can be used to score alteration of an allele or an insertion in a polymorphic fragment. Single stranded conformation polymorphism analysis can also be used to detect base change variants of an allele (Orita et al., *Proc. Natl. Acad. Sci. USA* 86:2766-2770, 1989). Other known techniques for detecting insertions and deletions can also be used with the claimed methods.

Mismatch detection can be used to detect point mutations in a target nucleic acid molecule, such as GRIN2A or TRRAP. Mismatches are hybridized nucleic acid duplexes which are not 100% complementary. The lack of total complementarity can be due to deletions, insertions, inversions, substitutions or frameshift mutations. An example of a mismatch cleavage technique is the RNase protection method, which is described in detail in Winter et al. (*Proc. Natl. Acad. Sci. USA* 82:7575-7579, 1985) and Myers et al. (*Science* 230:1242-1246, 1985). For example, detection of mutations in GRIN2A or TRRAP can involve the use of a labeled riboprobe that is complementary to wild-type GRIN2A or TRRAP. The riboprobe and nucleic acid molecule to be tested (for example, obtained from a tumor sample) are annealed (hybridized) together and subsequently digested with the enzyme RNase A, which is able to detect mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid mRNA or gene, but can a portion of the target nucleic acid, provided it encompasses the position suspected of being mutated. If the riboprobe comprises only a segment of the target nucleic acid mRNA or gene, it may be desirable to use a number of these probes to screen the whole target nucleic acid sequence for mismatches if desired.

In a similar manner, DNA probes can be used to detect mismatches, for example through enzymatic or chemical cleavage (Cotton et al., *Proc. Natl. Acad. Sci. USA* 85: 4397, 1988; Shenk et al., *Proc. Natl. Acad. Sci. USA* 72:989, 1975). Alternatively, mismatches can be detected by shifts in the electrophoretic mobility of mismatched duplexes relative to matched duplexes (Cariello, *Human Genetics* 42:726, 1988). With riboprobes or DNA probes, the target nucleic acid mRNA or DNA which may contain a mutation can be amplified before hybridization. Changes in target nucleic acid DNA can also be detected using Southern hybridization, especially if the changes are gross rearrangements, such as deletions and insertions.

Amplified nucleic acid sequences can also be screened using allele-specific probes. These probes are nucleic acid oligomers, each of which contains a region of the target nucleic acid gene harboring a known mutation. For example, one oligomer may be about 30 nucleotides in length, corresponding to a portion of the target gene sequence. By use of a battery of such allele-specific probes, target nucleic acid amplification products can be screened to identify the presence of a previously identified mutation in the target gene.

Hybridization of allele-specific probes with amplified target nucleic acid sequences can be performed, for example, on a nylon filter. Hybridization to a particular probe under stringent hybridization conditions indicates the presence of the same mutation in the tumor tissue as in the allele-specific probe.

Gene-specific primers are useful for determination of the nucleotide sequence of a target nucleic acid molecule using nucleic acid amplification techniques such as the polymerase chain reaction. Pairs of single stranded DNA primers can be annealed to sequences within or surrounding the target nucleic acid sequence in order to prime amplification of the target sequence. Allele-specific primers can also be used. Such primers anneal only to particular mutant target sequence, and thus will only amplify a product in the presence of the mutant target sequence as a template. In order to facilitate subsequent cloning of amplified sequences, primers may have restriction enzyme site sequences appended to their ends. Such enzymes and sites are well known in the art. The primers themselves can be synthesized using techniques which are well known in the art. Generally, the primers can be made using oligonucleotide synthesizing machines which are commercially available. Design of particular primers is well within the skill of the art. In addition, exemplary GRIN2A and TRRAP primers are provided in Tables 6 and 7.

Nucleic acid probes that hybridize with a GRIN2A or TRRAP nucleic acid molecule, such as a wild-type GRIN2A or TRRAP nucleic acid molecule or a mutant GRIN2A or TRRAP nucleic acid molecule described herein, are useful for a number of purposes. They can be used in Southern hybridization to genomic DNA and in RNase protection assays for detecting point mutations. The probes can also be used to detect target nucleic acid amplification products. GRIN2A or TRRAP probes can also be used to detect mismatches with the wild type gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids (Novack et al., *Proc. Natl. Acad. Sci. USA* 83:586, 1986).

Mutations in nucleic acid molecules can also be detected by screening for alterations of the corresponding protein. For example, monoclonal antibodies immunoreactive with a target gene product can be used to screen a tissue, for example an antibody that is known to bind to a particular mutated position of the gene product (protein). For example, a suitable antibody may be one that binds to a deleted exon or that binds to a conformational epitope comprising a deleted portion of the target protein. Lack of cognate antigen would indicate a mutation. Such immunological assays can be accomplished using any convenient format known in the art, such as Western blot, immunohistochemical assay and ELISA. In some embodiments, the GRIN2A amino acid mutation is selected from W7*, P57L, F1831, D252N, S278F, W343*, E371K, W372*, E373K, G449E, F459S, H595R, S598F, M653I, G712E, G740W, G889E, Q891*, R920K, S929F, E962K, E1073K, P1074L, D1153N, E1175K, W1271*, A1276G, R1285K, R1318W, P1366L, D1421N, S1425L, E1426K and S1462C (SEQ ID NO: 4). In some embodiments, the TRRAP amino acid mutation is S722F (SEQ ID NO: 2).

Mutations in a gene or encoded protein can be evaluated using any technique described above, or any other method known in the art. For example, mutations in a gene or corresponding mRNA can be detecting by direct sequencing of a nucleic acid molecule, detection of an amplification product, microarray analysis or any other DNA/RNA hybridization platform. For detection of mutant proteins, an immunoassay, biochemical assay or microarray can be used.

Any suitable output device or format can be used to transmit the information obtained from the technique used to detect gene or protein mutations. For example, the output device can be a visual output device, such as a computer screen, a printed piece of paper or a written piece of paper. In other examples, the output device can be an auditory output device, such as a speaker. In other examples, the output device is a printer. In some cases, the data is recorded in a patient's electronic medical record. In some embodiments, the results of the test used to identify a mutation are provided to a user (such as a clinician or other health care worker, laboratory personnel, or patient) in a perceivable output that provides information about the results of the test. In some examples, the output is communicated to the user, for example by providing an output via physical, audible or electronic means (for example, by mail, telephone, facsimile transmission, e-mail or communication to an electronic medical record).

In some examples, the output is accompanied by guidelines for interpreting the data, for example, an indication of the likelihood of diagnosis of melanoma. The guidelines need not specify whether melanoma is present or absent, although it may include such a diagnosis. In other examples, the output can provide a recommended therapeutic regimen. For instance, based on the presence of a mutation in the GRIN2A gene, the output can recommend treatment with a GRIN2A inhibitor, or a glutamate antagonist, alone or in combination with other standard cancer treatments, such as surgery, radiation therapy, chemotherapy, or any combination thereof. Similarly, based on the presence of the C2165T mutation in TRRAP, the output can recommend treatment with a TRRAP inhibitor, alone or in combination with any other type of treatment. In some examples, the test may include determination of other clinical information (such as determining the presence or absence of mutations in other genes).

V. Oligonucleotides and Arrays

Provided herein are oligonucleotides that specifically hybridize to a nucleic acid molecule encoding TRRAP or GRIN2A having one or more of the melanoma-associated mutations disclosed herein. Oligonucleotides that specifically hybridize with a TRRAP or GRIN2A nucleic acid comprising a mutation do not hybridize to wild-type (WT) TRRAP or GRIN2A, or hybridization of the oligonucleotide to WT TRRAP or GRIN2A is significantly weaker than hybridization to the mutant TRRAP or GRIN2A. The oligonucleotides described herein can be used, for example, as probes to identify the presence of a mutation in TRRAP or GRIN2A in a sample obtained from a subject suspected of having melanoma. The oligonucleotide probes can further include one or more detectable labels, to permit detection of hybridization signals between the probe and target sequence (such as one of the mutant GRIN2A nucleic acid molecules).

In particular embodiments provided herein, arrays comprising the mutation-specific oligonucleotides as described herein can be used to evaluate the presence or absence of mutations in GRIN2A or TRRAP (or other genes mutated in melanoma).

In some examples, the array comprises an oligonucleotide that specifically hybridizes with a TRRAP nucleic acid molecule comprising the C2165T mutation (SEQ ID NO: 1). In some examples, the array comprises an oligonucleotide that specifically hybridizes with a GRIN2A nucleic acid molecule comprising a mutation selected from G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G in GRIN2A (SEQ ID NO: 3). In particular examples, the array comprises (or further comprises) oligonucleotides that specifically hybridize with additional mutations in GRIN2A or TRRAP. In further examples, the array comprises oligonucleotides that specifically hybridize with mutations in other genes, including those listed in Tables 1-4, 6 and 7. In particular examples, the array contains oligonucleotides that specifically hybridize with each mutation in GRIN2A (G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G), and may further contain at least one oligonucleotide that specifically hybridizes with the C2165T mutation in TRRAP.

In yet further examples, the array comprises one or more oligonucleotides that specifically hybridize with a mutation in TRRAP and/or GRIN2A and further comprises at least one oligonucleotide that specifically hybridizes with another melanoma-associated gene identified herein, such as one or more of the genes listed in Tables 1-4, 6 and 7. In particular, the array may include one or more oligonucleotides to specifically hybridize to one or more of the mutations identified in Table 1 or Table 3.

In some embodiments of the arrays disclosed herein, the array further comprises other oligonucleotides, such as control oligonucleotides or oligonucleotides that specifically hybridize with WT TRRAP or WT GRIN2A. Exemplary control oligonucleotide probes include GAPDH, actin, and YWHAZ, or any probes specific for housekeeping genes.

Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that the areas on the support not occupied by the oligonucleotides are not amenable to non-specific binding, or when non-specific binding occurs, such materials can be readily removed from the surface without removing the oligonucleotides.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microtiter plates (e.g. multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides to a solid support and for directly synthesizing the oligonucleotides onto the support are known to those working in the field; a summary of suitable methods can be found in Matson et al. (Anal. Biochem. 217:306-10, 1994). In one example, the oligonucleotides are synthesized onto the support using conventional chemical techniques for preparing oligonucleotides on solid supports (such as see PCT publications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second(2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

VI. Use of GRIN2A and TRRAP for Diagnosis and Treatment of Melanoma

Using whole exome sequencing of melanoma tumor samples and matched controls, 68 genes were identified with an elevated frequency of somatic mutations in melanoma. In particular, nine genes were identified that exhibited recurring mutations in melanoma (see Table 1). For example, the TRRAP gene was mutated at nucleotide 2165 (C2165T) in six different melanoma tumor samples. In another aspect of the study disclosed herein, 16 genes were identified that were highly mutated in melanoma samples (see Table 3). The most highly mutated gene identified was GRIN2A, which was mutated in 34% of melanoma tumor samples. In total, 34 different nonsynonymous somatic mutations in GRIN2A were identified (FIG. 3A) among 36 melanoma tumor samples.

In light of these findings, disclosed herein is a method of diagnosing melanoma in a subject (or diagnosing a subject as susceptible to developing melanoma) by detecting one or more mutations in the TRRAP gene or the GRIN2A gene. In some embodiments, the at least one mutation is selected from: (i) C2165T in the TRRAP gene (SEQ ID NO: 1); (ii) a mutation in a portion of the GRIN2A gene that encodes the PBP1_iGluR_NMDA_NR2 domain (nucleotides 94-1176 of SEQ ID NO: 3); (iii) a mutation in a portion of the GRIN2A gene that encodes the Lig_chan domain (nucleotides 1660-2484 of SEQ ID NO: 3); (iv) a mutation in a portion of the GRIN2A gene that encodes the NMDAR2_C domain (nucleotides 2515-4392 of SEQ ID NO: 3); (v) G20A in the GRIN2A gene (SEQ ID NO: 3); (vi) G1346A in the GRIN2A gene (SEQ ID NO: 3); and (vii) T1376C in the GRIN2A gene (SEQ ID NO: 3). The presence of the at least one mutation indicates the subject has melanoma or has increased susceptibility to developing melanoma as compared to the general population.

In some examples, the mutation in the portion of the GRIN2A gene that encodes the PBP1_iGluR_NMDA_NR2 domain is C170T, T547A, G754A, C833T, G1028A, G1111A, G1116A or G1117A (SEQ ID NO: 3). In particular examples, the mutation is a recurring mutation identified herein, such as C833T or G1111A (SEQ ID NO: 3).

In other examples, the mutation in the portion of the GRIN2A gene that encodes the Lig_chan domain is A1784G, C1793T, G1959A, G2135A or G2218A (SEQ ID NO: 3).

In yet other examples, the mutation in the portion of the GRIN2A gene that encodes the NMDAR2_C domain is G2666A, C2671T, G2759A, C2786T, G2884A, G3217A, C3221T, G3457A, G3523A, G3812A, C3827G, G3854A, C3952T, C4097T, G4261A, C4274T, G4276A or C4385G (SEQ ID NO: 3). In particular examples, the mutation is a recurring mutation identified herein, such as G3523A or G3812A (SEQ ID NO: 3).

In some embodiments, the subject is further treated with an appropriate therapy, such as with a TRRAP inhibitor (if a mutation in TRRAP is identified), or a GRIN2A inhibitor or glutamate antagonist (if a mutation in GRIN2A is identified).

Also provided are a method of treating a subject with melanoma harboring a mutation in the TRRAP gene by administering an inhibitor of TRRAP, and a method of treating a subject with melanoma harboring a mutation in the GRIN2A gene by administering an inhibitor of GRIN2A or a glutamate antagonist. Further provided is a method of selecting a patient with melanoma as a candidate for treatment with a TRRAP inhibitor by detecting the C2165T mutation in the patient. Also provided is a method of selecting a patient with melanoma as a candidate for treatment with a GRIN2A inhibitor or glutamate antagonist by detecting the G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A or C4385G GRIN2A mutation in the patient. A method of predicting the prognosis of a subject with melanoma by detecting one or more mutations in GRIN2A or TRRAP is also provided.

In some embodiments disclosed herein, the detection of the C2165T TRRAP mutation and/or one or more GRIN2A mutations selected from G20A, C170T, T547A, G754A, C833T, G1028A, G1111A, G1116A, G1117A, G1346A, T1376C, A1784G, C1793T, G1959A, G2135A, G2218A, G2666A, C2671T, G2759A, C2786T, G2884A, G3217A, C3221T, G3457A, G3523A, G3812A, C3827G, G3854A, C3952T, C4097T, G4261A, C4274T, G4276A and C4385G (SEQ ID NO: 3) can be used as a clinical tool to diagnose a patient that has already developed melanoma, or who has an increased risk of developing melanoma. Detection of one or more of the above-listed mutations can also be used to determine the prognosis of a patient previously diagnosed with melanoma. The presence of one or more of the disclosed mutations indicates a subject has already developed melanoma or is susceptible to developing melanoma.

Detection of one or more of the disclosed mutations in TRRAP and GRIN2A can also be used as a tool for determining an appropriate therapy for a subject with melanoma. The presence of one or mutations in GRIN2A indicates the subject is a candidate for treatment with a GRIN2A inhibitor or a glutamate antagonist. The presence of the C2165T mutation in TRRAP indicates the subject is a candidate for treatment with a TRRAP inhibitor.

Subjects diagnosed with melanoma and treated with a TRRAP inhibitor, a GRIN2A inhibitor or glutamate antagonist can further be treated with a second therapeutic agent known to be effective for the treatment of melanoma. Alternatively, or in addition, the subject with melanoma can be further treated by surgical removal of tumor tissue, chemotherapy, radiation therapy, or any combination thereof.

The following examples are provided to illustrate certain particular features and/or embodiments. These examples should not be construed to limit the disclosure to the particular features or embodiments described.

EXAMPLES

Example 1

Materials and Methods

This example describes the experimental procedures for the studies described in Example 2.

Tumor Tissues

The tissue and melanoma cell lines used for the Discovery and Prevalence Screen in this study were described previously (Palavalli et al., *Nat Genet* 41:518-520, 2009). Tissues used for Validation set 1 were fresh frozen melanoma tumors obtained from the University of Colorado Denver Skin Cancer Biorepository, Division of Medical Oncology. Tissue was collected at University of Colorado Hospital, Anschutz Medical Campus, under Institutional Review Board protocols. Macrodissection was conducted using a dissection microscope. Isolation of DNA from tumor enriched isolates has been previously described online at riedlab.nci.nih.gov. Tissue processing and storage were previously described by Morente et al. (*Eur J Cancer* 42:2684-2691, 2006). Tissues used for Validation set 2 were obtained from Optimum Cutting Temperature (OCT)—embedded frozen clinical specimens from the Melanoma Informatics, Tissue Resource, and Pathology Core (MelCore) at The University of Texas MD Anderson Cancer Center under Institutional Review Board-approved protocols. H&E-guided dissection and isolation of DNA from the tumor-enriched isolates has been described previously (Davies et al., *Clin Cancer Res* 15:7538-7546, 2009). The clinical information associated with the melanoma tumors used in this study is provided in Table 5.

Exome Capture

Exome capture was performed using the Human All Exon System (Agilent Technologies, Santa Clara, Calif.). The manufacturer's protocol for SURESELECT™ Human All Exon System (Illumina Paired-End Sequencing Library Prep) version 1.0.1 was used, with the modifications listed below. Bioanalyzer steps were either performed using agarose gel or omitted. In the sample preparation step 9, samples were purified using AMPURE™ XP beads (Agencourt/Beckman Coulter Genomics, Danvers, Mass.) according to the manufacturer's protocols. In step 12, samples were purified with the QIAQUICK™ MINELUTE™ kit (Qiagen Inc., Valencia, Calif.). One column was used for each sample—the four 250 µL post-amplification aliquots were pooled, and passed over the column in several spin steps. Samples were eluted in 12 µL buffer EB, and quantitated using the QUBIT™ dsDNA BR Assay kit (Invitrogen Corp, Carlsbad, Calif.). In the post-hybridization amplification step 2, samples were purified with AMPURE™ XP beads as described above. Samples were then eluted in 30 µL buffer EB.

Illumina Sequencing

Sequencing was performed on the Illumina GAIIx platform according to the manufacturer's instructions. 76 base paired-end reads were generated.

Read Mapping and Variant Analysis

Reads were initially aligned using ELAND lumina Inc, San Diego, Calif.). ELAND alignments were used to place reads in bins of about 5 million base pairs. Unmapped reads were placed in the bin of the mate pair if the mate was mapped. Cross_match (a general purpose program for comparing any two DNA sequence sets; see website phrap.org) was utilized to align the reads assigned to each bin to the corresponding ~5 Mb of genomic sequence. Cross_match alignments were converted to the SamTools bam format, and then genotypes were called using bam2mpg (Teer et al., *Genome Res* 20(10):1420-1431, 2010; see website research.nhgri.nih.gov/software/bam2mpg). Bam2mpg was used to implement the Most Probable Genotype (MPG) algorithm, a Bayesian based method to determine the probability of each genotype given the data observed at that position. The quality score represents the difference of the log likelihoods of the most and second most probable genotype. The MPG was divided by the coverage at each position to calculate the MPG/coverage ratio.

To eliminate common germline mutations from consideration, alterations observed in dbSNP130 or in a high quality set of common variants from the 1000 genomes 11_2010 data release project were removed. To perform the 1000 genomes project filtering, low coverage genome data from 629 individuals was obtained from the November 2010 data release of the 1000 genomes project (available online at trace.ncbi.nih.gov/1000genomes/ftp/release/2010_11/ALL.2of4intersection.20100804.sites.vcf.gz). From this list of variants, those positions called by at least 3 of the 4 analysis methods used by the project were included. The list was further limited to those variants above 5% minor allele frequency. Polymorphisms were further removed by examination of the sequence of the gene in genomic DNA from matched normal tissue. Genotypes were annotated as described in Biesecker et al. (*Genome Res* 19:1665-1674, 2009). "Type of Mutation" definitions are as follows: synonymous: in a protein coding region, but does not change the amino acid; nonsynonymous: in a protein coding region; missense variant: changes amino acid; nonsense variant, stop: introduces a stop codon; DIV-c: an in-frame deletion/insertion variant in a coding region; and DIV-fs: a frameshifting deletion/insertion variant in a coding region.

Statistical Analysis of Mutated Genes

To determine which of the genes in the Discovery Screen were more likely to be drivers, two metrics were calculated to assess the frequency and probability of mutations. The first method considered the frequency of mutations in the Discovery Screen, which was calculated by dividing the total number of nonsynonymous mutations observed by the total number of base pairs sequenced. The second method fit a binomial distribution based on the number of base pairs sequenced for the gene of interest, the number of mutations observed, and the background rate of mutation. For the background rate, the observed rate in the exome screen was used, 11.2 mutations per megabase. Based on these methods, 16 genes were selected for validation.

PCR, Sequencing and Mutational Analysis of Melanoma Samples

Genes identified to harbor recurrent mutations were confirmed and further screened using two primer sets listed in Table 6 in an additional 153 melanoma samples. A subset of 16 genes which were mutated in the Discovery Screen was selected for analysis in the Prevalence Screen using criteria described herein. These genes were amplified and sequenced in an additional 38 melanoma samples using the primers listed in Table 6 and Table 7. BRAF was only evaluated for the V600E alteration. Mutational analysis, confirmation and determination of somatic status were carried out as previously described (Prickett et al., *Nat Genet.* 41:1127-1132, 2009; Palavalli et al., *Nat Genet.* 41:518-520, 2009; Viloria et al., *Cancer Res* 69:4926-4934, 2009). Sequence traces of the Validation Screen were analyzed using the Mutation Surveyor software package and all genes had 93% coverage or above (SoftGenetics, State College, Pa.).

Plasmid Cloning

A TRRAP expressing construct in CβSBS vector was used. Mutant TRRAP was generated using an overlapping two-fragment PCR mediated strategy using PHUSION™ High- Fidelity polymerase (New England Biolabs, Ipswich, Mass.). Forward and reverse CDS mutation-containing oligonucleotides of 21-26 by in length were designed with the corresponding mutation centrally located within the oligonucleotide. These primer pairs were used in two independent PCR reactions with wild-type TRRAP plasmid as a template as follows:

(1) TRRAP-F(3+)-
CAGATGGTGAAAGGAATGCTC (SEQ ID NO: 63)

Mutation-R-
GCAAAGAGGAAGACAGAGCCAAAG (SEQ ID NO: 64)

(2) Mutation-F-
CTTTGGCTCTGTCTTCCTCTTTGC (SEQ ID NO: 65)

TRRAP-R(7-)-
GTTCATAACAACATGCACACAG (SEQ ID NO: 66)

PCR products purified by gel purification were used as a template for PCR using TRRAP-F and -R primer pairs to generate a TRRAP mutation bearing product. The TRRAP mutation bearing PCR product was cut with BbvC1 and Kas1 restriction enzymes and was inserted in the TRRAP-CβSBS plasmid. Sequence verified mutant TRRAP was subsequently used in various experiments.

Cell Culture and Transient Expression

Metastatic melanoma tumor lines were maintained as previously described. HEK 293T cells were purchased from ATCC (Manassas, Va.) and maintained in complete Dulbecco's Modified Eagles Medium supplemented with 10% fetal bovine serum (FBS), 1× non-essential amino acids, 2 mM L-glutamine, and 0.75% sodium bicarbonate. Sk-Mel-28 and A375 cells were purchased from the National Cancer Institute, Division of Cancer Treatment, Developmental Therapeutics Program (Frederick, Md.) and maintained in RPMI-1640 and supplemented with 10% FBS.

Western Blotting

Transfected cells or stable pooled clones were gently washed 3× in PBS and then lysed using 0.5-1.0 ml 1% NP-40 lysis buffer (1% NP-40, 50 mM Tris-HCl pH 7.5, 150 mM NaCl, complete protease inhibitor tablet, EDTA-free (Roche, Indianapolis, Ind.), 1 µM sodium orthovanadate, 1 mM sodium fluoride, and 0.1% β-mercaptoethanol) per T-75 flask for 20 minutes on ice. Lysed cells were scraped and transferred into a 1.5 mL microcentrifuge tube followed by brief sonication. Whole cell extracts lysed with 2×SDS sample buffer were subjected to SDS-PAGE and western blotted for TRRAP expression. Primary antibodies used in the analysis were anti-TRRAP antibody (Cell Signaling, Cat. No. 3966S), anti-PARP antibody (Cell Signaling, Cat. No. 9542) and anti-alpha-tubulin antibody (Calbiochem-EMD Biosciences, Cat. No. 555627).

Lentiviral shRNA

Constructs for stable depletion of TRRAP (Catalog Number RHS4533, Construct Numbers TRCN0000005361, TRCN0000005362) were obtained from Open Biosystems (Huntsville, Ala.) and were confirmed to efficiently knockdown TRRAP at the protein level. Lentiviral stocks were prepared as previously described (Prickett et al., *Nat Genet.* 41:1127-1132, 2009). Melanoma cell lines (63T, 17T, A375, and Sk-Mel-28) were infected with shRNA lentiviruses for each condition (vector and a TRRAP specific shRNA). Selection and growth were performed as described above. Hairpin sequence for TRCN0000005361 was CCGGCGTGTAA-GAAAGGGAGAATATCTCGAGATATTCTC-CCTTTCTTACA CGTTTTT (SEQ ID NO: 67), mature sense for TRCN0000005361 was CGTGTAAGAAAGG-GAGAATAT (SEQ ID NO: 68), mature antisense for TRCN0000005361 was ATATTCTCCCTTTCTTACACG (SEQ ID NO: 69); hairpin sequence for TRCN0000005362 was CCGGGCCCTGTTCTTTCGCTTTGTACTC-GAGTACAAAGCGAAAGAACAG GCTTTTT (SEQ ID NO: 70), mature sense for TRCN0000005362 was GCCCT-GTTCTTTCGCTTTGTA (SEQ ID NO: 71), mature antisense for TRCN0000005362 was TACAAAGCGAAAGAA-CAGGGC (SEQ ID NO: 72).

Apoptosis Measurement

Cells were collected by incubation in trypsin/EDTA followed by centrifugation and were fixed in a solution containing 3.7% formaldehyde, 0.5% NP40, and 10 µg/ml Hoechst 33258 in PBS. Apoptotic indices were determined by visual scoring of at least 300 nuclei.

NIH 3T3 Transformation Assay

For each plasmid (CβSBS, CβSBS-TRRAP (wt), CβSBS-TRRAP (S722F), and Ras$^{G12V}$), 3 µg of plasmid was transfected using the calcium phosphate precipitation method into NIH 3T3 cells cultured in T25 flasks. Twenty-four hours after transfection, 1-5% of transfected cells were seeded into T25 flasks and cultured in normal growth medium containing 2.5% FBS for 14-20 days. The flasks were scored by visually scoring under a microscope for foci formation.

Pathway Analysis

In order to explore the combined effects of groups of genes that were mutated in the melanoma exome analysis, group and pathways analysis was performed on different sets of genes. Three sources of gene sets were selected, including Gene Ontology (available online at geneontology.org), Kyoto Encyclopedia of Genes and Genomes (available online at genome.jp/kegg), and MSigDB (available online at broadinstitute.org/gsea/msigdb), containing 10147, 214, and 1892 groups respectively, when these studies were performed. The sets included groups based on molecular function, cellular localization, biological processes, and signaling pathways. For each of the group of genes, the respective genes in the exome analysis were examined and it was assessed whether mutations were observed. Several different statistics were then calculated to accentuate different aspects of the analysis. First, the number of genes that were successfully sequenced in the study was compared to the number that was mutated. This proportion was then compared to the background rate of 3308 genes mutated in the total of 16,768 genes using a hypergeometric distribution. As the purpose was for ranking, no multiple comparison correction was implemented. Second, the average number of nonsynonymous mutations observed for the mutated genes was examined by dividing the total number of nonsynonymous mutations into the total number of genes observed to be mutated. Third, a binomial calculation was used. For each group of genes the total number of mutations observed and the number of base pairs that were successfully sequenced was determined. The P-value was calculated as the probability of a group having at least as many mutations as were observed, given the numbers of base pairs sequenced and the background passenger frequencies, using the binomial distribution in R (available online at r-project.org). The background passenger frequencies were conservatively estimated as the total numbers of mutations observed the whole exome study divided by the total number of base pairs sequenced in the study (i.e., assuming that all of the mutations observed were passengers).

Example 2

Whole Exome Sequencing Identifies TRRAP Hotspot Mutations and GRIN2A as Frequently Mutated in Melanoma An exome re-sequencing was conducted of 14 matched normal and metastatic tumor DNAs from untreated melanoma patients. Exonic sequences were enriched with Agilent's SURESELECT™ technology for targeted exon capture (Gnirke et al., *Nat Biotechnol* 27:182-189, 2009), targeting 37 Mb of sequence from exons and flanking regions in nearly 20,000 genes. Sequencing was performed with the Illumina GAii platform, and reads were aligned by using ELAND (Illumina, Inc. San Diego Calif.) followed by cross_match (see website phrap.org) to the reference human genome (Build 36.1). On average, 12 Gb of sequence was generated per sample to a mean depth of 180× or greater to achieve exome builds with at least 90% of the exons covered by high quality genotype calls. To eliminate common germline mutations from consideration, any potential somatic mutation that was observed in dbSNP130, or in a high quality set of common variants from the 1000 genomes project, was removed. To determine which of these alterations were somatic (i.e. tumor-specific), the particular gene in the whole exome sequence derived from genomic DNA from the matched normal tissue was examined. From these putative alterations, 5161 potential somatic mutations in 3568 different genes were identified in the fourteen samples sequenced.

A major challenge of such studies is discriminating true mutations from the large number of possible sequence alterations identified. Several bioinformatic and experimental steps were used to discriminate between these possibilities. A previously described Bayesian genotype caller, MPG, was used to call genotypes (available online at research.nhgri.nih.gov/software/bam2 mpg) (Teer et al., *Genome Res* 20(10): 1420-1431, 2010). Empirical testing against Sanger-based sequencing was employed to set a score cutoff above which the alterations could be trusted. A total of 91 regions were amplified by PCR from the relevant melanoma genomic DNA sample using specific primers and directly sequenced with dye-terminator chemistry. It was determined whether a mutation was somatic by examining the sequence of the gene in genomic DNA from matched normal tissue. From the 91 sequences obtained, 47 were confirmed and 44 were not. Looking for differences between matched tissue samples will select for both somatic variants, and sequencing errors, resulting in a higher non-confirmation rate.

The analysis was further refined by examining the relationship between the MPG quality score and depth of coverage at each position. The quality score should rise with increasing amounts of sequence covering a given position. When the score does not rise with increasing depth of coverage, this suggests a false genotype call. As indicated in FIG. 9, all the confirmed alterations correlated with a MPG/coverage ratio of 0.5 or above in both the tumor and matched normal samples, with only one exception. In contrast, 91% of the alterations that were not confirmed by Sanger sequencing, had a MPG/coverage ratio below 0.5 in either the tumor or the normal or both. Thus, of the 91 assessed alterations, using 0.5 as a cutoff, 46 somatic alterations, using 0.5 as a cutoff, 46 somatic alterations out of 47 were identified by conventional sequencing, indicating a 97.9% coverage rate and a 2.4% false negative rate. All of the future analyses therefore relate to alterations that obtained a MPG/coverage ratio of 0.5 or above in both the tumor and normal samples. Using the 0.5 ratio cutoff, of 47 somatic substitutions that were discovered prior to this study in these samples, 38 were present in the whole exome study, giving a sensitivity of 81%.

The analysis tools described above removed ~18% of the alterations, leaving 4228 somatic base substitutions for further scrutiny. A total of 3872 were heterozygous alterations and 356 changes were loss of heterozygosity. Of these alterations, 2813 caused amino acid changes (nonsynonymous), including 2589 that were missense, 175 nonsense and 49 occurred at splice sites. There were 1387 silent (synonymous) substitutions. A total of 19 small deletions and 9 insertions were observed.

The observed somatic mutations could either be 'driver' mutations that have a role in melanoma neoplasia or functionally inert 'passenger' changes. In this whole exome screen, 2813 nonsynonymous and 1387 synonymous mutations were identified, yielding a ratio of nonsynonymous to synonymous changes (N/S ratio) of 2.0:1; which is not higher than the N/S ratio of 2.5:1 predicted for nonselected passenger mutations (Sjoblom et al., *Science* 314:268-274, 2006), suggesting that most of these alterations are likely to be 'passenger' mutations. The number of C>T mutations was significantly greater than the numbers of other nucleotide substitutions, resulting in a high prevalence of C>T/G>A transitions (P<0.001; FIG. 9). Finally, a total of 116 dinucleotide substitutions were observed, of these, 59 were CC>TT/GG>AA changes, all consistent with the previously documented ultraviolet light exposure signature (Greenman et al., *Nature* 446:153-158, 2007).

Figure 5:
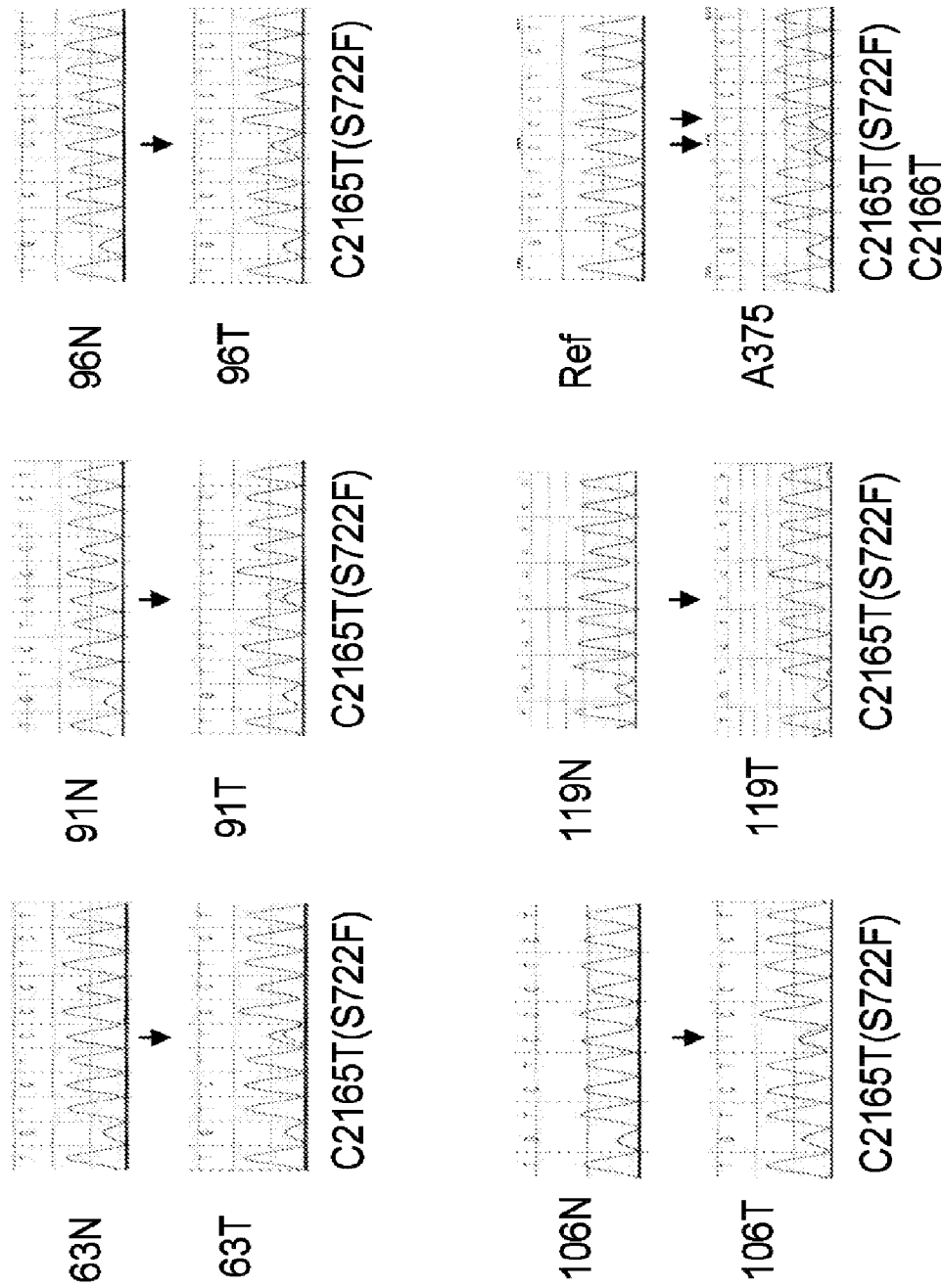
FIG. 5 is a series of chromatograms showing a recurrent hotspot mutation in TRRAP in representative melanoma tumor samples and the commercially available A375 cell line. In each case, the top sequence chromatogram was obtained from normal tissue and the lower sequence chromatogram from the indicated tumors. Arrows indicate the location of the missense mutations. The nucleotide and amino acid alterations are indicated below the chromatograms. The sequences shown in the chromatograms are TGTCTCCCTCT (SEQ ID NO: 5) for normal tissue; TGTCTYCCTCT (SEQ ID NO: 6) for tumor samples; and TGTCTYYCTCT (SEQ ID NO: 7) for the A375 cell line.

To search for novel recurrent mutations, alterations that occurred in two or more of the fourteen samples subjected to whole exome sequencing were examined. From this analysis, as expected, the BRAF V600E alteration was captured in 7 out of the fourteen samples. In addition to BRAF, nine more genes were found to harbor a recurrent mutation. Seven of the novel recurrent mutations were nonsynonymous and two were synonymous (Table 1). Further screening of the novel hotspot mutations in an additional 153 melanomas identified DCC and ZNF831 to have a third recurring mutation each. Strikingly, TRRAP, encoding the transformation/transcription domain-associated protein, contained four additional cases that harbored the recurrent mutation (FIG. 1 and FIG. 5), one of which was found in the commercially available cell line, A375. All 6 nonsynonymous alterations in TRRAP had the same point mutation, a change of a cytosine to a thymine at position 2165 of the TRRAP transcript (uc003upp.1), leading to the replacement of a serine with a phenylalanine at amino acid residue 722 of the protein (S722F).

Subsequent sequence analysis of all coding exons of TRRAP in 25 additional melanomas revealed no additional nonsynonymous alterations. The positions of the mutations in TRRAP imply that they are likely to be oncogenic as no truncating mutations were observed and 100% of the alterations occurred in one location. In addition, the affected residue is highly conserved evolutionarily (FIG. 6) and SIFT (sorting intolerant from tolerant) analysis (Ng and Henikoff, *Nucleic Acids Res* 31:3812-3814, 2003) of the TRRAP mutation gave it a score of 0.00 (median information content 2.71), predicting that the mutation alters protein function. The clustering of somatic missense mutations is similar to that observed for activating mutations, such as RAS (Bos et al., *Nature* 327:293-297, 1987), BRAF (Davies et al., *Nature* 417:949-954, 2002), and PIK3CA (Samuels et al., *Science* 304:554, 2004), suggesting that TRRAP may be a novel oncogene.

TRRAP functions as part of a multiprotein co-activator complex possessing histone acetyltranferase activity that is central for the transcriptional activity of p53, c-Myc, E2F1 and other transcription factors (McMahon et al., Cell 94:363-374, 1998; Barley et al., Mol Cell 8:1243-1254, 2001). TRRAP knockout mice are embryonic lethal indicating that TRRAP is essential for cell survival (Herceg et al., Nat Genet. 29:206-211, 2001).

To asses if melanoma cells harboring endogenous TRRAP mutations are dependent on TRRAP for survival, short hairpin RNA (shRNA) was used to stably knock-down TRRAP protein levels in melanoma cells harboring either wild-type TRRAP(SK-Mel28 and 17T) or mutant TRRAP (63T and A375). Specific targeting of TRRAP was confirmed by TRRAP immunoblotting of transiently transfected HEK293T cells as well as one of the melanoma cell lines (FIGS. 2C and 2D). The various cell clones were grown in 10% or 2.5% serum to test cell viability. The unique shRNA constructs targeting TRRAP had minimal effect on the survival of cells expressing wild-type TRRAP but substantially increased apoptosis rates of melanoma lines carrying mutant TRRAP, particularly when the clones were grown in low serum conditions (FIGS. 2E-2H and FIG. 10). These results were further corroborated by western blot analysis of cell lysates from the analyzed cells showing increased levels of cleaved PARP specifically in mutant cells that have been knocked down for TRRAP compared to vector control as well as TRRAP wild-type cells (FIGS. 2I-2J). Thus, mutant TRRAP is essential for melanoma cell survival which is consistent with previous results showing that TRRAP has a role in cell viability (Herceg et al., Nat Genet. 29:206-211, 2001; Ard et al., Mol Cell Biol 22:5650-5661, 2002).

To further demonstrate the prevalence and spectrum of somatic mutations in genes identified in the whole exome Discovery Screen, genes were selected that had more mutations than expected using the observed mutation rate (binomial p-value<0.05) and were mutated in more than two Discovery Screen samples. Sixteen such genes were identified and analyzed for mutations in an additional 38 melanoma samples using PCR amplification and Sanger sequencing. Gene coverage in the Prevalence Screen was 93% and above. This effort involved 9165 PCR and sequencing reactions encompassing 5.4 Mb of tumor DNA. A total of 65 putative changes were identified in the Prevalence Screen (Table 2).

This list of sixteen genes, which, except for BRAF, had not previously been identified as playing a role in melanoma, was found to scale up and harbor an increasing number of somatic mutations in the Prevalence Screen which correlated with the initial frequency identified in the Discovery Screen (Table 2 and Table 3).

The most highly mutated genes out the 16 validated genes were GRIN2A (33%), TMEM132B (17.3%), ZNF831 (17.3%) and PLCB4 (15.4%). The transmembrane protein TMEM132B, as well as the Zinc Finger protein ZNF831 whose functions have as yet not been determined, contained only heterozygous mutations and harbored recurrent mutations G822E and S 1474F, respectively. PLCB4, which encodes phosphoinositide phospholipase C-beta-4 that catalyzes the formation of inositol 1,4,5-trisphosphate and diacylglycerol from phosphatidylinositol 4,5-bisphosphate using calcium as a cofactor, is known to play an important role in the intracellular transduction of multiple extracellular signals in response to activation of G protein-coupled receptors (GPCRs) (Rebecchi and Pentyala, Physiol Rev 80:1291-1335, 2000). SIFT analysis of the different missense mutations identified in the novel highly mutated genes, predicts that a large fraction of the alterations would affect protein function (Table 4).

The most frequently mutated of the validated fourteen genes, GRIN2A, on chromosome 16p13.2, encodes a glutamate [N-methyl-(D)-aspartic acid (NMDA)] receptor subunit epsilon-1 that is part of the class of ionotropic glutamate receptors. The NMDA receptor is a heterotrimeric channel composed of three different subunits, GRIN1 (NR1), GRIN2A or GRIN2B (NR2) and GRIN3 (NR3). GRIN2A bears the agonist binding site for glutamate (Johnson and Ascher, Nature 325:529-531, 1987). The ligand-gated channel is permeable to cations including $Ca^{2+}$, and at resting membrane potential, NMDA receptors are inactive due to a voltage-dependent blockade of the channel pore by $Mg^{2+}$. NMDA receptor activation, which requires binding of glutamate and glycine, leads to an influx of $Ca^{2+}$ and increased cAMP production.

Figure 7:
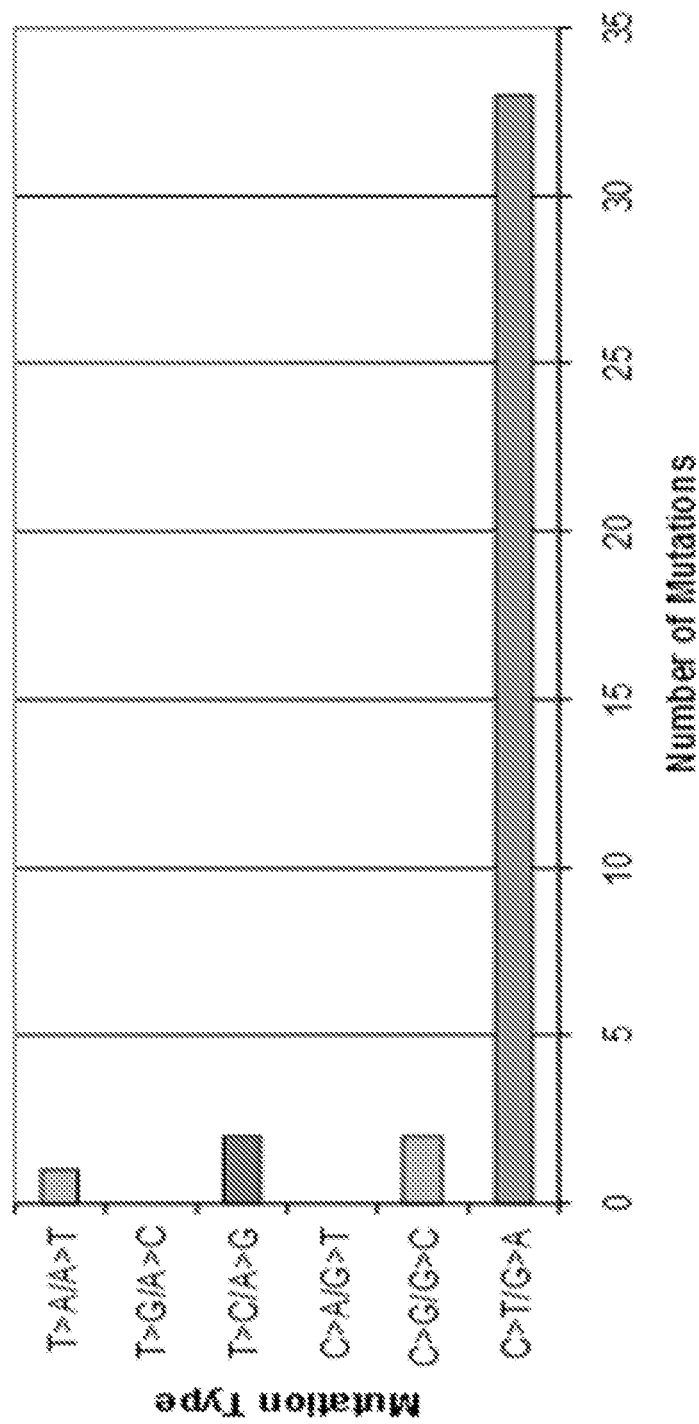
FIG. 7 is a graph showing mutation spectra of single base pair substitutions in GRIN2A. The number of each of the six classes of base substitutions resulting in nonsynonymous changes in GRIN2A is shown.
Figure 8:
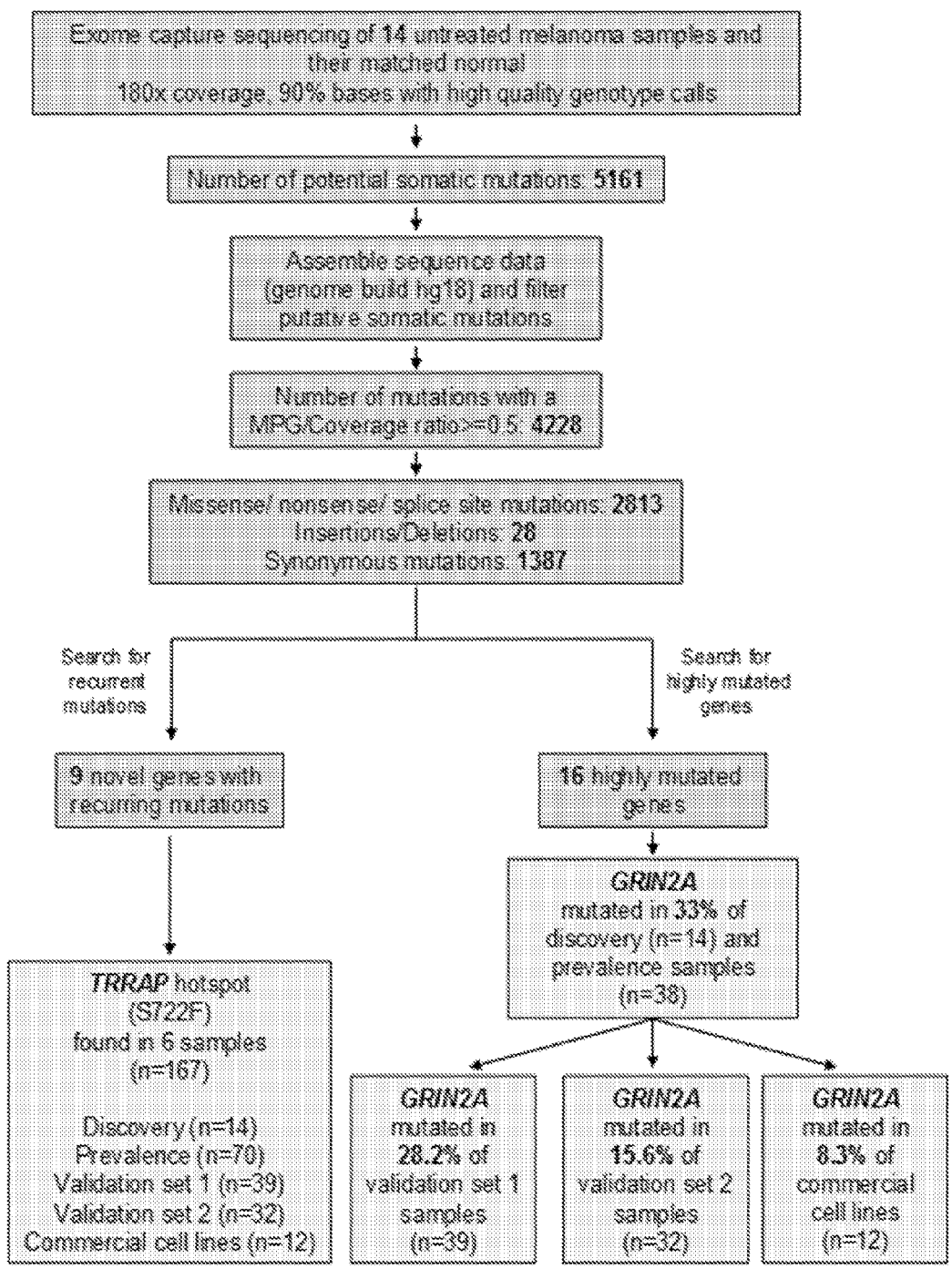
FIG. 8 is a schematic of the whole exome capture and sequencing analysis of 14 melanoma samples.

GRIN2A, which was found to be mutated in 6 of the 14 melanomas in the Discovery Screen, was found to harbor an additional 11 somatic mutations in the Prevalence Screen. In addition to the Discovery and Prevalence Screen samples, GRIN2A somatic mutations were searched for in two independent additional validation panel sets from untreated melanoma patients. Validation panel set 1, which included 39 melanomas, revealed 11 tumors with somatic mutations affecting 28.2% of the tumors examined and validation panel set 2, which included 32 melanomas, identified 7 GRIN2A somatic mutations affecting 15.6% of cases. Lastly, GRIN2A sequencing in 12 commercially available cell lines revealed a mutation in 501Mel. In total, 34 distinct GRIN2A mutations were identified in 135 samples affecting 25.2% of melanoma cases (Table 3). The number of C>T mutations identified in GRIN2A was significantly greater than the numbers of other nucleotide substitutions, resulting in a high prevalence of C>T/G>A transitions (P<1×0.001; FIG. 7), reproducing previously reported mutation signatures in melanoma (Greenman et al., Nature 446:153-158, 2007). FIG. 8 depicts the various genetic and analysis stages used in this whole exome study.

Figure 3A:
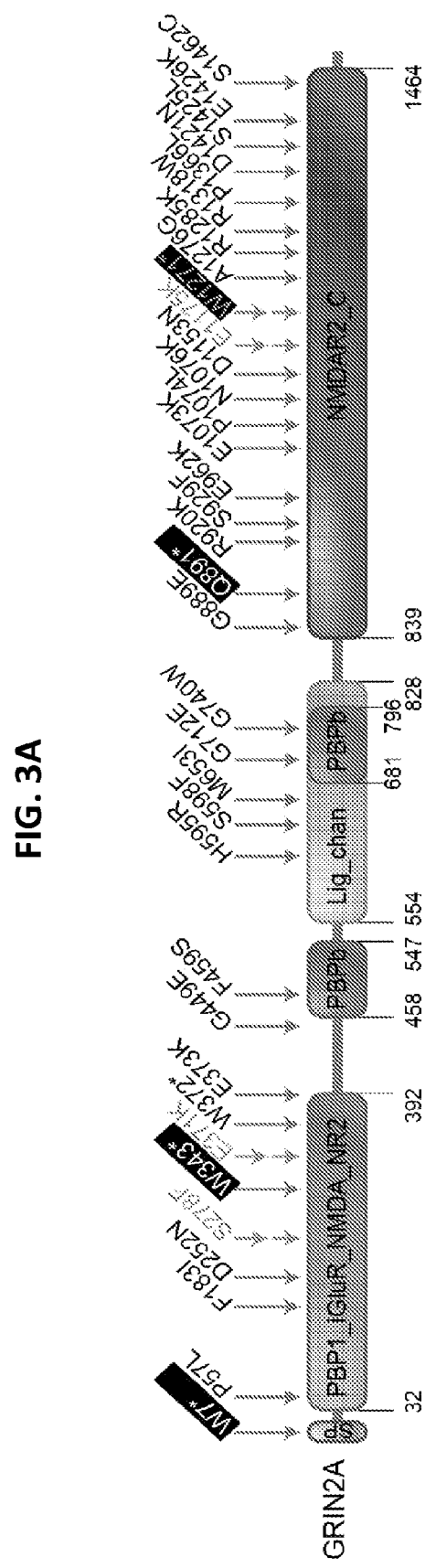
FIG. 3A is a schematic illustration showing the locations of somatic mutations in GRIN2A. Human GRIN2A protein is presented with conserved functional domains indicated (SP: Signal peptide; PBP1_iGluR_NMDA_NR2: N-terminal leucine/isoleucine/valine-binding protein LIVBP-like domain of the NR2 subunit of NMDA receptor family; Lig_chan: Ligand-gated ion channel; NMDAR2_C: N-methyl D-aspartate receptor 2B3 C-terminus). Somatic mutations are indicated with arrows and the amino acid changes are listed. Recurrent mutations in GRIN2A are S278F, E371K and E1175K. Nonsense mutations are indicated by black boxes.

The location of the discovered GRIN2A mutations is summarized in FIG. 3A. Clustering of somatic mutations is seen in regions of GRIN2A encoding various of its functional domains, and two particular clusters can be observed surrounding amino acids 371, 372, and 373 in the PBP1 iGluR NMDA NR2 domain and amino acids 1073, 1074 and 1076 in the NMDAR2C domain. In addition, three recurrent alterations were observed (S278F, E371K and E1175K). One of these recurrent mutations (E1175K) occurred in the commercially available cell line 501Mel. The affected residues within these clusters are highly conserved evolutionarily and SIFT analysis of the different missense mutations on GRIN2A predicts that over 51% of the missense alterations would affect protein function (Table 4). In addition to these missense alterations, five nonsense mutations were identified, which would cause polypeptide truncation.

The nature of somatic mutations in tumors may aid in classifying the identified genes to oncogenes or tumor suppressor genes (Vogelstein and Kinzler, Nat Med 10:789-799, 2004). Generally, oncogenes harbor adjacent recurrent mutations in different tumors; the mutations are nearly always missense and the mutations commonly affect only one allele. Tumor suppressor genes are generally mutated throughout the coding region of the gene, many of the mutations truncate the protein and the mutations generally affect both alleles. Based on this classification the mechanism by which somatic mutations in GRIN2A have a tumorigenic effect is unclear;

however, the frequency and nature of the discovered alterations strongly suggest that mutations in GRIN2A play a major role in melanoma tumorigenesis.

The comprehensive nature of the acquired data in this study provided an opportunity to determine whether any particular novel gene pathways and functional groups have a significant role in melanoma. Using pathways from Gene Ontology (available online at geneontology.org), Kyoto Encyclopedia of Genes and Genomes (available online at genome.jp/kegg), and MSigDB (available online at broadinstitute.org/gsea/msigdb), different statistical metrics were recalculated based on the total number of mutations from all genes within each group, the number of different genes mutated, the combined sizes of the genes in each group, and the total number of tumors examined (see methods in Example 1). From this analysis, one particular pathway was highly significant—the glutamate signaling pathway.

Glutamate is known to activate two different types of receptors: ionotropic glutamate receptors (iGluRs) and metabotropic glutamate receptors (mGlus). iGluRs are ligand-gated ion channels that allow cations such as calcium and potassium to pass through the plasma membrane of the cell after binding of glutamate to the receptors. iGluRs are subdivided into three receptor types according to agonists response, one of which is N-methyl-D-aspartate (NMDA) (Hollmann and Heinemann, *Annu Rev Neurosci* 17:31-108, 1994). Thus, GRIN2A, the most highly mutated gene in the screen encodes a glutamate receptor subunit which binds NMDA. In addition, PLCB4, which is a down-stream protein involved in metabotropic glutamate receptor-related signal transduction which leads to inositol phosphate production and protein kinase C (PKC) activation (Pin et al., *Biochem Soc Trans* 23:91-96, 1995) was also highly mutated in the screen.

Figure 3B:
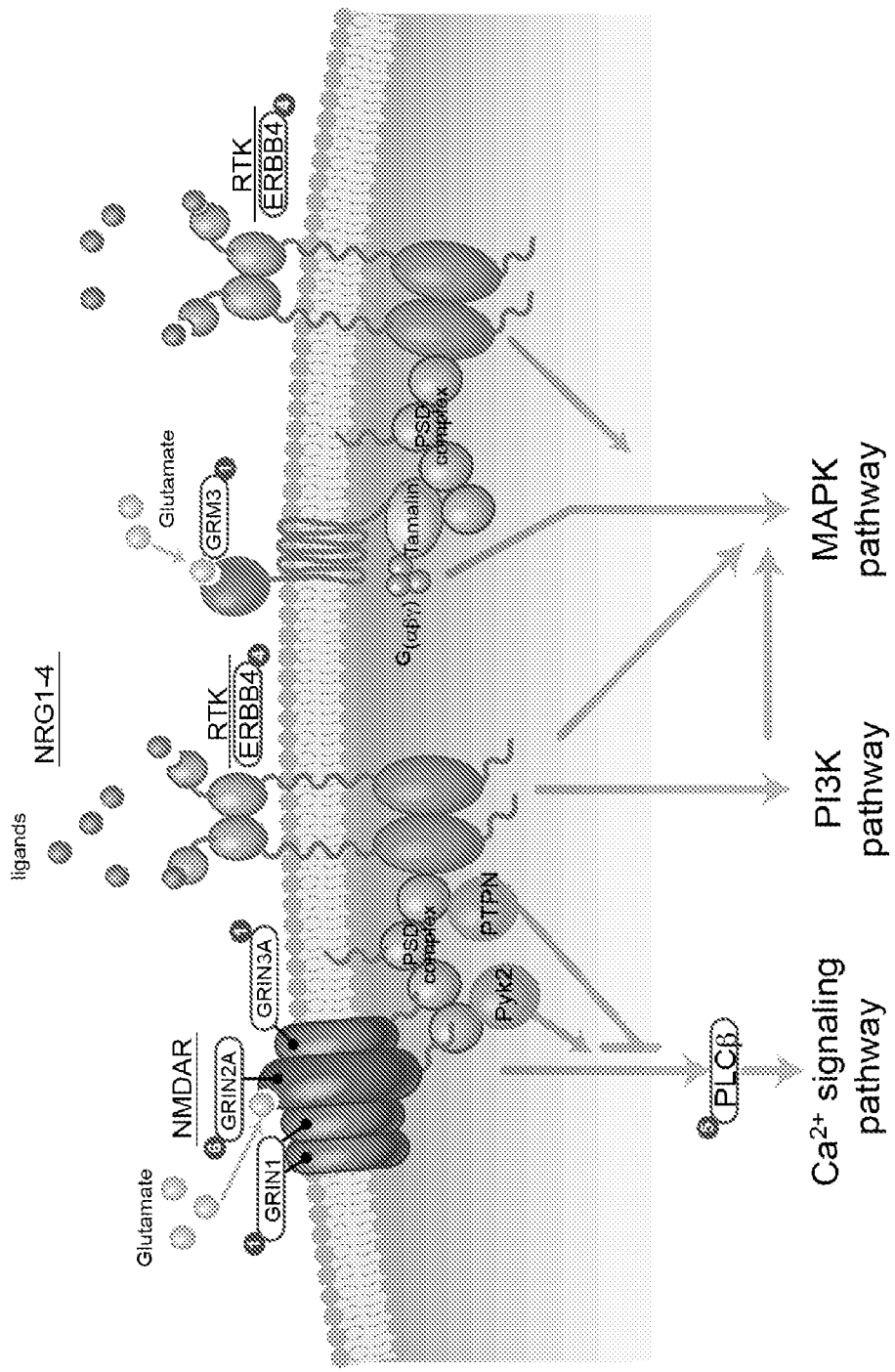
FIG. 3B is a schematic illustration showing glutamate signaling pathway mutations in melanoma. The genes that function in glutamate signaling are specified. Circled genes have somatic mutations. The number of mutations in each gene is indicated by the number adjacent to the circle (PSD complex: post synaptic density complex; NMDAR: N-methyl-D-aspartic acid (NMDA) receptor; RTK: receptor tyrosine kinase).
Figure 4:
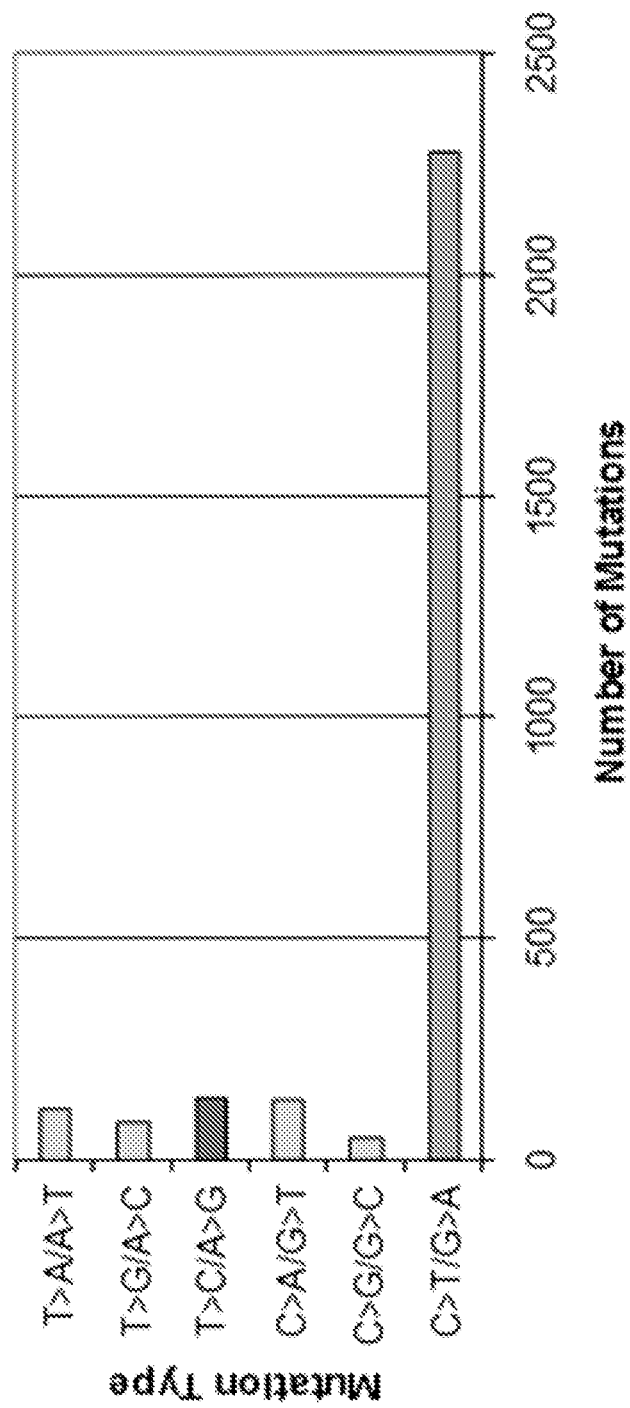
FIG. 4 is a graph showing mutation spectra of single base pair substitutions in melanoma whole exome sequencing. The number of each of the six classes of base substitutions resulting in nonsynonymous changes in the whole exome screen is shown.

Genetic analysis of the G protein coupled receptor family in melanoma determined that GRM3, which belongs to the metabotropic glutamate receptors and is also activated by glutamate, is mutated in 16% of melanoma cases. In this study as well, the GRM-signaling downstream-effector, PLCB4 is activated and hydrolyses phosphatidylinositol 4,5-bisphosphate and generates inositol 1,4,5-trisphosphate. Finally, a recent survey of genetic alteration of the tyrosine kinome in melanoma has pointed to ERBB4, Pyk2 and the Ephrin receptors to be highly mutated in melanoma (Prickett et al., *Nat Genet.* 41:1127-1132, 2009). ERBB4 and its ligand NRG1, Pyk2 as well as the Ephrins, have been shown to play a crucial role in modulation of NMDA receptor signaling (Anton et al., *Nat Neurosci* 7:1319-328, 2004; Rieff et al., *J Neurosci* 19:10757-10766, 1999; Ozaki et al., *Nature* 390:691-694, 1997; Dalva et al., *Cell* 103:945-956, 2000). Thus, molecular and genetic studies have implicated cross-talk between NRG1-ERBB4, GRM3, Ephrin signaling and glutamate receptor functions. Interestingly, a link between the glutamate pathway and tumor genesis has been seen in neuronal tumors, where glioma cells releasing an excess of glutamate, showed more aggressive growth than parental glioma cells (Takano et al., *Nat Med* 7:1010-1015, 2001). Furthermore, previous reports showing that ectopic expression of the metabotropic glutamate receptor GRM1 results in melanocytes transformation in mice (Pollock et al., *Nat Genet.* 34:108-112, 2003) and that expression of GRM1 is sufficient to induce full transformation of immortalized melanocytes (Shin et al., *Pigment Cell Melanoma Res* 21:368-378, 2008) also implicate glutamate signaling in melanoma. A pathway schematic summarizing these various components in the glutamate pathway is depicted in FIG. 3B.

The study disclosed herein presents the most complete demonstration of melanoma exome alterations to date and provides a number of important genetic insights into melanoma. The comprehensive nature of the study allows one to: (1) identify TRRAP as an unexpected target of recurring genetic alterations, (2) reveal genes that were not previously connected with melanoma, one of which, GRIN2A is one of the most highly mutated in melanoma to date and (3) demonstrate that a majority of melanoma tumors had alterations in genes encoding members of the glutamate pathway.

Example 3

Mutations in GRIN2A Increase Anchorage-Independent Growth and Adversely Affect Receptor Function This example describes studies to evaluate the functional effect of somatic mutations in GRIN2A.

Figure 11B:
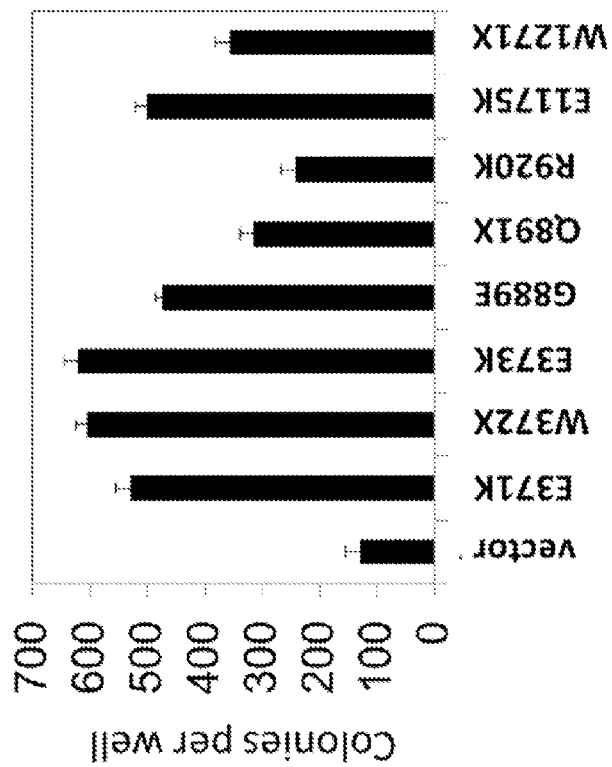
FIGS. 11A-11B demonstrate that melanoma cells expressing mutant forms of GRIN2A have increased ability for anchorage-independent growth. Melanoma cells (A375 cells) stably expressing GRIN1 and GRIN2A mutants, or empty vector, were seeded into soft agar in 10% serum and grown for 14 days before staining and counting (A). Also shown is a quantitative graph of colony formation of A375 cells in soft agar (B). Error bars are representative of n=3 (s.d.).
Figure 11A:
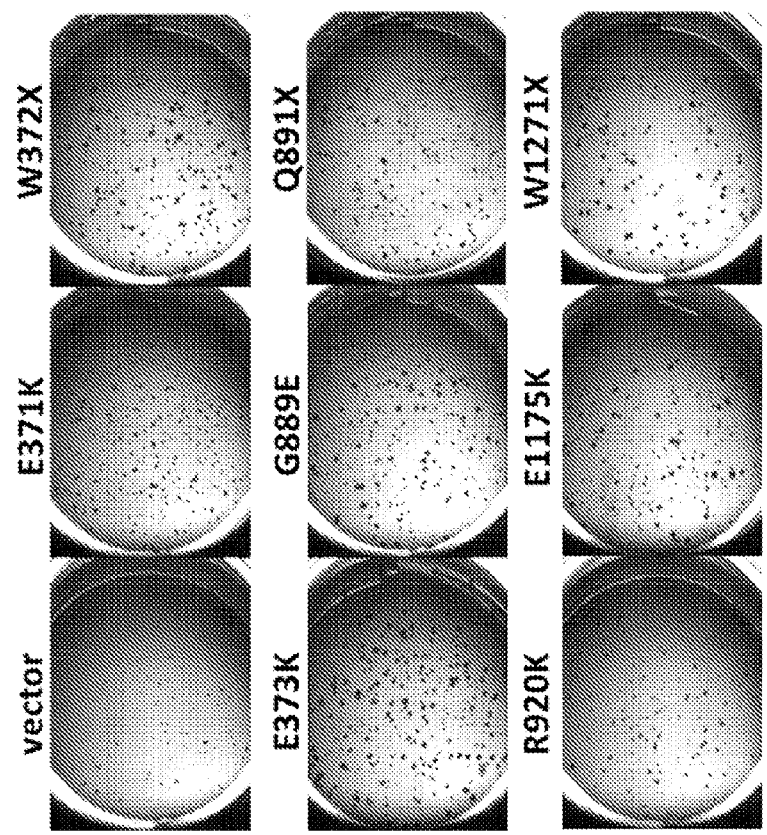

Melanoma cell lines (2359 and A375 cell lines) stably expressing both GRIN1 and a mutant GRIN2A (E371K, W372X, E373K, G889E, W1271X, Q891X, R9020K or E1175K) were generated. Expression of GRIN1 and mutant GRIN2A protein was confirmed by Western blot. To test the effect of stable expression of mutant GRIN2A on anchorage-independent growth, melanoma cell lines 2359 and A375 stably expressing GRIN1 and a mutant GRIN2A were seeded into soft agar in 10% serum and grown for 14 days before staining and counting. A375 colonies are shown in FIG. 11A. As shown in FIG. 11B, colony formation significantly increased in A375 melanoma cells expressing mutant GRIN2A, compared with cells expressing empty vector. Similar results were obtained for 2359 melanoma cells.

Figure 12B:
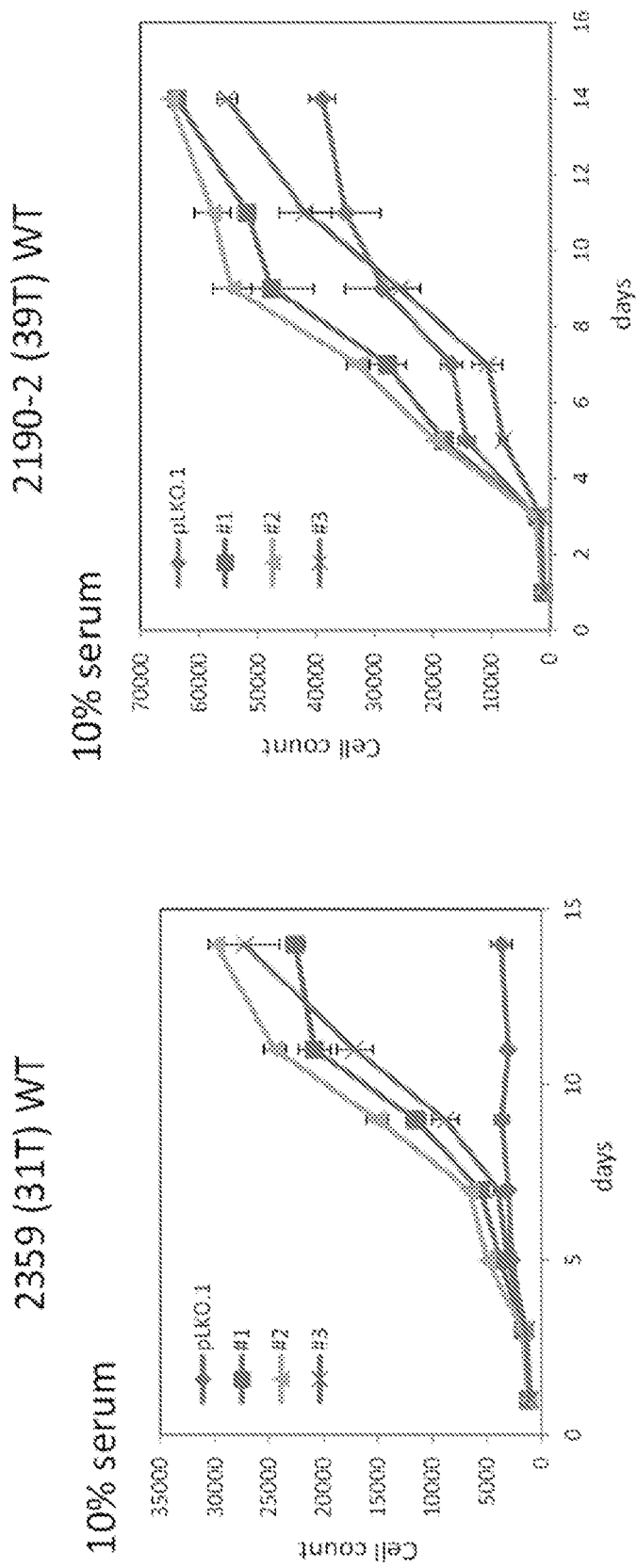

To test if melanoma cell lines are dependent on GRIN2A for survival, endogenous GRIN2A message was stably depleted using several different specific shRNA for human GRIN2A. Depletion of message was confirmed by qRT-PCR. Lentiviral stocks were prepared as previously described (Prickett et al., *Nat Genet.* 41:1127-1132, 2009). Melanoma cell lines (501Mel and 125T) were infected with control (pLKO.1) and GRIN2A specific shRNA lentiviruses (#1, #2 and #3). Selection and growth were carried out as previously described (Palavalli et al., *Nat Genet.* 41:518-520, 2009). Knock-down of endogenous GRIN2A in cells expressing mutant forms of GRIN2A had little to no effect on proliferation (FIG. 12A). However, depletion of GRIN2A in cells expressing endogenous wild-type GRIN2A resulted in increased cell proliferation (FIG. 12B). These results demonstrate that GRIN2A functions as a tumor suppressor in melanoma cells.

Figure 13B:
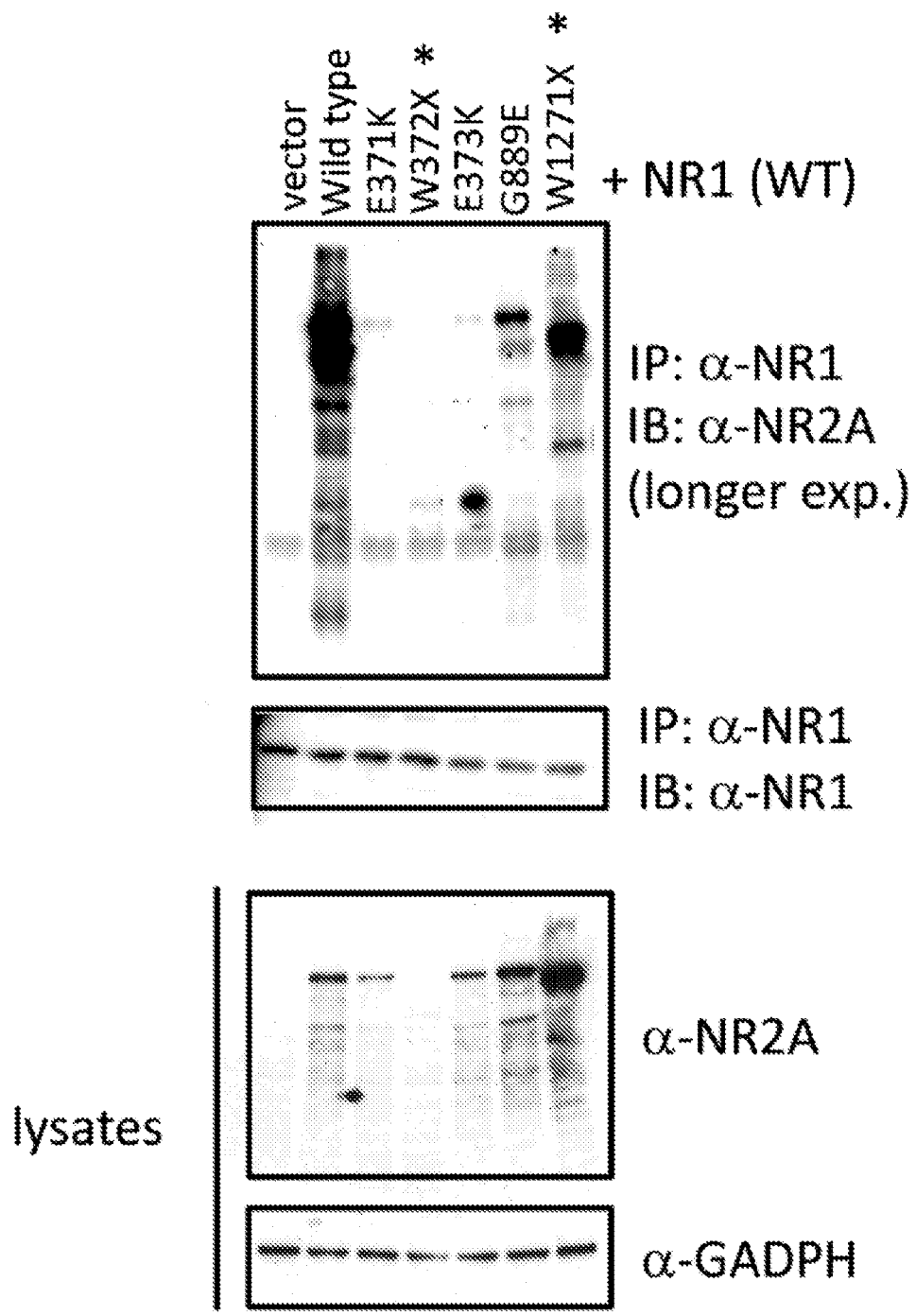

The effect of mutant GRIN2A on receptor function was also evaluated. As shown in FIG. 13A, influx of calcium upon NMDA stimulation of transiently transfected HEK293T cells decreased calcium permeability in cells expressing mutant forms of GRIN2A. It was also demonstrated that mutant forms of GRIN2A bind GRIN1 with reduced affinity, thus causing decreased NMDAR complex formation (FIG. 13B). Thus, somatic mutations in GRIN2A have adverse effects on receptor function and formation.

TABLE 1

Recurrent mutations identified in melanoma whole exome sequencing

| Gene Name | # of Tumors Affected | Nucleotide Change | Amino Acid Change | Synonymous or Non_Synonymous | Tumor Name | Tumor Panel |
|---|---|---|---|---|---|---|
| BRAF | 7 | T1799A | V600E | Nonsynonymous | 1T | Exome Capture |
| | | | | | 5T | Exome Capture |
| | | | | | 9T | Exome Capture |
| | | | | | 22T | Exome Capture |
| | | | | | 35T | Exome Capture |
| | | | | | 51T | Exome Capture |
| | | | | | 91T | Exome Capture |
| CPT1A | 2 | C1638T | F546F | Synonymous | 5T | Exome Capture |
| | | | | | 43T | Exome Capture |
| DCC | 3 | G164A | G55E | Nonsynonymous | 12T | Exome Capture |
| | | | | | 18T | Exome Capture |
| | | | | | MB1160_T | Validation set 1 |
| FCRL1 | 3 | C741T | I247I | Synonymous | 91T | Exome Capture |
| | | | | | 96T | Exome Capture |
| | | | | | 63T | Prevalence screen |
| LRRN3 | 2 | G1084A | E362K | Nonsynonymous | 12T | Exome Capture |
| | | | | | 24T | Exome Capture |
| NOS1 | 2 | C2312T | S771L | Nonsynonymous | 24T | Exome Capture |
| | | | | | 60T | Exome Capture |
| PLCH1 | 2 | C907T | Q303X | Nonsynonymous | 1T | Exome Capture |
| | | | | | 24T | Exome Capture |
| SLC17A5 | 2 | C1090T | R364C | Nonsynonymous | 12T | Exome Capture |
| | | | | | 18T | Exome Capture |
| TRRAP | 6 | C2165T | S722F | Nonsynonymous | 63T | Exome Capture |
| | | | | | 91T | Exome Capture |
| | | | | | 96T | Prevalence screen |
| | | | | | 106T | Prevalence screen |
| | | | | | 119T | Prevalence screen |
| | | | | | A375 | Commercial cell line |
| ZNF831 | 3 | C4421T | S1474F | Nonsynonymous | 43T | Exome Capture |
| | | | | | 91T | Exome Capture |
| | | | | | MB1160_T | Validation set 1 |

Samples used in exome capture and prevalance screen were obtained from The Surgery Branch, National Cancer Institute. Validation set 1 samples were obtained from The Division of Medical Oncology, University of Colorado Denver School of Medicine. A375 is a commercially available melanoma cell line.

TABLE 2

Sixteen highly mutated genes in melanoma

| | | | Exome Capture | | | Prevalence Screen | | | Combined Exome Capture and Prevalence Screens | | |
|---|---|---|---|---|---|---|---|---|---|---|---|
| Gene name | ucsc ID | P value | No. of mutations | No. of tumors affected | % of tumors affected | No. of mutations | No. of tumors affected | % of tumors affected | No. of mutations | No. of tumors affected | % of tumors affected |
| BRAF | uc003vwc.2 | 4.80E−05 | 7 | 7 | 50.0% | 27 | 27 | 69.2% | 34 | 34 | 64.2% |
| GRIN2A | uc002czq.1 | 6.36E−03 | 6 | 6 | 42.9% | 12 | 12 | 30.8% | 18 | 18 | 34.0% |
| CCDC63 | uc001trv.1 | 3.34E−03 | 4 | 4 | 28.6% | 2 | 2 | 5.1% | 6 | 6 | 11.3% |
| TMEM132B | uc001uhe.1 | 7.59E−03 | 5 | 4 | 28.6% | 5 | 5 | 12.8% | 10 | 9 | 17.0% |
| ZNF831 | uc002yan.1 | 1.29E−02 | 5 | 4 | 28.6% | 5 | 5 | 12.8% | 10 | 9 | 17.0% |
| PLCB4 | uc010gbx.1 | 4.39E−02 | 5 | 4 | 28.6% | 4 | 4 | 10.3% | 9 | 8 | 15.1% |
| AKR1B10 | uc003vrr.1 | 5.21E−03 | 3 | 3 | 21.4% | 1 | 1 | 2.6% | 4 | 4 | 7.5% |
| TAS2R60 | uc003wdb.1 | 5.46E−03 | 4 | 3 | 21.4% | 2 | 2 | 5.1% | 6 | 5 | 9.4% |
| KHDRBS2 | uc003peg.1 | 7.26E−03 | 3 | 3 | 21.4% | 2 | 2 | 5.1% | 5 | 5 | 9.4% |
| PTPRO | uc001rda.1 | 9.09E−03 | 3 | 3 | 21.4% | 1 | 1 | 2.6% | 4 | 4 | 7.5% |
| SYT4 | uc002law.1 | 1.23E−02 | 3 | 3 | 21.4% | 1 | 1 | 2.6% | 4 | 4 | 7.5% |
| UGT2B10 | uc003hee.1 | 2.13E−02 | 3 | 3 | 21.4% | 1 | 1 | 2.6% | 4 | 4 | 7.5% |
| SLC6A11 | uc003bvz.1 | 2.84E−02 | 3 | 3 | 21.4% | 0 | 0 | 0.0% | 3 | 3 | 5.7% |
| SLC17A5 | uc003phn.2 | 7.91E−03 | 4 | 3 | 21.4% | 0 | 0 | 0.0% | 4 | 3 | 5.7% |
| C12orf63 | uc001tet.1 | 4.46E−02 | 4 | 3 | 21.4% | 2 | 2 | 5.1% | 6 | 5 | 9.4% |
| PCDHB8 | uc003liu.1 | 4.80E−02 | 3 | 3 | 21.4% | 1 | 1 | 2.6% | 4 | 4 | 7.5% |

TABLE 3

Somatic mutations identified in the Discovery, Prevalence and Validation Screens

| Gene Name | CCDS number | No. of mutations (% of tumors affected) | Tumor Name | Nucleotide Change | Amino Acid Change | Type of Mutation | Hete/Homo | Sample Panel |
|---|---|---|---|---|---|---|---|---|
| GRIN2A | CCDS10539.1 | 18 (34%)^ | B12 | G20A | W7* | Stop | Heterozygous | Validation set 2 |
|  |  | 12 (28.2%)⁻ | 17T | C170T | P57L | Nonsynonymous | Heterozygous | Prevalence screen |
|  |  | 7 (15.6%)† | MB1227 | T547A | F183I | Nonsynonymous | Heterozygous | Validation set 1 |
|  |  |  | 83T | G754A | D252N | Nonsynonymous | Heterozygous | Prevalence screen |
|  |  |  | MD_13 | C833T | S278F | Nonsynonymous | Heterozygous | Validation set 2 |
|  |  |  | 96T | C833T | S278F | Nonsynonymous | Heterozygous | Exome Capture |
|  |  |  | 9T | G1028A | W343* | Stop | Heterozygous | Exome Capture |
|  |  |  | MB487 | G1111A | E371K | Nonsynonymous | Heterozygous | Validation set 1 |
|  |  |  | 18T | G1111A | E371K | Nonsynonymous | Heterozygous | Exome Capture |
|  |  |  | B01x | G1116A | W372* | Stop | Heterozygous | Validation set 2 |
|  |  |  | 123T | G1117A | E373K | Nonsynonymous | Heterozygous | Prevalence screen |
|  |  |  | 24T | G1346A | G449E | Nonsynonymous | Heterozygous | Exome Capture |
|  |  |  | 110T | T1376C | F459S | Nonsynonymous | Heterozygous | Prevalence screen |
|  |  |  | MD_09 | A1784G | H595R | Nonsynonymous | Heterozygous | Validation set 2 |
|  |  |  | 114T | C1793T | S598F | Nonsynonymous | Heterozygous | Prevalence screen |
|  |  |  | MB490 | G1959A | M653I | Nonsynonymous | Heterozygous | Validation set 1 |
|  |  |  | 91T | G2135A | G712E | Nonsynonymous | Heterozygous | Exome Capture |
|  |  |  | MB532 | G2218A | G740W | Nonsynonymous | Heterozygous | Validation set 1 |
|  |  |  | MB669 | G2666A | G889E | Nonsynonymous | Heterozygous | Validation set 1 |
|  |  |  | MB1337 | C2671T | Q891* | Stop | Heterozygous | Validation set 1 |
|  |  |  | MD_13 | G2759A | R920K | Nonsynonymous | Heterozygous | Validation set 2 |
|  |  |  | MB1113 | C2786T | S929F | Nonsynonymous | Heterozygous | Validation set 1 |
|  |  |  | 119T | G2884A | E962K | Nonsynonymous | Heterozygous | Prevalence screen |
|  |  |  | MB490 | G3217A | E1073K | Nonsynonymous | Heterozygous | Validation set 1 |
|  |  |  | MB1160 | C3221T | P1074L | Nonsynonymous | Heterozygous | Validation set 1 |
|  |  |  | 88T | G3457A | D1153N | Nonsynonymous | Heterozygous | Prevalence screen |
|  |  |  | 501_Mel | G3523A | E1175K | Nonsynonymous | Heterozygous | Commercial cell line |
|  |  |  | 125T | G3523A | E1175K | Nonsynonymous | Heterozygous | Prevalence screen |
|  |  |  | 14T | G3812A | W1271* | Stop | Heterozygous | Prevalence screen |
|  |  |  | 98T | G3812A | W1271* | Stop | Heterozygous | Prevalence screen |
|  |  |  | MB706 | C3827G | A1276G | Nonsynonymous | Heterozygous | Validation set 1 |
|  |  |  | MB929 | G3854A | R1285K | Nonsynonymous | Heterozygous | Validation set 1 |
|  |  |  | 95T | C3952T | R1318W | Nonsynonymous | Heterozygous | Prevalence screen |
|  |  |  | 86T | C4097T | P1366L | Nonsynonymous | Heterozygous | Prevalence screen |
|  |  |  | B12 | G4261A | D1421N | Nonsynonymous | Heterozygous | Validation set 2 |
|  |  |  | MB1335 | C4274T | S1425L | Nonsynonymous | Heterozygous | Validation set 1 |
|  |  |  | 43T | G4276A | E1426K | Nonsynonymous | Heterozygous | Exome Capture |
|  |  |  | D03x | C4385G | S1462C | Nonsynonymous | Heterozygous | Validation set 2 |
| CCDC63 | CCDS9151.1 | 6 (11.3%)^ | 91T | C140T | S47F | Nonsynonymous | Heterozygous | Exome Capture |
|  |  |  | 93T | G443A | R148Q | Nonsynonymous | Heterozygous | Exome Capture |
|  |  |  | 29T | G850A | E284K | Nonsynonymous | Heterozygous | Prevalence screen |
|  |  |  | 81T | G1068A | R356Q | Nonsynonymous | Heterozygous | Prevalence screen |
|  |  |  | 43T | G1078A | E360K | Nonsynonymous | Homozygous | Exome Capture |
|  |  |  | 01T | G1366A | D456N | Nonsynonymous | Heterozygous | Exome Capture |
| TMEM132B | CCDS41859.1 | 10 (17%)^ | 60T | C854T | S285L | Nonsynonymous | Heterozygous | Exome Capture |
|  |  |  | 05T | A1207G | M403V | Nonsynonymous | Heterozygous | Exome Capture |
|  |  |  | 119T | G1597A | G533S | Nonsyncnymous | Heterozygous | Prevalence screen |
|  |  |  | 20T | C1907T | S636L | Nonsynonymous | Heterozygous | Prevalence screen |
|  |  |  | 51T | A1976T | E659V | Nonsynonymous | Heterozygous | Exome Capture |
|  |  |  | 05T | G2254A | G752S | Nonsynonymous | Heterozygous | Exome Capture |
|  |  |  | 83T | C2450T | S817F | Nonsynonymous | Heterozygous | Prevalence screen |
|  |  |  | 116T | G2465A | G822E | Nonsynonymous | Heterozygous | Prevalence screen |
|  |  |  | 12T | G2465A | G822E | Nonsynonymous | Heterozygous | Exome Capture |
|  |  |  | 108T | C2890T | P964S | Nonsynonymous | Heterozygous | Prevalence screen |
| ZNF831 | CCDS42894.1 | 10 (17%)^ | 91T | C1357T | H453Y | Nonsynonymous | Heterozygous | Exome Capture |
|  |  |  | 96T | C1424T | T475M | Nonsynonymous | Heterozygous | Exome Capture |
|  |  |  | 86T | C2138G | T713R | Nonsynonymous | Heterozygous | Prevalence screen |
|  |  |  | 64T | C3229T | R1077C | Nonsynonymous | Heterozygous | Prevalence screen |
|  |  |  | 90T | G3956A | S1319N | Nonsynonymous | Heterozygous | Prevalence screen |
|  |  |  | 81T | C4070T | S1357L | Nonsynonymous | Heterozygous | Prevalence screen |
|  |  |  | 43T | C4421T | S1474F | Nonsynonymous | Heterozygous | Exome Capture |
|  |  |  | 91T | C4421T | S1474F | Nonsynonymous | Heterozygous | Exome Capture |
|  |  |  | 119T | C4514T | A1505V | Nonsynonymous | Heterozygous | Prevalence screen |
|  |  |  | 05T | G4687A | E1563K | Nonsynonymous | Heterozyqous | Exome Capture |
| PLCB4 | CCDS13104.1 | 8 (15.1%)^ | 12T | T248C | L83P | Nonsynonymous | Heterozygous | Exome Capture |
|  |  |  | 91T | C494T | P165L | Nonsynonymous | Heterozygous | Exome Capture |
|  |  |  | 83T | G752A | R251Q | Nonsynonymous | Heterozygous | Prevalence screen |
|  |  |  | 119T | C1025T | S342L | Nonsynonymous | Heterozygous | Prevalence screen |
|  |  |  | 84T | G1486A | D496N | Nonsynonymous | Heterozygous | Prevalence screen |
|  |  |  | 8T | G2209A | E737K | Nonsynonymous | Heterozygous | Prevalence screen |
|  |  |  | 01T | C2314T | R772W | Nonsynonymous | Heterozygous | Exome Capture |
|  |  |  | 9T | G3292A | E1098K | Nonsynonymous | Heterozyqous | Exome Capture |

TABLE 3-continued

Somatic mutations identified in the Discovery, Prevalence and Validation Screens

| Gene Name | CCDS number | No. of mutations (% of tumors affected) | Tumor Name | Nucleotide Change | Amino Acid Change | Syn/NonSyn | Hete/Homo | Sample Panel |
|---|---|---|---|---|---|---|---|---|
| AKR1B10 | CCDS5832.1 | 4 (7.5%)^ | 91T | G400A | G134R | Nonsynonymous | Homozygous | Exome Capture |
| | | | 01T | G691A | D231N | Nonsynonymous | Heterozygous | Exome Capture |
| | | | 24T | A730C | T244P | Nonsynonymous | Heterozygous | Exome Capture |
| | | | 7T | Exon 2 (−8) C/T | N/A | splice site | Heterozygous | Prevalence screen |
| TAS2R60 | CCDS5885.1 | 5 (9.4%)^ | 92T | C272T | P91L | Nonsynonymous | Homozygous | Prevalence screen |
| | | | 60T | G429A | W143* | Stop | Heterozygous | Exome Capture |
| | | | 9T | G449A | G150E | Nonsynonymous | Heterozygous | Exome Capture |
| | | | 17T | G639A | M213I | Nonsynonymous | Heterozygous | Prevalence screen |
| | | | 43T | G639A | M213I | Nonsynonymous | Heterozygous | Exome Capture |
| KHDRBS2 | CCDS4963.1 | 5 (9.4%)^ | 119T | T82A | L28M | Nonsynonymous | Heterozygous | Prevalence screen |
| | | | 60T | C178T | L60F | Nonsynonymous | Heterozygous | Exome Capture |
| | | | 91T | C556T | R186C | Nonsynonymous | Heterozygous | Exome Capture |
| | | | 05T | C299T | R224W | Nonsynonymous | Homozygous | Exome Capture |
| | | | 109T | C733T | P245S | Nonsynonymous | Heterozygous | Prevalence screen |
| PTPRO | CCDS8675.1 | 4 (7.5%)^ | 12T | G127A | E43K | Nonsynonymous | Heterozygous | Exome Capture |
| | | | 24T | T297G | F99L | Nonsynonymous | Heterozygous | Exome Capture |
| | | | 95T | C838A | S280Y | Nonsynonymous | Heterozygous | Prevalence screen |
| | | | 60T | C847T | R283* | Stop | Heterozygous | Exome Capture |
| SYT4 | CCDS11922.1 | 4 (7.5%)^ | 43T | G37A | E13K | Nonsynonymous | Heterozygous | Exome Capture |
| | | | 22T | G119A | R40K | Nonsynonymous | Heterozygous | Exome Capture |
| | | | 12T | G388A | E130K | Nonsynonymous | Homozygous | Exome Capture |
| | | | 119T | G1151A | R384Q | Nonsynonymous | Heterozygous | Prevalence screen |
| UGT2B10 | N/A | 4 (7.5%)^ | 12T | C1177T | P393S | Nonsynonymous | Heterozygous | Exome Capture |
| | | | 96T | G1412A | G471E | Nonsynonymous | Heterozygous | Exome Capture |
| | | | 60T | A1586G | *529W | Nonsynonymous | Heterozygous | Exome Capture |
| | | | 116T | Exon 4 (−1) | N/A | Splice site | Heterozygous | Prevalence screen |
| SLC6A11 | CCDS2602.1 | 3 (5.7%)^ | 05T | C660A | H220Q | Nonsynonymous | Heterozygous | Exome Capture |
| | | | 12T | G1084A | E362K | Nonsynonymous | Heterozygous | Exome Capture |
| | | | 51T | G1435A | V479M | Nonsynonymous | Homozygous | Exome Capture |
| SLC17A5 | CCDS4981.1 | 4 (5.7%)^ | 24T | G776A | S259F | Nonsynonymous | Heterozygous | Exome Capture |
| | | | 24T | G862A | S288P | Nonsynonymous | Heterozygous | Exome Capture |
| | | | 12T | C1090T | R364C | Nonsynonymous | Heterozygous | Exome Capture |
| | | | 18T | C1090T | R364C | Nonsynonymous | Heterozygous | Exome Capture |
| C12orf63 | CCDS9062.1 | 6 (9.4%)^ | 32T | C62T | S21F | Nonsynonymous | Heterozygous | Prevalence screen |
| | | | 91T | C700T | P234S | Nonsynonymous | Heterozygous | Exome Capture |
| | | | 12T | G848A | R283Q | Nonsynonymous | Heterozygous | Exome Capture |
| | | | 125T | G2857K | E953K | Nonsynonymous | Homozygous | Prevalence screen |
| | | | 93T | T3104C | L1035P | Nonsynonymous | Heterozygous | Exome Capture |
| | | | 93T | A3110G | Q1037R | Nonsynonymous | Heterozygous | Exome Capture |
| PCDHB8 | CCDS4250.1 | 4 (7.5%)^ | 12T | G385A | D129N | Nonsynonymous | Heterozygous | Exome Capture |
| | | | 18T | A713G | D238G | Nonsynonymous | Heterozygous | Exome Capture |
| | | | 56T | G931A | E311K | Nonsynonymous | Heterozygous | Prevalence screen |
| | | | 22T | G931A | E311K | Nonsynonymous | Homozygous | Exome Capture |

*Number of nonsynonymous, stop and splice site mutations observed and percent of tumors affected for each of the 16 genes in the panel of 53 untreated melanoma samples.
†Number of nonsynonymous, stop and splice site mutations observed and percent of tumors affected for each of the 16 genes in validation set 1 and validation set 2 respectively.
*refers to stop codon. Samples used in exome capture and prevalance screen were obtained from The Surgery Branch, National Cancer Institute. Validation set 1 samples were obtained from The Division of Medical Oncology, University of Colorado Denver School of Medicine. Validation set 2 samples were obtained from The University of Texas MD Anderson Cancer Center. 501_Mel is a commercially available melanoma cell line.

TABLE 4

SIFT analysis of somatic mutations identified in highly mutated genes

| Gene Name | Tumor Name | Amino Acid Change | Syn/NonSyn | Hete/Homo | Sample Panel | Functional Domain | change | SIFT score | SIFT median |
|---|---|---|---|---|---|---|---|---|---|
| BRAF | N/A | V600E | Nonsynonymous | Heterozygous | N/A | Pkinase | V600E | 0 | 2.81 |
| GRIN2A | B12 | W7* | Stop | Heterozygous | Validation set 2 | Signal Peptide | Stop | N/A | N/A |
| GRIN2A | 17T | P57L | Nonsynonymous | Heterozygous | Prevalence screen | PBP1_iGluR_NMDA_NR2 | P57L | 0.26 | 3.14 |
| GRIN2A | MB1227 | F183I | Nonsynonymous | Heterozygous | Validation set 1 | PBP1_iGluR_NMDA_NR2 | F183I | 0.11 | 2.78 |
| GRIN2A | 83T | D252N | Nonsynonymous | Heterozygous | Prevalence screen | PBP1_iGluR_NMDA_NR2 | D252N | 0.31 | 2.78 |
| GRIN2A | MD_13 | S278F | Nonsynonymous | Heterozygous | Validation set 2 | PBP1_iGluR_NMDA_NR2 | S278F | 0.01 | 2.85 |
| GRIN2A | 96T | S278F | Nonsynonymous | Heterozygous | Exome Capture | PBP1_iGluR_NMDA_NR2 | S278F | 0 01 | 2.85 |

TABLE 4-continued

SIFT analysis of somatic mutations identified in highly mutated genes

| Gene Name | Tumor Name | Amino Acid Change | Syn/NonSyn | Hete/Homo | Sample Panel | Functional Domain | change | SIFT score | SIFT median |
|---|---|---|---|---|---|---|---|---|---|
| GRIN2A | 9T | W343* | Stop | Heterozygous | Exome Capture | PBP1_iGluR_NMDA_NR2 | Stop | N/A | N/A |
| GRIN2A | MB487 | E371K | Nonsynonymous | Heterozygous | Validation set 1 | PBP1_iGluR_NMDA_NR2 | E371K | 1 | 2.8 |
| GRIN2A | 18T | E371K | Nonsynonymous | Heterozygous | Exome Capture | PBP1_iGluR_NMDA_NR2 | E371K | 1 | 2.8 |
| GRIN2A | B01x | W372* | Stop | Heterozygous | Validation set 2 | PBP1_iGluR_NMDA_NR2 | Stop | N/A | N/A |
| GRIN2A | 123T | E373K | Nonsynonymous | Heterozygous | Prevalence screen | PBP1_iGluR_NMDA_NR2 | E373K | 0.05 | 2.79 |
| GRIN2A | 24T | G449E | Nonsynonymous | Heterozygous | Exome Capture | N/A | G449E | 0.3 | 2.79 |
| GRIN2A | 110T | F459S | Nonsynonymous | Heterozygous | Prevalence screen | PBPb | F459S | 0 | 2.79 |
| GRIN2A | MD_09 | H595R | Nonsynonymous | Heterozygous | Validation set 2 | Lig_chan | H595R | 0.61 | 2.79 |
| GRIN2A | 114T | S598F | Nonsynonymous | Heterozygous | Prevalence screen | Lig_chan | S598F | 0.01 | 2.79 |
| GRIN2A | MB490 | M653I | Nonsynonymous | Heterozygous | Validation set 1 | Lig_chan | M653I | 0.11 | 2.79 |
| GRIN2A | 91T | G712E | Nonsynonymous | Heterozygous | Exome Capture | Lig_chan/PBPb | G712E | 0.01 | 2.79 |
| GRIN2A | MB532 | G740W | Nonsynonymous | Heterozygous | Validation set 1 | Lig_chan/PBPb | G740W | 0 | 2.88 |
| GRIN2A | MB669 | G889E | Nonsynonymous | Heterozygous | Validation set 1 | NMDAR2_C | G889E | 0.26 | 2.81 |
| GRIN2A | MB1337 | Q891* | Stop | Heterozygous | Validation set 1 | NMDAR2_C | Stop | N/A | N/A |
| GRIN2A | MD_13 | R920K | Nonsynonymous | Heterozygous | Validation set 2 | NMDAR2_C | R920K | 0.54 | 2.98 |
| GRIN2A | MB1113 | S929F | Nonsynonymous | Heterozygous | Validation set 1 | NMDAR2_C | S929F | 0.01 | 3.37 |
| GRIN2A | 119T | E962K | Nonsynonymous | Heterozygous | Prevalence screen | NMDAR2_C | E962K | 0 01 | 3.42 |
| GRIN2A | MB490 | E1073K | Nonsynonymous | Heterozygous | Validation set 1 | NMDAR2_C | E1073K | 0.05 | 3.37 |
| GRIN2A | MB1160 | P1074L | Nonsynonymous | Heterozygous | Validation set 1 | NMDAR2_C | P1074L | 1 | 3.37 |
| GRIN2A | 88T | D1153N | Nonsynonymous | Heterozygous | Prevalence screen | NMDAR2_C | D1153N | 0.32 | 3.37 |
| GRIN2A | 501Mel | E1175K | Nonsynonymous | Heterozygous | Commercial cell line | NMDAR2_C | E1175K | 1 | 3.4 |
| GRIN2A | 125T | E1175K | Nonsynonymous | Heterozygous | Prevalence screen | NMDAR2_C | E1175K | 1 | 3.4 |
| GRIN2A | 98T | W1271* | Stop | Heterozygous | Prevalence screen | NMDAR2_C | Stop | N/A | N/A |
| GRIN2A | MB706 | A1276G | Nonsynonymous | Heterozygous | Validation set 1 | NMDAR2_C | A1276G | 0.34 | 3.37 |
| GRIN2A | MB929 | R1285K | Nonsynonymous | Heterozygous | Validation set 1 | NMDAR2_C | R1285K | 0.19 | 3.37 |
| GRIN2A | 95T | R1318W | Nonsynonymous | Heterozygous | Prevalence screen | NMDAR2_C | R1318W | 0 | 3.37 |
| GRIN2A | 86T | P1366L | Nonsynonymous | Heterozygous | Prevalence screen | NMDAR2_C | P1366L | 0 | 3.37 |
| GRIN2A | B12 | D1421N | Nonsynonymous | Heterozygous | Validation set 2 | NMDAR2_C | D1421N | 0.15 | 3.37 |
| GRIN2A | MB1335 | S1425L | Nonsynonymous | Heterozygous | Validation set 1 | NMDAR2_C | S1425L | 0 04 | 3.36 |
| GRIN2A | 43T | E1426K | Nonsynonymous | Heterozygous | Exome Capture | NMDAR2_C | E1426K | 0.26 | 3.36 |
| GRIN2A | D03x | S1462C | Nonsynonymous | Heterozygous | Validation set 2 | NMDAR2_C | S1462C | 0 | 3.37 |
| CCDC63 | 91T | S47F | Nonsynonymous | Heterozygous | Exome Capture | No domain altered | S47F | 0.01 | 2.8 |
| CCDC63 | 93T | R148Q | Nonsynonymous | Heterozygous | Exome Capture | No domain altered | R148Q | 0.36 | 2.8 |
| CCDC63 | 29T | E284K | Nonsynonymous | Heterozygous | Prevalence screen | Filament | E284K | 0.24 | 2.8 |
| CCDC63 | 81T | R356Q | Nonsynonymous | Heterozygous | Prevalence screen | Filament | R356Q | 0.46 | 2.8 |
| CCDC63 | 43T | E360K | Nonsynonymous | Homozygous | Exome Capture | Filament | E360K | 0.12 | 2.8 |
| CCDC63 | 01T | D456N | Nonsynonymous | Heterozygous | Exome Capture | Filament | D456N | 0.03 | 2.93 |

TABLE 4-continued

SIFT analysis of somatic mutations identified in highly mutated genes

| Gene Name | Tumor Name | Amino Acid Change | Syn/NonSyn | Hete/Homo | Sample Panel | Functional Domain | change | SIFT score | SIFT median |
|---|---|---|---|---|---|---|---|---|---|
| TMEM132B | 60T | S285L | Nonsynonymous | Heterozygous | Exome Capture | DUF59 | S285L | 0.46 | 2.85 |
| TMEM132B | 05T | M403V | Nonsynonymous | Heterozygous | Exome Capture | No domain altered | M403V | 0.36 | 2.8 |
| TMEM132B | 119T | G533S | Nonsynonymous | Heterozygous | Prevalence screen | No domain altered | G533S | 0 | 2.78 |
| TMEM132B | 20T | S636L | Nonsynonymous | Heterozygous | Prevalence screen | No domain altered | S636L | 0 | 2.79 |
| TM EM132B | 51T | E659V | Nonsynonymous | Heterozygous | Exome Capture | No domain altered | E659V | 0.03 | 2.79 |
| TMEM132B | 05T | G752S | Nonsynonymous | Heterozygous | Exome Capture | No domain altered | G752S | 0.31 | 2.78 |
| TMEM132B | 83T | S817F | Nonsynonymous | Heterozygous | Prevalence screen | No domain altered | S817F | 0.05 | 2.94 |
| TMEM132B | 116T | G822E | Nonsynonymous | Heterozygous | Prevalence screen | No domain altered | G822E | 1 | 2.97 |
| TMEM132B | 12T | G822E | Nonsynonymous | Heterozygous | Exome Capture | No domain altered | G822E | 1 | 2.97 |
| TMEM132B | 108T | P964S | Nonsynonymous | Heterozygous | Prevalence screen | No domain altered | P964S | 0.45 | 2.96 |
| ZNF831 | 91T | H453Y | Nonsynonymous | Heterozygous | Exome Capture | No domain altered | H453Y | 0.04 | 2.3 |
| ZNF831 | 96T | T475M | Nonsynonymous | Heterozygous | Exome Capture | No domain altered | T475M | 0 | 2.19 |
| ZNF831 | 86T | T713R | Nonsynonymous | Heterozygous | Prevalence screen | No domain altered | T713R | 0.61 | 2.04 |
| ZNF831 | 64T | R1077C | Nonsynonymous | Heterozygous | Prevalence screen | No domain altered | R1077C | 0.22 | 2.12 |
| ZNF831 | 90T | S1319N | Nonsynonymous | Heterozygous | Prevalence screen | No domain altered | S1319N | 0.36 | 2.35 |
| ZNF831 | 81T | S1357L | Nonsynonymous | Heterozygous | Prevalence screen | No domain altered | S1357L | 0.17 | 2.53 |
| ZNF831 | 43T | S1474F | Nonsynonymous | Heterozygous | Exome Capture | No domain altered | S1474F | 0.74 | 2.48 |
| ZNF831 | 91T | S1474F | Nonsynonymous | Heterozygous | Exome Capture | No domain altered | S1474F | 0.74 | 2.48 |
| ZNF831 | 119T | A1505V | Nonsynonymous | Heterozygous | Prevalence screen | No domain altered | A1505V | 0.2 | 2.33 |
| ZNF831 | 05T | E1563K | Nonsynonymous | Heterozygous | Exome Capture | No domain altered | E1563K | 0.87 | 2.42 |
| PLCB4 | 12T | L83P | Nonsynonymous | Heterozygous | Exome Capture | No domain altered | L83P | 0.02 | 2.79 |
| PLCB4 | 91T | P165L | Nonsynonymous | Heterozygous | Exome Capture | No domain altered | P165L | 0 | 2.79 |
| PLCB4 | 83T | R251Q | Nonsynonymous | Heterozygous | Prevalence screen | No domain altered | R251Q | 0 | 2.79 |
| PLCB4 | 119T | S342L | Nonsynonymous | Heterozygous | Prevalence screen | PI-PLC-X | S342L | 0 | 2.79 |
| PLCB4 | 84T | D496N | Nonsynonymous | Heterozygous | Prevalence screen | No domain altered | D496N | 0.28 | 2.77 |
| PLCB4 | 8T | E737K | Nonsynonymous | Heterozygous | Prevalence screen | C2 | E737K | 0.85 | 2.77 |
| PLCB4 | 01T | R772W | Nonsynonymous | Heterozygous | Exome Capture | No domain altered | R772W | 0.09 | 2.12 |
| PLCB4 | 9T | E1098K | Nonsynonymous | Heterozygous | Exome Capture | No domain altered | E1098K | 0.33 | 2.4 |
| AKR1B10 | 91T | G134R | Nonsynonymous | Homozygous | Exome Capture | Aldo_ket_red | G134R | 0.01 | 2.84 |
| AKR1B10 | 01T | D231 N | Nonsynonymous | Heterozygous | Exome Capture | Aldo_ket_red | D231N | 0.08 | 2.84 |
| AKR1B10 | 24T | T244P | Nonsynonymous | Heterozygous | Exome Capture | Aldo_ket_red | T244P | 0 | 2.84 |
| AKR1B10 | 7T | | splice site | Heterozygous | Prevalence screen | No domain altered | splice site | N/A | N/A |
| TAS2R60 | 92T | P91L | Nonsynonymous | Homozygous | Prevalence screen | 7tm_1 | P91L | 1 | 2.89 |
| TAS2R60 | 60T | | Stop | Heterozygous | Exome Capture | No domain altered | Stop | N/A | N/A |
| TAS2R60 | 9T | G150E | Nonsynonymous | Heterozygous | Exome Capture | 7tm_1 | G150E | 0.02 | 2.86 |
| TAS2R60 | 17T | M213I | Nonsynonymous | Heterozygous | Prevalence screen | 7tm_1 | M213I | 1 | 2.86 |
| TAS2R60 | 43T | M213I | Nonsynonymous | Heterozygous | Exome Capture | 7tm_1 | M213I | 1 | 2.86 |

TABLE 4-continued

SIFT analysis of somatic mutations identified in highly mutated genes

| Gene Name | Tumor Name | Amino Acid Change | Syn/NonSyn | Hete/Homo | Sample Panel | Functional Domain | change | SIFT score | SIFT median |
|---|---|---|---|---|---|---|---|---|---|
| KHDRBS2 | 119T | L28M | Nonsynonymous | Heterozygous | Prevalence screen | No domain altered | L28M | 0.01 | 2.8 |
| KHDRBS2 | 60T | L60F | Nonsynonymous | Heterozygous | Exome Capture | No domain altered | L60F | 0.01 | 2.78 |
| KHDRBS2 | 91T | R186C | Nonsynonymous | Heterozygous | Exome Capture | No domain altered | R186C | 0.12 | 2.85 |
| KHDRBS2 | 05T | R224W | Nonsynonymous | Homozygous | Exome Capture | No domain altered | R224W | 0.01 | 2.91 |
| KHDRBS2 | 109T | P245S | Nonsynonymous | Heterozygous | Prevalence screen | No domain altered | P245S | 0.03 | 2.91 |
| PTPRO | 12T | E854K | Nonsynonymous | Heterozygous | Exome Capture | No domain altered | E854K | 0.57 | 2.27 |
| PTPRO | 24T | F938L | Nonsynonymous | Heterozygous | Exome Capture | No domain altered | F938L | 0.1 | 1.96 |
| PTPRO | 95T | S280Y | Nonsynonymous | Heterozygous | Prevalence screen | No domain altered | S280Y | 0 | 3.32 |
| PTPRO | 60T |  | Stop | Heterozygous | Exome Capture | No domain altered | Stop | N/A | N/A |
| SYT4 | 43T | E13K | Nonsynonymous | Heterozygous | Exome Capture | No domain altered | E13K | 0.05 | 3.37 |
| SYT4 | 22T | R40K | Nonsynonymous | Heterozygous | Exome Capture | No domain altered | R40K | 0.04 | 3.11 |
| SYT4 | 12T | E130K | Nonsynonymous | Homozygous | Exome Capture | No domain altered | E130K | 0.3 | 2.84 |
| SYT4 | 119T | R384Q | Nonsynonymous | Heterozygous | Prevalence screen | C2 | R384Q | 0.02 | 2.78 |
| UGT2B10 | 12T | P393S | Nonsynonymous | Heterozygous | Exome Capture | UDPGT | P393S | 0 | 2.73 |
| UGT2B10 | 96T | G471E | Nonsynonymous | Heterozygous | Exome Capture | UDPGT | G471E | 0 | 2.73 |
| UGT2B10 | 60T | *529W | Nonsynonymous | Heterozygous | Exome Capture | No domain altered |  | N/A | N/A |
| UGT2B10 | 116T |  | Splice site | Heterozygous | Prevalence screen | No domain altered | Splice site | N/A | N/A |
| SLC6A11 | 05T | H220Q | Nonsynonymous | Heterozygous | Exome Capture | SNF | H220Q | 0.16 | 2.74 |
| SLC6A11 | 12T | E362K | Nonsynonymous | Heterozygous | Exome Capture | SNF | E362K | 0.35 | 2.74 |
| SLC6A11 | 51T | V479M | Nonsynonymous | Homozygous | Exome Capture | SNF | V479M | 0.16 | 2.74 |
| C12orf63 | 32T | S21F | Nonsynonymous | Heterozygous | Prevalence screen | No domain altered | S21F | 0.07 | 3.09 |
| C12orf63 | 91T | P234S | Nonsynonymous | Heterozygous | Exome Capture | No domain altered | P234S | 0.8 | 3.36 |
| C12orf63 | 12T | R283Q | Nonsynonymous | Heterozygous | Exome Capture | No domain altered | R283Q | 0.29 | 3.12 |
| C12orf63 | 125T | E953K | Nonsynonymous | Homozygous | Prevalence screen | No domain altered | E953K | 0.13 | 2.72 |
| C12orf63 | 93T | L1035P | Nonsynonymous | Heterozygous | Exome Capture | No domain altered | L1035P | 0 | 4.32 |
| C12orf63 | 93T | Q1037R | Nonsynonymous | Heterozygous | Exome Capture | No domain altered | Q1037R | 0.33 | 3.12 |
| PCDHB8 | 12T | D129N | Nonsynonymous | Heterozygous | Exome Capture | No domain altered | D129N | 0 | 2.83 |
| PCDHB8 | 18T | D238G | Nonsynonymous | Heterozygous | Exome Capture | No domain altered | D238G | 0 | 2.83 |
| PCDHB8 | 56T | E311K | Nonsynonymous | Heterozygous | Prevalence screen | Cadherin | E311K | 0 | 2.83 |
| PCDHB8 | 22T | E311K | Nonsynonymous | Homozygous | Exome Capture | Cadherin | E311K | 0 | 2.83 |
| SLC17A5 | 24T | S259F | Nonsynonymous | Heterozygous | Exome Capture | MFS_1 | S259F | 0 | 2.76 |
| SLC17A5 | 24T | S288P | Nonsynonymous | Heterozygous | Exome Capture | Sugar_tr | S288P | 0 | 2.77 |
| SLC17A5 | 12T | R364C | Nonsynonymous | Heterozygous | Exome Capture | MFS_1 | R364C | 0 | 2.76 |
| SLC17A5 | 18T | R364C | Nonsynonymous | Heterozygous | Exome Capture | MFS_1 | R364C | 0 | 2.76 |

Alterations with a SIFT score highlighted in red are predicted to be deleterious to protein function.
N/A, not applicable

TABLE 5

Characteristics of melanoma patient samples used in this study

| Sample | Patient Age (years)* | Patient Gender | MetastaticTumor Site | Matched normal source |
|---|---|---|---|---|
| 1T† | 29 | F | Lung | Blood |
| 2T | 30 | M | Pectoral muscle | Blood |
| 3T | 18 | M | Forehead, subcutaneous | Blood |
| 4T | 33 | F | Supraclavicular, soft tissue | Blood |
| 4T | 34 | F | Lung | Blood |
| 5T | 47 | M | Iliac | Blood |
| 6T | 42 | M | Neck, soft tissue | Blood |
| 7T† | 53 | M | Stomach | Blood |
| 8T | 61 | M | Inguinal | Blood |
| 9T | 62 | M | Back, subcutaneous | Blood |
| 10T | 55 | M | Axilla | Blood |
| 12T | 53 | M | Upper arm, subcutaneous | Blood |
| 13T† | 49 | M | Chest wall, subcutaneous | Blood |
| 14T | 58 | F | Small bowel | Blood |
| 15T | 39 | M | Thigh, subcutaneous | Blood |
| 16T† | 62 | M | Lung | Blood |
| 17T† | 33 | M | Shoulder, subcutaneous | Blood |
| 18T | 55 | M | Clavicle, soft tissue | Blood |
| 19T† | 49 | M | Scapula, subcutaneous | Blood |
| 20T | 58 | F | Axilla | Blood |
| 21T | 59 | M | Omentum | Blood |
| 22T | 51 | M | Chest wall, subcutaneous | Blood |
| 23T | 44 | M | Lung | Blood |
| 24T | 49 | M | Axilla | Blood |
| 26T | 48 | F | Lung | Blood |
| 28T | 28 | F | Iliac | Blood |
| 29T | 51 | M | Inguinal | Blood |
| 30T | 53 | F | Lung | Blood |
| 31T | 49 | F | Thigh, subcutaneous | Blood |
| 32T | 58 | M | Omentum | Blood |
| 33T | 33 | M | Chest wall, subcutaneous, & pleura ** | Blood |
| 34T† | 31 | M | Shoulder, subcutaneous | Blood |
| 35T | 23 | F | Thigh, subcutaneous | Blood |
| 36T† | 25 | M | Thigh, subcutaneous | Blood |
| 37T | 38 | F | Omentum | Blood |
| 38T | 27 | M | Skull versus Dura | Blood |
| 39T | 56 | M | Mesentery | Blood |
| 41T | 45 | M | Neck, soft tissue | Blood |
| 43T | 19 | F | Popliteal soft tissue | Blood |
| 44T | 56 | M | Lung | Blood |
| 45T | 48 | M | Mediastinum | Blood |
| 47T | 42 | F | Abdomen, subcutaneous | Blood |
| 48T | 28 | M | Back, soft tissue | Blood |
| 49T | 43 | M | Thigh, subcutaneous | Blood |
| 50T | 49 | F | Inguinal | Blood |
| 51T | 50 | F | Adnexa | Blood |
| 52T | 39 | F | Lung | Blood |
| 53T | 48 | F | Breast | Blood |
| 55T | 60 | M | Lung | Blood |
| 56T | 52 | M | Lung | Blood |
| 58T | 46 | F | Hip, subcutaneous | Blood |
| 59T | 64 | F | Abdomen, subcutaneous | Blood |
| 60T | 46 | M | Flank, subcutaneous | Blood |
| 62T | 58 | F | Thigh, subcutaneous | Blood |
| 63T | 30 | M | Small Bowel | Blood |
| 64T† | 32 | F | Ovary | Blood |
| 67T | 0 | M | Back, subcutaneous | Blood |
| 68T | 49 | M | Lung | Blood |
| 69T | 36 | M | Axilla | Blood |
| 71T | 67 | M | Lung | Blood |
| 72T | 53 | M | Liver | Blood |
| 73T | 45 | F | Breast | Blood |
| 74T | 40 | F | Lower extremity, subcutaneous | Blood |
| 75T | 0 | F | Upper arm, subcutaneous | Blood |
| 76T | 40 | M | Neck, soft tissue | Blood |
| 77T | 39 | M | Lung | Blood |
| 78T | 27 | F | Lung | Blood |
| 79T | 0 | M | Supraclavicular, soft tissue | Blood |
| 80T | 36 | M | Popliteal | Blood |
| 81T | 60 | F | Upper arm, subcutaneous | Blood |
| 82T | 0 | M | Axilla | Blood |
| 83T | 33 | F | Back, subcutaneous | Blood |
| 84T | 60 | F | Thigh, subcutaneous | Blood |
| 85T† | 44 | M | Chest wall, subcutaneous | Blood |
| 86T | 42 | F | Liver | Blood |

TABLE 5-continued

Characteristics of melanoma patient samples used in this study

| Sample | Patient Age (years)* | Patient Gender | Metastatic Tumor Site | Matched normal source |
|---|---|---|---|---|
| 87T | 0 | M | Small bowel & mesentary ** | Blood |
| 88T | 37 | F | Chest wall, subcutaneous | Blood |
| 90T | 19 | M | Neck, soft tissue | Blood |
| 91T | 55 | F | Subcostal soft tissue | Blood |
| 92T | 37 | F | Femur | Blood |
| 93T | 0 | F | Axilla | Blood |
| 94T | 44 | M | Adrenal gland | Blood |
| 95T† | 58 | F | Inguinal | Blood |
| 96T | 49 | M | Inguinal | Blood |
| 98T | 58 | F | Small Bowel | Blood |
| 99T | 57 | M | Liver | Blood |
| 100T | 28 | M | Chest wall, soft tissue | Blood |
| 101T | 0 | M | Omentum | Blood |
| 103T | 35 | F | Axilla | Blood |
| 104T | 56 | M | Thigh, subcutaneous | Blood |
| 105T | 28 | M | Neck, soft tissue | Blood |
| 106T | 41 | F | Lung | Blood |
| 107T | 0 | F | Liver | Blood |
| 108T | 0 | F | Thigh, subcutaneous | Blood |
| 109T | 0 | M | Scrotum | Blood |
| 110T | 0 | M | Axilla | Blood |
| 111T | 0 | M | Axilla | Blood |
| 112T | 0 | M | Inguinal | Blood |
| 113T | 0 | M | Axilla | Blood |
| 114T | 0 | M | Adrenal gland | Blood |
| 115T | 0 | M | Brain | Blood |
| 116T | 0 | M | Thigh, subcutaneous | Blood |
| 117T | 0 | M | Chest wall, subcutaneous | Blood |
| 119T | 0 | M | Axilla | Blood |
| 120T | 0 | M | Lung | Blood |
| 122T | 0 | F | Lung | Blood |
| 123T | 0 | M | Anticubital | Blood |
| 124T | 0 | M | Inguinal | Blood |
| 125T | 0 | M | Axilla | Blood |
| 127T | 0 | F | Infraclavicular, soft tissue | Blood |
| 128T | 0 | M | Lung | Blood |
| A11 | 57 | M | LN | None |
| B01x | 49 | M | LN | Blood |
| B03 | 62 | F | LN | None |
| B05 | 47 | F | LN | None |
| B06 | 34 | M | LN | None |
| B07 | 77 | F | LN | None |
| B09 | 55 | M | Soft Tissue | None |
| B12 | 72 | M | LN | None |
| B19 | 64 | M | LN/Soft Tissue | None |
| C14 | 65 | M | LN met | None |
| C16 | 69 | M | LN met | None |
| C18 | 61 | F | Soft Tissue/Skin | None |
| C19 | 56 | M | Soft Tissue/Skin | None |
| C22 | 56 | M | LN | None |
| C29 | 65 | F | Soft Tissue/Skin | None |
| C30x | 51 | M | Soft Tissue/Skin | None |
| C31x | 83 | F | LN | None |
| D03x | 68 | F | LN | None |
| D13 | 70 | F | LN | None |
| D16 | 68 | M | LN | Blood |
| D22 | 77 | M | LN | None |
| D23 | 69 | M | LN | None |
| MD_04 | 61 | F | LN | None |
| MD_09 | 27 | M | Soft Tissue | None |
| MD_13 | 62 | F | Small Intestine | None |
| MD_14 | 91 | F | LN | None |
| MD_15 | 28 | F | LN | Blood |
| MD_16 | 45 | F | Lung | None |
| MD_22 | 58 | M | Brain | Blood |
| MD_35 | 38 | F | Liver | None |
| MD_37 | 53 | F | Liver | None |
| MD_40 | 74 | F | Liver | None |
| MB532 | 44 | F | Lymph Node | Blood |
| MB669 | 59 | M | Bowel Small | Blood |
| MB930-T | 64 | M | Bone Spine | Blood |
| MB1089 | 56 | F | Liver | Blood |
| MB1160 | 61 | F | Lymph Node | Blood |
| MB1245 | 41 | M | Bowel Small | Blood |
| MB1287 | 83 | M | Subcutaneous Neck | Blood |

TABLE 5-continued

Characteristics of melanoma patient samples used in this study

| Sample | Patient Age (years)* | Patient Gender | MetastaticTumor Site | Matched normal source |
|---|---|---|---|---|
| MB1320 | 57 | F | Lymph Node | Blood |
| MB706 | 63 | M | Subcutaneous Back | Blood |
| MB929 | 69 | F | Subcutaneous Arm | Blood |
| MB947-LN | 67 | F | Lymph Node | Blood |
| MB1029 | 55 | M | Primary Skin | Blood |
| MB1046-LN | 70 | M | Lymph Node | Blood |
| MB1067 | 47 | F | Lymph Node | Blood |
| MB1082 | 61 | F | Subcutaneous Groin | Blood |
| MB1110 | 61 | F | Subcutaneous Arm | Blood |
| MB1113 | 63 | F | Muscle Back | Blood |
| MB1157 | 71 | F | Primary Skin | Blood |
| MB1222 | 25 | M | Lymph Node | Blood |
| MB87 | 53 | F | Brain | Blood |
| MB104 | 65 | M | Subcutaneous Back | Blood |
| MB106 | 67 | M | Bone Spine | Blood |
| MB107 | 47 | M | Brain | Blood |
| MB161 | 72 | F | Primary Vulvar Vag | Blood |
| MB298 | 53 | F | Brain | Blood |
| MB327 | 71 | F | Primary Vulvar Vag | Blood |
| MB363 | 69 | M | Subcutaneous Back | Blood |
| MB393 | 68 | M | Brain | Blood |
| MB402 | 52 | M | Lymph Node | Blood |
| MB404 | 67 | M | Muscle Gluteal | Blood |
| MB463 | 52 | M | Primary Skin | Blood |
| MB464 | 37 | F | Primary Skin | Blood |
| MB487 | 73 | M | Lymph Node | Blood |
| MB490 | 65 | F | Brain | Blood |
| MB505 | 75 | F | Subcutaneous Thigh | Blood |
| MB522 | 52 | M | Bowel Small | Blood |
| MB1227 | 41 | M | Subcutaneous Trunk | Blood |
| MB1335 | 61 | M | Primary Skin | Blood |
| MB1337 | 41 | M | Subcutaneous Thigh | Blood |

*Patient's age when tumor was surgically removed.
** Cell line generated from 2 metastatic melanoma tumors mixed after resection during the same operation.

TABLE 6

TRRAP primers used for recurrent mutation confirmation

| Primer set # | Primer Type | Hotspot Change | Sequence | SEQ ID NO: |
|---|---|---|---|---|
| TRRAP #1 | Forward | C2165T | GTAAAACGACGGCCAGTTAAAACTGCTTTGGGGAAGG | 19 |
| TRRAP #1 | Reverse | C2165T | GAGTGCCTATAGTCCCAAAAA | 20 |
| TRRAP #1 | Sequencing | C2165T | GTAAAACGACGGCCAGT | 21 |
| TRRAP #2 | Forward | C2165T | GTAAAACGACGGCCAGTTTGCTACGATTCTGGTGGAA | 22 |
| TRRAP #2 | Reverse | C2165T | CGTGAGGCCCTGTCTCTAAC | 23 |
| TRRAP #2 | Sequencing | C2165T | GTAAAACGACGGCCAGT | 24 |

TABLE 7

GRIN2A primers used for PCR and sequencing

| Primer Name | Coverage | Sequence | SEQ ID NO: |
|---|---|---|---|
| GRIN2A_1 Forward | Exon 1 | GTAAAACGACGGCCAGTCCTATCCTGCTGCTGAGTTCC | 25 |
| GRIN2A_1 Reverse | Exon 1 | AGTTTCCGGCCTTACCTTGTC | 26 |
| GRIN2A_2 | Exon 1 | GTAAAACGACGGCCAGTAGAGTGGGCTATTG | 27 |

TABLE 7-continued

GRIN2A primers used for PCR and sequencing

| Primer Name | Coverage | Sequence | SEQ ID NO: |
|---|---|---|---|
| Forward | | GACCCTG | |
| GRIN2A_2 Reverse | Exon 1 | GAGGCAAGACCTGGTTCTCAC | 28 |
| GRIN2A_3 Forward | Exon 2 | GTAAAACGACGGCCAGTCTAGGACGCAGTTTGTGCTTC | 29 |
| GRIN2A_3 Reverse | Exon 2 | GAACAGCCTCGTCTTTGGAAC | 30 |
| GRIN2A_4 Forward | Exon 2 | GTAAAACGACGGCCAGTGGCTACAGGGAATTCATCAGC | 31 |
| GRIN2A_4 Reverse | Exon 2 | TCAGTGCGTATTTCCAACAATG | 32 |
| GRIN2A_5 Forward | Exon 3 | GTAAAACGACGGCCAGTGCAGAGAGGCTTCTTGTGATG | 33 |
| GRIN2A_5 Reverse | Exon 3 | AGAAAGAAGCACTGTGAGCCC | 34 |
| GRIN2A_6 Forward | Exon 4 | GTAAAACGACGGCCAGTGGAAAGGATTTGCCTCTCCAG | 35 |
| GRIN2A_6 Reverse | Exon 4 | GCAAGTGTGGCACATCTCTAGG | 36 |
| GRIN2A_7 Forward | Exon 5 | GTAAAACGACGGCCAGTGTCCTTGGGAAAGCCACTTC | 37 |
| GRIN2A_7 Reverse | Exon 5 | CGTTGATAGACCACCTGGATG | 38 |
| GRIN2A_8 Forward | Exon 7 | GTAAAACGACGGCCAGTATGTCTGGGCTTCCTGCTG | 39 |
| GRIN2A_8 Reverse | Exon 7 | TCCTGACCTCATGATCCACC | 40 |
| GRIN2A_9 Forward | Exon 8 | GTAAAACGACGGCCAGTTTCCATCTTCTGGCAACCTTC | 41 |
| GRIN2A_9 Reverse | Exon 8 | TCAATGAGAGGCACCTGAATC | 42 |
| GRIN2A_10 Forward | Exon 9 | GTAAAACGACGGCCAGTTTGTCATCCTGCCCTAATGC | 43 |
| GRIN2A_10 Reverse | Exon 9 | CATGCCGAGAGTCAATTTCTG | 44 |
| GRIN2A_11 Forward | Exon 10 | GTAAAACGACGGCCAGTAAAGTGTGGGATGCTTTCAGG | 45 |
| GRIN2A_11 Reverse | Exon 10 | ATGCAAAGATCCACTGGGAAG | 46 |
| GRIN2A_12 Forward | Exon 11 | GTAAAACGACGGCCAGTGTCTGTTCCAAACCCAGAAGC | 47 |
| GRIN2A_12 Reverse | Exon 11 | TGAGACATCAAGAACCCAAGC | 48 |
| GRIN2A_13 Forward | Exon 12 | GTAAAACGACGGCCAGTCCCTATGCTTTGCAACTTGTC | 49 |
| GRIN2A_13 Reverse | Exon 12 | GAAACCATGTCCATGATGAGG | 50 |
| GRIN2A_14 Forward | Exon 12 | GTAAAACGACGGCCAGTCAGGCATCTACAGCTGCATTC | 51 |

TABLE 7-continued

GRIN2A primers used for PCR and sequencing

| Primer Name | Coverage | Sequence | SEQ ID NO: |
|---|---|---|---|
| GRIN2A_14 Reverse | Exon 12 | GGAGTGGGTCCTATTCTCTGC | 52 |
| GRIN2A_15 Forward | Exon 12 | GTAAAACGACGGCCAGTAGACAACAGGTCC TTTCAGGG | 53 |
| GRIN2A_15 Reverse | Exon 12 | TGTTGTCAGGTTCCCTGTGG | 54 |
| GRIN2A_16 Forward | Exon 12 | GTAAAACGACGGCCAGTATTCCATACGCCAG GATTCAC | 55 |
| GRIN2A_16 Reverse | Exon 12 | GTATCGCTCGCTGGTCTCAC | 56 |
| GRIN2A_17 Forward | Exon 12 | GTAAAACGACGGCCAGTAACGTGGACTTCCC GGAC | 57 |
| GRIN2A_17 Reverse | Exon 12 | GCCCAGTCCTGCTGGTAGAC | 58 |
| GRIN2A_18 Forward | Exon 12 | GTAAAACGACGGCCAGTGTGAGACCAGCGA GCGATAC | 59 |
| GRIN2A_18 Reverse | Exon 12 | GAAAGGGTTATCGGAGGTGTG | 60 |
| GRIN2A_19 Forward | Exon 12 | GTAAAACGACGGCCAGTGCTAGACCTTAGCA GGCCCTC | 61 |
| GRIN2A_19 Reverse | Exon 12 | TTTACCCTCCAGAACATTGGC | 62 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of diagnosing a human subject as having melanoma, or susceptible to developing melanoma, comprising:

detecting the presence of at least one mutation in the glutamate receptor, ionotropic, N-methyl-D-aspartate 2A (GRIN2A) gene (SEQ ID NO: 3) in a biological sample obtained from the human subject, wherein the at least one mutation comprises C2671 T and detecting the presence of the C2671 T mutation comprises amplification of nucleic acid from the biological sample using the primers of SEQ ID NO: 45 and SEQ ID NO: 46, and diagnosing the human subject as having melanoma or susceptible to developing melanoma based on the detection of the presence of the C2671T mutation.

2. The method of claim 1, further comprising detecting a mutation in the portion of the GRIN2A gene that encodes the PBP1_iGluR_NMDA_NR2 domain, wherein the mutation is C170T, T547A, G754A, C833T, G1028A, G1111A, G1116A or G1117A.

3. The method of claim 2, wherein the mutation in the portion of the GRIN2A gene that encodes the PBP1_iGluR_NMDA_NR2 domain is C833T or G1111A.

4. The method of claim 1, further comprising detecting a mutation in the portion of the GRIN2A gene that encodes the NMDAR2_C domain, wherein the mutation is G2666A, G2759A, C2786T, G2884A, G3217A, C3221T, G3457A, G3523A, G3812A, C3827G, G3854A, C3952T, C4097T, G4261A, C4274T, G4276A or C4385G.

5. The method of claim 4, wherein the mutation in the portion of the GRIN2A gene that encodes the NMDAR2_C domain is G3523A or G3812A.

6. The method of claim 1, further comprising detecting a mutation in the portion of the GRIN2A gene that encodes the Lig_chan domain, wherein the mutation is A1784G, C1793T, G1959A, G2135A or G2218A.

7. The method of claim 1, further comprising detecting a mutation in the transformation/transcription domain-associated protein (TRRAP) gene (SEQ ID NO: 1) wherein the mutation is C2165T.

8. The method of claim 1, further comprising providing a test output to a user, wherein the test output comprises information regarding the presence or absence of the C2671 T mutation, or a diagnosis regarding the human subject having melanoma or a susceptibility to developing melanoma, or a combination thereof.

9. The method of claim 1, further comprising administering an appropriate therapy to the subject, wherein the appropriate therapy comprises surgical removal of tumor tissue, radiation therapy, chemotherapy, or any combination of two or more thereof.

* * * * *